(12) United States Patent
Hasei et al.

(10) Patent No.: US 6,787,014 B2
(45) Date of Patent: Sep. 7, 2004

(54) GAS-DETECTING ELEMENT AND GAS-DETECTING DEVICE COMPRISING SAME

(75) Inventors: Masaharu Hasei, Saitama-ken (JP); Akira Kunimoto, Saitama-ken (JP); Yongtie Yan, Saitama-ken (JP); Takashi Ono, Saitama-ken (JP)

(73) Assignee: Kabushiki Kaisha Riken, Tokyo (JP)

( * ) Notice: Subject to any disclaimer, the term of this patent is extended or adjusted under 35 U.S.C. 154(b) by 0 days.

(21) Appl. No.: 10/266,918

(22) Filed: Oct. 9, 2002

(65) Prior Publication Data

US 2003/0205078 A1 Nov. 6, 2003

(30) Foreign Application Priority Data

Oct. 9, 2001 (JP) ........................................ 2001-311934

(51) Int. Cl.[7] ............................................. G01N 27/407
(52) U.S. Cl. ........................ 204/424; 204/426; 204/427; 204/429
(58) Field of Search ................................. 204/421–429

(56) References Cited

U.S. PATENT DOCUMENTS

| | | | |
|---|---|---|---|
| 3,645,875 A | * | 2/1972 | Record et al. |
| 4,021,326 A | * | 5/1977 | Pollner et al. |
| 4,402,820 A | * | 9/1983 | Sano et al. |
| 4,487,680 A | * | 12/1984 | Logothetis et al. |
| 4,879,016 A | * | 11/1989 | Joshi |
| 5,393,397 A | * | 2/1995 | Fukaya et al. |
| 6,076,393 A | * | 6/2000 | Kato et al. |
| 6,471,840 B1 | * | 10/2002 | Gao et al. |

OTHER PUBLICATIONS

Patent Abstract of JP 09–274011; Oct. 21, 1997; Riken Corp; *Nitrogen Oxide Detector*.
Patent Abstract of JP 11–072476; Mar. 16, 1999; Riken Corp; *Nitrogen Oxide Gas Sensor*.

* cited by examiner

*Primary Examiner*—Kaj K. Olsen
(74) *Attorney, Agent, or Firm*—Browdy and Neimark, P.L.L.C.

(57) ABSTRACT

A gas-detecting element comprising an oxygen-ion-conductive solid electrolyte substrate, a sensing electrode fixed onto said solid electrolyte substrate and active with a detection object gas and oxygen, and a reference electrode fixed onto said solid electrolyte substrate and active with at least oxygen, for detecting potential difference between the sensing electrode and the reference electrode to determine the concentration of the detection object gas, the sensing electrode and/or the reference electrode being covered by an electrode-coating layer made of an oxygen-ion-conductive solid electrolyte, and the electrode-coating layer having a portion bonded to the solid electrolyte substrate directly or via an electrode underlayer made of an oxygen-ion-conductive solid electrolyte.

6 Claims, 11 Drawing Sheets

(Detection Gas Atmosphere)

(Reference Gas Atmosphere)

(Detection Gas Atmosphere)

(Detection Gas Atmosphere)

GAS-DETECTING ELEMENT AND GAS-DETECTING DEVICE COMPRISING SAME

FIELD OF THE INVENTION

The present invention relates to a gas-detecting element and a gas-detecting device for measuring the concentration of a detection object gas in a gas atmosphere, particularly to a gas-detecting element and a gas-detecting device suitable for directly measuring the concentration of nitrogen oxides in a combustion exhaust gas emitted from automobiles, etc.

BACKGROUND OF THE INVENTION

So-called gas sensors with high gas selectivity capable of electrochemically detecting a particular gas by using solid electrolyte substrates have recently been proposed actively. Particularly, gas sensors capable of measuring the concentration of total NOx in an exhaust gas from automobiles without affected by other gases are strongly demanded.

Thus, the inventors previously proposed a mixed-potential-type NOx sensor comprising an oxygen-ion-conductive zirconia solid electrolyte operable at high temperatures in JP 9-274011 A. This NOx sensor has a basic structure, which comprises a NOx-sensing electrode and a reference electrode formed on an opposite or same surface of a zirconia solid electrolyte substrate as the NOx-sensing electrode. In this NOx sensor, a sensing electrode is, of course, exposed to a detection gas (gas to be detected), and a reference electrode can be simultaneously exposed to a detection gas, if the reference electrode is active with only oxygen. Because the NOx-sensing electrode is active with NOx and oxygen, and because the reference electrode is active only with oxygen, output (potential difference) can be obtained due to the difference in chemical potential between both electrodes. Accordingly, the measurement of potential difference between both electrodes leads to the detection of the NOx concentration in the detection gas. Incidentally, when the reference electrode is also active with NOx, the same NOx sensitivity can be obtained if isolated from the detection gas.

At the time of detecting a gas by the sensing electrode of the above mixed-potential-type NOx sensor, however, NO is subjected to reactions represented by the following formulae (1) and (2):

$$O_2 + 4e^- \rightarrow 2O^{2-} \quad (1), \text{ and}$$

$$2NO + 2O^{2-} \rightarrow 2NO_2 + 4e^- \quad (2),$$

and $NO_2$ is subjected to reactions represented by the following formulae (3) and (4):

$$2O^{2-} \rightarrow O_2 + 4e^- \quad (3), \text{ and}$$

$$2NO_2 + 4e^- \rightarrow 2NO + 2O^{2-} \quad (4).$$

As a result, sensor outputs with NO and $NO_2$ at the time of detecting a gas are just opposite in polarity. When the concentration of total NOx is detected in an exhaust gas emitted from vehicles, the coexistence of NO and $NO_2$ causes interference if no measure is taken, failing to detect the concentration of total NOx precisely.

Accordingly, JP 9-274011 A proposes a laminate-type gas-detecting device. According to the principle of this laminate-type gas-detecting device, oxygen from air is introduced into a gas detection chamber using an electrochemical oxygen pump. As a result, reducing gases such as HC (hydrocarbons), CO (carbon monoxide), etc. in the detection gas are oxidized to be harmless. Simultaneously, NO in NOx is electrochemically converted to $NO_2$, so that NOx becomes consisting only of $NO_2$. After this treatment for turning a detection gas to contain only one detection object gas, the $NO_2$ concentration is measured from the potential difference between the NOx-sensing electrode and the reference electrode, thereby determining the concentration of total NOx.

In such NOx-detecting element or such laminate-type NOx gas-detecting device, its detection performance, namely sensitivity and its stability and response, is particularly governed by the performance of a sensing electrode. Conventionally reported as the sensing electrodes of such mixed-potential-type NOx sensors are, for instance, $NiCr_2O_4$ (SAE Paper No. 961130), Pt—Rh alloys or cermet electrodes comprising Pt—Rh alloys to which a zirconia solid electrolyte is added (JP 11-72476 A). These sensing electrodes have excellent sensitivity. However, further improvement is needed with respect to the stability of sensitivity of sensing electrodes. For this purpose, it is important to improve the stability of an electrode material per se, and the bonding stability of interface (electrode interface) between a solid electrolyte substrate and a sensing electrode. Particularly when metal oxides are used for the electrodes, it has conventionally been difficult to control the bonding stability of this electrode interface. This is because there is generally weak bonding between metal oxides and solid electrolyte substrates, resulting in the likelihood that peeling and cracking occur in their interface.

To improve the response of gas detection, it is necessary to reduce the interface impedance of the electrode in the gas sensor. For this purpose, increase in an electrode area and the elevation of operation temperatures have been investigated. However, in a mixed-potential-type sensor, the higher the temperature, the lower the gas sensitivity. In addition, to increase an electrode area, it is necessary to make a sensor element larger. The increase of the sensor element deteriorates the uniformity of the temperature distribution of the sensor element, resulting in the variation of performance and instability.

As described above, though there are materials excellent in sensitivity for the mixed-potential-type NOx sensor, further improvement is needed with respect to the stability of sensitivity. Particularly when a metal oxide electrode is used as a sensing electrode, there is poor bonding stability with the solid electrolyte substrate, resulting in the variation of detection performance and decrease in yield. Therefore, it is desired not only to improve interface stability between the sensing electrode and the solid electrolyte substrate, but also to reduce the variation of characteristics that are caused during a production process for some reasons. Further, it is desired to improve gas response without making the sensor element larger, and without accompanying decrease in gas sensitivity.

Though the importance of stability and response of the sensing electrode has been described above, such characteristics are not required only to the sensing electrode. In the case of the NOx sensor, for instance, it is important to improve the stability and response of a reference electrode serving as a reference for electrode potential, and an oxygen-sensing electrode for making compensation for oxygen concentration, etc., because these characteristics also affect the performance of the NOx sensor.

In the case of a NOx sensor mounted onto a vehicle, oxygen concentration in the detection gas widely varies, and thus the influence of the concentration of coexisting oxygen cannot be neglected. In the NOx sensor of this type, a reference electrode active only with oxygen is disposed in a portion close to the NOx-sensing electrode, and the measurement of potential between the NOx-sensing electrode and the reference electrode leads to the determination of NOx concentration in the detection gas. By mounting an oxygen-sensing electrode active with oxygen but inactive with NOx near the NOx-sensing electrode within a detection chamber, by measuring potential difference $E_2$ between the reference electrode and the oxygen-sensing electrode disposed in an air duct, and potential difference $E_1$ between the reference electrode and the NOx-sensing electrode, and by arithmetically treating these difference ($E_1$–$E_2$), it is possible to compensate the variation of oxygen concentration. The measurement using such electrode inactive with a detection gas enables high-precision measurement of the concentration of a detection object gas even with a detection gas such as an exhaust gas from automobiles, etc. in which oxygen concentration varies.

However, if the reference electrode or the oxygen-sensing electrode becomes considerable active with NOx (exhibits mixed potential), its influence decreases the precision of NOx detection. To improve the sensitivity of the NOx sensor, it is desirable to reduce the activity of the reference electrode or the oxygen-sensing electrode with NOx. The activity of the reference electrode or the oxygen-sensing electrode with NOx is presumed to be generated by the contamination of these electrodes, vapor deposition from other electrodes evaporated during the sintering step, etc. Though the contamination can be prevented by control of the production process, the vapor deposition from other electrodes during the sintering step is inevitable because of the restrictions of the sintering conditions of substrates, sensing electrode characteristics, etc. Accordingly, it is important to minimize the activity of the reference electrode and the oxygen-sensing electrode with a detection gas such as NOx, etc., during the production and operation.

In the laminate-type NOx gas-detecting device, its detection performance is affected by the performance of the conversion electrode for electrochemically converting NO to $NO_2$ or $NO_2$ to NO in the NOx. Therefore, the conversion electrode should carry out the desired oxygen pumping. The factors for varying oxygen pumping are the change of electric resistance of a conversion electrode per se, the change of interface resistance between a conversion electrode and a solid electrolyte substrate, the change of bulk resistance of a solid electrolyte per se, etc. Also, the conversion electrode should have not only an excellent oxygen pumping function, but also excellent performance of adsorption and desorption of NO for electrochemically converting NO in the NOx to $NO_2$. From these facts, the conversion electrode should be excellent in electrochemical stability characteristics.

However, it is necessary to further improve the conversion electrode with respect to stability of sensitivity. For this purpose, it is important to have good bonding stability of interface (electrode interface) between the solid electrolyte substrate and the conversion electrode. By the difference in a sintering shrinkage ratio and a thermal expansion coefficient between the solid electrolyte substrate and the conversion electrode, it is difficult to maintain the bonding stability of electrode interface for a long period of time. Particularly when the conversion electrode contains a metal oxide, there is weak bonding with the solid electrolyte substrate, making it likely to cause peeling and cracking in the interface.

Further, when the conversion electrode comes into direct contact with a strong reducing gas such as HC (hydrocarbons), CO (carbon monoxide), etc., its performance of adsorption and desorption of NO is likely to be remarkably changed. The laminate-type, gas-detecting device of JP 9-274011 A oxidizes a reducing gas such as HC (hydrocarbons), CO (carbon monoxide), etc. in the detection gas to be harmless. However, when this gas-detecting device is used for automobiles, the temperature of the gas-detecting device is not so elevated at the time of starting an engine that the conversion pump element does not fully work. Thus, when exposed to HC and CO, the adsorption and desorption of NO is remarkably changed.

OBJECT OF THE INVENTION

Accordingly, an object of the present invention is to provide a gas-detecting element and a gas-detecting device excellent in the bonding stability of interface between an electrode and a solid electrolyte substrate, with the activity of a reference electrode or an oxygen-sensing electrode with a detection object gas suppressed, thereby exhibiting stable sensitivity and excellent response performance.

SUMMARY OF THE INVENTION

The first gas-detecting element of the present invention comprises an oxygen-ion-conductive solid electrolyte substrate, a sensing electrode fixed onto the solid electrolyte substrate and active with a detection object gas and oxygen, and a reference electrode fixed onto the solid electrolyte substrate and active with at least oxygen, to determine the concentration of the detection object gas from the potential difference between the sensing electrode and the reference electrode, wherein the sensing electrode and/or the reference electrode being covered by an electrode-coating layer made of an oxygen-ion-conductive solid electrolyte, the electrode-coating layer having a portion bonded to the solid electrolyte substrate directly or via an electrode underlayer made of an oxygen-ion-conductive solid electrolyte.

By covering a sensing electrode with an electrode-coating layer made of an oxygen-ion-conductive solid electrolyte, it is possible to reduce the bonding instability of interface between a solid electrolyte substrate and the sensing electrode, which is caused by thermal stress due to the difference in a thermal expansion coefficient between them. Though there is an electrode interface (three-phase interface) only in a bonding interface between a sensing electrode and a solid electrolyte substrate in a conventional gas-detecting element, a bonding interface between a sensing electrode and an electrode-coating layer also serves as an electrode interface in the gas-detecting element of the present invention, resulting in drastic increase in an electrode interface area. Accordingly, the electrode impedance can be reduced, resulting in improvement in gas response.

By covering a reference electrode with an electrode-coating layer made of an oxygen-ion-conductive solid electrolyte, the stability of interface and the gas response are also improved, like the sensing electrode. When the reference electrode is also exposed to a detection gas (a gas to be detected), the decrease of interface impedance leads to the increase of reaction sites of oxygen, as long as oxygen concentration is sufficiently higher than the concentration of a detection object gas in the detection gas. In this case, because reaction sites of a low concentration of a detection object gas (for instance, NOx) are not substantially influenced, the activity of the reference electrode to the detection object gas decreases. Further, the electrode-coating layer prevents contamination to the reference electrode during production processes and use of a sensor, so that the sensitivity of the reference electrode to the detection object gas can be kept low, resulting in improvement in the precision and stability of a sensor.

The second gas-detecting element of the present invention comprises an oxygen-ion-conductive solid electrolyte substrate, a sensing electrode fixed onto the solid electrolyte substrate and active with a detection object gas and oxygen, an oxygen-sensing electrode fixed onto the solid electrolyte substrate and active with at least oxygen, a reference electrode positioned in an atmosphere separated from a detection object atmosphere and active with oxygen, to determine the concentration of the detection object gas from the difference ($E_1-E_2$) between a potential difference $E_1$ between the sensing electrode and the reference electrode and a potential difference $E_2$ between the oxygen-sensing electrode and the reference electrode, wherein the sensing electrode and/or the oxygen-sensing electrode being covered by an electrode-coating layer made of an oxygen-ion-conductive solid electrolyte, the electrode-coating layer having a portion bonded to the solid electrolyte substrate directly or via an electrode underlayer made of an oxygen-ion-conductive solid electrolyte.

By covering a sensing electrode and/or an oxygen-sensing electrode with an electrode-coating layer, the bonding stability of interface between a sensing electrode and/or an oxygen-sensing electrode and a solid electrolyte substrate, and gas response are improved. Also, the oxygen-sensing electrode exposed to a detection gas has lowered activity with the detection object gas, and it is possible to prevent the oxygen-sensing electrode from having activity with a detection object gas by contamination, thereby improving the precision and stability of the detection element.

Preferred examples of the gas-detecting element of the present invention are as follows:

(1) The electrode-coating layer covering the sensing electrode and/or the reference electrode is in the form in which a detection gas can reach a three-phase interface between each electrode and the solid electrolyte substrate, the electrode underlayer or the electrode-coating layer.
(2) At least one of the sensing electrode, the reference electrode and the oxygen-sensing electrode is fixed onto the solid electrolyte substrate via an electric insulating layer.
(3) At least one of the sensing electrode, the reference electrode and the oxygen-sensing electrode is fixed in a recess formed on the solid electrolyte substrate.
(4) The electrode-coating layer covering the sensing electrode has a porosity of 10–50%.
(5) The electrode-coating layer covering the sensing electrode has an average thickness of 3–20 µm.
(6) The electrode-coating layer covering the reference electrode or the oxygen-sensing electrode has a porosity of 0–50%.
(7) The electrode-coating layer covering the reference electrode or the oxygen-sensing electrode has an average thickness of 1–20 µm.
(8) The electrode-coating layer covering at least one of the sensing electrode, the reference electrode and the oxygen-sensing electrode has an average thickness of 5–100 µm, and the electrode-coating layer is provided with gas-diffusing pores, a ratio (Sh/Se) of the total opening area (Sh) of the gas-diffusing pores to the area (Se) of the sensing electrode being 0.05–0.28.
(9) An upper surface of at least one electrode of the reference electrode and the oxygen-sensing electrode exposed to a detection gas is covered by a dense electrode-coating layer, and part of side surfaces of the electrode is exposed.
(10) A plurality of sensing electrodes are formed via the electrode-coating layer covering the sensing electrode.
(11) The electrode-coating layer covering at least one of the sensing electrode, the reference electrode and the oxygen-sensing electrode is made of a zirconia solid electrolyte containing at least one selected from the group consisting of yttria, ceria, magnesia and scandia as a stabilizer.
(12) The electrode-coating layer covering the sensing electrode contains a precious metal active with the detection object gas and oxygen.
(13) The electrode-coating layer covering at least one of the sensing electrode, the reference electrode and the oxygen-sensing electrode contains a precious metal inactive with the detection object gas but active with oxygen.
(14) The electrode underlayer is made of a zirconia solid electrolyte containing at least one selected from the group consisting of yttria, ceria, magnesia and scandia as a stabilizer.
(15) The sensing electrode is made of a metal oxide and/or a precious metal active with a detection object gas and oxygen.
(16) The detection object gas is any of nitrogen oxides, hydrocarbon, carbon monoxide or ammonia.

The first gas-detecting device of the present invention comprises (a) a gas-measuring chamber defined by first and second oxygen-ion-conductive solid electrolyte substrates disposed with a predetermined gap; (b) a gas inlet so that a detection gas flows into the gas-measuring chamber with a predetermined gas diffusion resistance; (c) a gas-detecting element comprising a sensing electrode fixed onto the first solid electrolyte substrate such that it is exposed to an atmosphere in the gas-measuring chamber, and active with a detection object gas and oxygen, and a reference electrode fixed onto the first solid electrolyte substrate and active with at least oxygen; (d) a detection-object-gas-converting pump element comprising (i) a detection-object-gas-converting electrode fixed onto the second solid electrolyte substrate such that it is exposed to an atmosphere in the gas-measuring chamber, and active with a detection object gas and oxygen, and (ii) a detection-object-gas-converting counter electrode fixed onto the second solid electrolyte substrate such that it is exposed to an atmosphere containing oxygen and/or an oxide gas, and active with oxygen, which can select the oxidation or reduction of a detection object gas depending on conditions; (e) a means for measuring the potential difference between the sensing electrode and the reference electrode; and (f) a voltage-applying means for driving the conversion pump element, to detect the potential difference between the sensing electrode and the reference electrode while applying predetermined voltage to the conversion pump element, thereby determining the concentration of the detection object gas in the detection gas, wherein the sensing electrode being covered by an electrode-coating layer made of an oxygen-ion-conductive solid electrolyte, and the electrode-coating layer having a portion bonded to the first solid electrolyte substrate directly or via an electrode underlayer made of an oxygen-ion-conductive solid electrolyte.

The detection object gas suitable for the above gas-detecting device is NOx.

The second gas-detecting device of the present invention comprises (a) a gas-measuring chamber defined by first and second oxygen-ion-conductive solid electrolyte substrates disposed with a predetermined gap; (b) a gas inlet provided in the gas-measuring chamber such that a detection gas flows into the gas-measuring chamber with a predetermined gas diffusion resistance; (c) a gas-detecting element comprising a sensing electrode fixed onto the first solid electrolyte substrate such that it is exposed to an atmosphere in the gas-measuring chamber, and active with a detection object gas and oxygen, and a reference electrode fixed onto the first solid electrolyte substrate and active with at least oxygen; and (d) a detection-object-gas-converting pump element comprising (i) a detection-object-gas-converting electrode fixed onto the second solid electrolyte substrate such that it is exposed to an atmosphere in the gas-measuring chamber, and active with a detection object gas and oxygen, (ii) a detection-object-gas-converting counter electrode fixed onto the second solid electrolyte substrate such that it is exposed to an atmosphere containing oxygen and/or an oxide gas, and active with oxygen, which can select the oxidation or reduction of a detection object gas depending on conditions; (e) a means for measuring the potential difference between the sensing electrode and the reference electrode; and (f) a voltage-applying means for driving the conversion pump element, thereby detecting the potential difference between the sensing electrode and the reference electrode while applying predetermined voltage to the conversion pump element, to determine the concentration of the detection object gas in the detection gas; the electrode for converting the detection object gas being covered by an electrode-coating layer made of an oxygen-ion-conductive solid electrolyte, through which the detection object gas can reach to the electrode; and the electrode-coating layer having a portion bonded to the second solid electrolyte substrate directly or via an electrode underlayer made of a solid electrolyte.

Preferred examples of the gas-detecting device of the present invention are as follows:

(1) The electrode-coating layer covering the detection-object-gas-converting electrode is preferably in such a form that a detection gas can reach a three-phase interface of the solid electrolyte substrate, the electrode underlayer or the electrode-coating layer and each electrode.

(2) The electrode-coating layer is constituted by a porous solid electrolyte film layer having pores through which the detection object gas can be diffused, the porous solid electrolyte film layer having a porosity of 10–50% and an average thickness of 3–20 $\mu$m.

(3) The electrode-coating layer covering the detection-object-gas-converting electrode is made of a zirconia solid electrolyte containing as a stabilizer at least one selected from the group consisting of yttria, ceria, magnesia and scandia.

(4) The electrode-coating layer covering the detection-object-gas-converting electrode comprises (a) at least one precious metal selected from the group consisting of platinum, rhodium, iridium, gold and alloys containing these metals, and/or (b) at least one metal oxide selected from the group consisting of $Cr_2O_3$, NiO, $NiCr_2O_4$, $MgCr_2O_4$ and $FeCr_2O_4$ in a range of 1–50% by volume based on 100% by volume of the solid electrolyte.

(5) The electrode underlayer is made of a zirconia solid electrolyte containing as a stabilizer at least one selected from the group consisting of yttria, ceria, magnesia and scandia.

(6) Said electrode underlayer comprises (a) at least one precious metal selected from the group consisting of platinum, rhodium, iridium, gold and alloys containing these metals, and/or (b) at least one metal oxide selected from the group consisting of $Cr_2O_3$, NiO, $NiCr_2O_4$, $MgCr_2O_4$ and $FeCr_2O_4$ in a range of 0.1–20% by volume based on 100% by volume of the solid electrolyte.

(7) The detection-object-gas-converting electrode is made of at least one precious metal selected from the group consisting of platinum, rhodium, iridium, gold and alloys containing these metals.

(8) The detection-object-gas-converting electrode and a layer for coating this electrode are made of a zirconia solid electrolyte containing the same stabilizer, the stabilizer being at least one selected from the group consisting of yttria, ceria, magnesia and scandia.

(9) The gas-detecting device further comprises a means for heating at least the gas-detecting element and the detection-object-gas-converting pump element to a predetermined temperature.

(10) The detection object gas is any of a nitrogen oxide gas, a hydrocarbon gas, a carbon monoxide gas and an ammonia gas.

(11) The detection object gas is nitrogen oxide, and the oxidation reaction of NO to $NO_2$ or the reduction reaction of $NO_2$ to NO in the detection gas by the conversion pump element can be selected depending on conditions.

(12) The above gas-detecting element is the gas-detecting element of the present invention.

(13) When the concentration of a reducing detection object gas is measured by the gas-detecting device of the present invention, at least a sensing electrode is exposed to an atmosphere containing 0.1% by volume or more of oxygen, to measure potential difference between the sensing electrode and the reference electrode.

The electrode-coating layer prevents the direct contact of the conversion electrode with a detection gas. By driving a conversion pump element and/or a gas-treating pump element, oxygen is pumped into the gas-measuring chamber, in which a reducing gas in the detection gas can be oxidized. Particularly in the case of driving with a conversion electrode of a conversion pump element as an anode, the formation of the electrode-coating layer increases oxidation efficiently of a reducing gas by oxygen pumped from the conversion electrode. Accordingly, a detection gas containing a high concentration of a reducing gas is not directly contacted with the conversion electrode, thereby suppressing the remarkable change of adsorption and desorption performance of NO.

Because bonding interface between the conversion electrode and the electrode-coating layer serves as electrode interface, an electrode interface area can be drastically increased, thereby suppressing the variation of interface impedance between the conversion electrode and the solid electrolyte substrate.

DETAILED DESCRIPTION OF THE PREFERRED EMBODIMENTS

Figure 1:
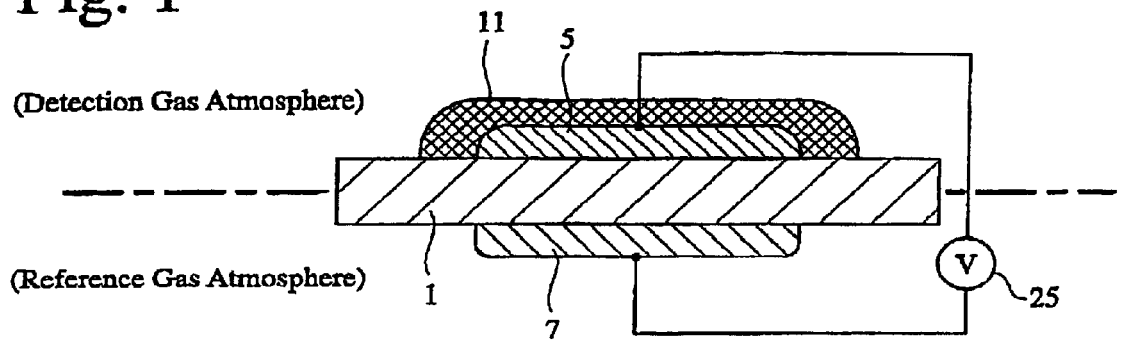
FIG. 1 is a schematic cross-sectional view showing a gas-detecting element according to one embodiment of the present invention.

[1] Gas-detecting Element
(A) One Example of Gas-detecting Element with Coated Sensing Electrode Referring to FIG. 1, the basic structure of the gas-detecting element of the present invention comprising a sensing electrode covered by an electrode-coating layer will be explained. In the gas-detecting element of the present invention shown in FIG. 1, an oxygen-ion-conductive solid electrolyte substrate 1 has one surface, on which a sensing electrode 5 active with a detection object gas and oxygen is formed, and the other surface, on which a reference electrode 7 is formed. In the present invention, the sensing electrode 5 and/or the reference electrode 7 is covered by an electrode-coating layer of an oxygen-ion-conductive solid electrolyte. The electrode-coating layer is in such a form that a detection gas can reach a three-phase interface of a solid electrolyte substrate 1, an electrode underlayer or an electrode-coating layer and each electrode. In this example, an electrode-coating layer 11 made of a porous oxygen-ion-conductive solid electrolyte is laminated on the sensing electrode 5, and the electrode-coating layer 11 has a portion bonded directly to the solid electrolyte substrate 1. Also, in this example, the sensing electrode 5 is exposed to a detection gas atmosphere, which contains a detection object gas, and the reference electrode 7 is exposed to a reference gas atmosphere, for instance, air, to obtain a constant reference potential.

When the detection object gas is NOx, reactions represented by the above formulae (1) and (2), and (3) and (4) occur simultaneously on the sensing electrode 5, generating an equilibrium potential (mixed potential) on the electrodes. Because oxygen is involved in such reactions, a detection gas, to which the sensing electrode 5 is exposed, should contain 0.1% by volume or more of oxygen. To achieve rapid gas response, the detection gas preferably contains 1% by volume or more of oxygen.

(1) Solid Electrolyte Substrate

The materials of the solid electrolyte substrate 1 are not restrictive as long as they have oxygen ion conductivity. The oxygen-ion-conductive materials are preferably zirconia solid electrolytes containing yttria ($Y_2O_3$), etc. as stabilizers for improving chemical stability and mechanical strength. When the amount of yttria added is 3–10 mol % based on the total amount of the solid electrolyte, high mechanical strength and high oxygen ion conductivity can be achieved. The preferred amount of yttria added is 5–8 mol %.

When Al is further added to a zirconia solid electrolyte containing yttria in an amount of 0.01–1 weight % based on the total amount of the solid electrolyte, the sintering temperature of the zirconia solid electrolyte is drastically decreased, thereby improving the detection performance of the resultant sensor. Because the addition of Al improves the stability of the electrode interface, the interface impedance can be decreased, resulting in increase in the activity of the electrode. The preferred amount of Al added is 0.05–0.5 weight %. When the amount of Al added is more than 1 weight %, a solid state reaction takes place between the solid electrolyte substrate 1 and the electrode-coating layer 11, resulting in decrease in the sensitivity of the gas-detecting element, and decrease in the strength of the zirconia solid electrolyte. On the other hand, when the amount of Al added is less than 0.01 weight %, there is substantially no effect of adding Al. The thickness of the solid electrolyte substrate 1 is preferably 100–300 µm.

(2) Sensing Electrode

The sensing electrode 5 should be active with oxygen and a detection object gas. The term "active" used herein means that the sensing electrode 5 generates a predetermined electrode potential when contacted with oxygen and a detection object gas. This activity may be called "electrode activity." The thickness of the sensing electrode 5 is preferably 2–15 µm.

The sensing electrode 5 may be formed by a metal oxide and/or a precious metal (hereinafter referred to as "first precious metal") active with oxygen and a detection object gas. Though the metal oxide and the first precious metal may be used alone, they are preferably used in combination to improve the performance of electrodes.

When the detection object gas is nitrogen oxides (NOx), the use of oxides of Cr as metal oxides provide the sensing electrode 5 with high activity. Particularly when at least one selected from the group consisting of $NiCr_2O_4$, $FeCr_2O_4$, $MgCr_2O_4$ and $Cr_2O_3$ is used, it is possible to provide the sensing electrode 5 with high activity to NOx and high stability. Because these metal oxides are essentially poor in sinterability with small sintering shrinkage, strain is likely to be generated between the resultant sintered body and the solid electrolyte substrate 1. As described later, solid electrolyte green sheets are used for the solid electrolyte substrates 1 in the laminate-type NOx sensors shown in FIGS. 14–19, resulting in extremely large strain by the sintering shrinkage. Accordingly, particularly when the sensing electrode 5 is made of a metal oxide only, the lack of the electrode-coating layer 11 tends to cause cracking and peeling during the sintering of the electrodes. In the first embodiment of the present invention, by providing an electrode-coating layer 11 made of a solid electrolyte for functioning to suppress physical strain on a surface of a sensing electrode 5, the bonding stability of the sensing electrode 5 to the solid electrolyte substrate 1 can be improved, thereby improving the stability of the sensing electrode 5.

When the detection object gas is nitrogen oxides (NOx), the use of the first precious metal also provides the sensing electrode 5 with high activity. The first precious metal is at least one selected from the group consisting of Rh, Ir, Au and precious metal alloys comprising these metals. Among the above precious metal alloys, a Pt—Rh alloy is an alloy of Pt, which is a precious metal inactive with NOx but active with oxygen (hereinafter referred to as "second precious metal"), and Rh which is a first precious metal active with both of NOx and oxygen, exhibiting high sensitivity to NOx and high sensitivity stability.

The sensing electrode 5 preferably further contains an oxygen-ion-conductive solid electrolyte. Because this increases an electrode interface and decreases electrode impedance, more stable sensor output can be obtained. The solid electrolytes added to the sensing electrode 5 are preferably the same zirconia solid electrolytes used as the solid electrolyte substrate 1, the electrode-coating layer 11 and the electrode underlayer 31 described later. It is preferable to add at least one selected from the group consisting of magnesia (MgO), ceria ($CeO_2$), scandia ($Sc_2O_3$) and yttria ($Y_2O_3$) as a stabilizer to the zirconia solid electrolyte. The stabilizer is preferably the same as the stabilizer contained in a zirconia solid electrolyte constituting any of the solid electrolyte substrate 1, the electrode-coating layer 11 and the electrode underlayer 31, more preferably the same as the stabilizer contained in zirconia solid electrolyte used for the electrode-coating layer 11.

The amount of the solid electrolyte added is preferably 5–25% by mass, more preferably 10–20% by mass, based on the total amount of the sensing electrode 5. When the amount of the solid electrolyte added is less than 5% by mass, there is no sufficient effect of adding the solid electrolyte. On the other hand, when the amount of the solid electrolyte added exceeds 25% by mass, the sensitivity of the gas-detecting element decreases.

(3) Electrode-coating Layer

The electrode-coating layer 11 covering the sensing electrode 5 is bonded to the solid electrolyte substrate 1 directly or via an electrode underlayer of an oxygen-ion-conductive solid electrolyte. The electrode-coating layer 11 should be in such a form that a detection gas can reach a three-phase interface of the solid electrolyte substrate 1, the electrode underlayer or the electrode-coating layer 11 (all constituted by an oxygen-ion-conductive solid electrolyte) and the sensing electrode 5. In order that the detection object gas can reach the three-phase interface, the electrode-coating layer 11 is preferably porous. In addition, the electrode-coating layer 11 covering the sensing electrode 5 may be a dense layer in such a form that part of side surface of the sensing electrode 5 is exposed.

The porosity of the electrode-coating layer 11 is preferably 10–50%. When the porosity is less than 10%, it takes too much time for the detection object gas to reach the sensing electrode 5, resulting in an elongated gas response time. On the other hand, when the porosity is more than 50%, the electrode-coating layer 11 has low strength, failing to mechanically suppress strain between the sensing electrode 5 and the solid electrolyte substrate 1. As a result, the interface between them tends to become unstable by thermal stress caused by the difference in a thermal expansion coefficient between the sensing electrode 5 and the solid electrolyte substrate 1 at the time of detecting a gas, failing to obtain a stable detection output. The more preferred porosity of the electrode-coating layer 11 is 25–50%.

The thickness of the electrode-coating layer 11 is important to improve bonding stability between the solid electrolyte substrate 1 and the sensing electrode 5. When the electrode-coating layer 11 is constituted by a porous solid electrolyte, its average thickness is preferably 3–20 μm. When the thickness of the electrode-coating layer 11 is less than 3 μm, the electrode-coating layer 11 per se has too low strength. On the other hand, when the thickness of the electrode-coating layer 11 is more than 20 μm, it takes too much time for the detection object gas to diffuse to the sensing electrode 5, resulting in an elongated gas response time.

It is preferable to use an oxygen-ion-conductive zirconia solid electrolyte for the electrode-coating layer 11 from the aspect of stability or cost reduction. This zirconia solid electrolyte contains at least one selected from the group consisting of yttria ($Y_2O_3$), ceria ($CeO_2$), magnesia (MgO) and scandia ($Sc_2O_3$) as a stabilizer from the aspect of sensor performance.

The amount of the stabilizer added is preferably 3–20 mol %, more preferably 5–20 mol %, particularly 5–15 mol %, based on the total amount of the solid electrolyte. When the amount of the stabilizer added is less than 3 mol %, the solid electrolyte has insufficient oxygen ion conductivity, resulting in a decreased sensor output. On the other hand, when the amount of the stabilizer added exceeds 20 mol %, the strength of the electrode-coating layer 11 decreases, resulting in decrease in stability and increase in the fluctuation of output. The stabilizer added is preferably uniformly dispersed in zirconia and completely dissolved in a solid phase thereof, though a trace amount of the stabilizer may microscopically remain in grain boundaries, etc. without affecting the effects of the present invention.

The first precious metal active with a detection object gas and oxygen may be added to the electrode-coating layer 11. For instance, when NOx is a detection object, it is preferable to add as the first precious metal at least one selected from the group consisting of Au, Ir and Rh to the electrode-coating layer 11. This improves the physical and chemical bonding of the sensing electrode 5 to the solid electrolyte substrate 1, so that resistance in the electrode interface can be reduced. Further, the stability of the electrode interface is so improved that the drift of sensor output can drastically be reduced. The amount of the first precious metal added to the electrode-coating layer 11 is preferably 0.1–30% by mass, more preferably 1–20% by mass, based on the total amount of the electrode-coating layer 11, to achieve stable electrode performance. When the amount of the first precious metal added is less than 0.1% by mass, its addition effect cannot sufficiently be obtained. On the other hand, when the amount of the first precious metal added is more than 30% by mass, the ion conductivity of the electrode-coating layer 11 decreases.

The second precious metal inactive with a detection object gas and active with oxygen may be added to the electrode-coating layer 11. When the detection object is, for instance, NOx, the second precious metal is preferably at least one selected from the group consisting of Pt, Pd and Ru to obtain a stable electrode performance. When the second precious metal alone is added to the electrode-coating layer 11, its amount is preferably 0.05–4% by mass, more preferably 0.1–2% by mass. When the amount of the second precious metal added is less than 0.05% by mass, there is no sufficient effect of adding the second precious metal. On the other hand, when the amount of the second precious metal added exceeds 4% by mass, the sensor output decreases.

Both the first and second precious metals can be added to the electrode-coating layer 11. In this case, the amount of the first precious metal added is preferably 0.1–20% by mass, more preferably 1–15% by mass, and the amount of the second precious metal added is preferably 0.05–4% by mass, more preferably 0.1–2% by mass.

(4) Reference Electrode

The reference electrode 7 is opposing the sensing electrode 5 via the solid electrolyte substrate 1 in a reference atmosphere (air) separated from the detection gas. Such structure is necessary to isolate the reference electrode 7 from the detection gas atmosphere, when the reference electrode 7 has activity with the detection object gas (for instance, NOx). When the reference electrode 7 is active with the detection object gas, the solid electrolyte substrate 1 should be made of a material through which the detection object gas cannot be diffused. On the other hand, when the reference electrode 7 is made of a material inactive with a detection object gas, the reference electrode 7 may be exposed to a detection gas atmosphere. In this case, other structures than shown in FIG. 1 are possible: the sensing electrode 5 and the reference electrode 7 may be disposed on the same surface of the solid electrolyte substrate 1 (see FIGS. 6–8). The reference electrode 7 should be active with at least oxygen and preferably has the same oxygen activity as that of the sensing electrode 5. When the reference electrode 7 is inactive with the detection object gas, the solid electrolyte substrate 1 may be porous so that the detection object gas can be diffused.

In the case of detecting NOx, the constituent material for the reference electrode 7 inactive with the detection object gas and active with oxygen is preferably Pt. The term "inactive with" used herein means that the potential of an electrode is sufficiently lower than that of the sensing electrode 5 in the same concentration of a detection object gas (for instance, NOx). The thickness of the reference electrode 7 is preferably 3–10 $\mu$m. Incidentally, though the electrode-coating layer 11 is formed only on the sensing electrode 5 in FIG. 1, the electrode-coating layer 11 may also be formed on the reference electrode 7 described later.

(5) Other Constituents

The sensing electrode 5 and the reference electrode 7 are connected via lead conductors provided with a potentiometer 25, whereby potential difference between the sensing electrode 5 and the reference electrode 7 can be measured. The potentiometer 25 may be a usual voltmeter (circuit). Because current is taken out to a measurement system by the voltmeter 25, the voltmeter 25 preferably has sufficiently larger input impedance than electrode impedance to achieve precise sensor output.

There is a method without using a voltmeter to measure potential difference between the sensing electrode 5 and the reference electrode 7. For instance, the detection element is connected to comparison cells (battery) in parallel, to measure the voltage of the comparison cells, at which no current flows between the two cells. In this method, it is possible to measure the electromotive force of a sensor even though no current is taken out from the detection element at all. Both the sensing electrode 5 and the reference electrode 7 are preferably provided with electric current collectors (conductor leads, not shown) made of Pt, etc. The collector may be formed on either a bottom or upper surface of the sensing electrode 5 and the reference electrode 7.

To achieve high ion conductivity, at least the sensing electrode 5 and the solid electrolyte 11 are preferably heated at a predetermined temperature. Specifically, in the case of zirconia solid electrolyte, they are preferably held at a temperature of 300–400° C. or higher, at which ion conductivity increases. A means for heating the sensing electrode 5 and the solid electrolyte 11 may be an external heat source or a self-heating-type heater integrated into the gas-detecting element.

(B) Modifications of Gas-detecting Element with Coated Sensing Electrode

Figure 2:
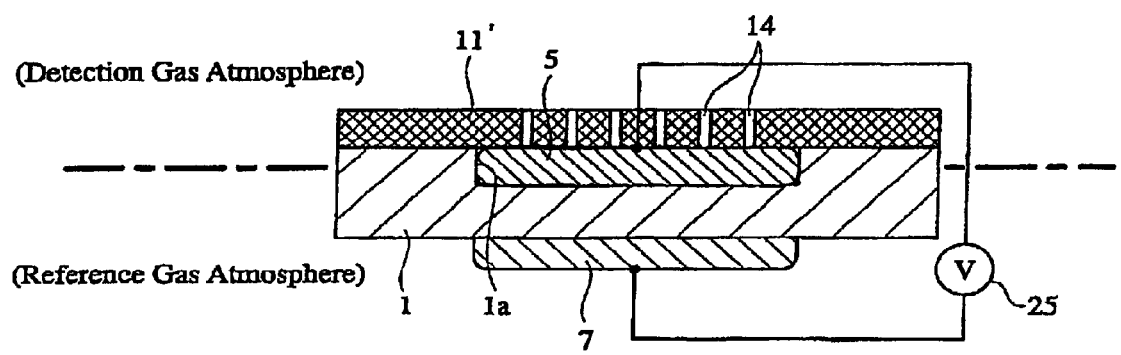
FIG. 2 is a schematic cross-sectional view showing a gas-detecting element according to another embodiment of the present invention.

FIG. 2 is a schematic cross-sectional view showing another example of the gas-detecting element of the present invention. In FIG. 2, the same reference numerals are assigned to parts operating substantially in the same manner as in FIG. 1. In the structure shown in FIG. 2, a sensing electrode 5 is fixed in a recess 1$a$ formed in a solid electrolyte substrate 1, and the sensing electrode 5 is covered by an electrode-coating layer 11' having gas-diffusing pores 14 such that a detection object gas can be diffused to the sensing electrode 5. The electrode-coating layer 11' is directly bonded to the solid electrolyte substrate 1 in a region other than the sensing electrode 5. Each gas-diffusing pore 14 of the electrode-coating layer 11' has a diameter of preferably 10–1000 82 m, more preferably 100–500 $\mu$m.

A ratio (Sh/Se) of the total opening area (Sh) of the gas-diffusing pores to the area Se of the sensing electrode 5 is preferably 0.05–0.28, more preferably 0.12–0.28. The thickness of the electrode-coating layer 11' having such gas-diffusing pores 14 is 5–100 $\mu$m, more preferably 30–70 $\mu$m. When the thickness of the electrode-coating layer 11' is less than 5 $\mu$m, there is insufficient coating effect. On the other hand, when the thickness of the electrode-coating layer 11' exceeds 100 $\mu$m, there is long diffusion time for the detection object gas to reach the sensing electrode 5, resulting in slow detection response. Incidentally, because the electrode-coating layer 11' having gas-diffusing pores 14 has sufficient gas diffusion characteristics, it need not be porous.

Of course, in the detection element having a structure in which the sensing electrode 5 is fixed in the recess 1$a$ as shown in FIG. 2, too, the gas-diffusing pores 14 may not be formed if the electrode-coating layer 11' is porous. The electrode-coating layer 11' having gas-diffusing pores 14 may be made of the same material as described above with respect to the electrode-coating layer 11 shown in FIG. 1.

Figure 3:
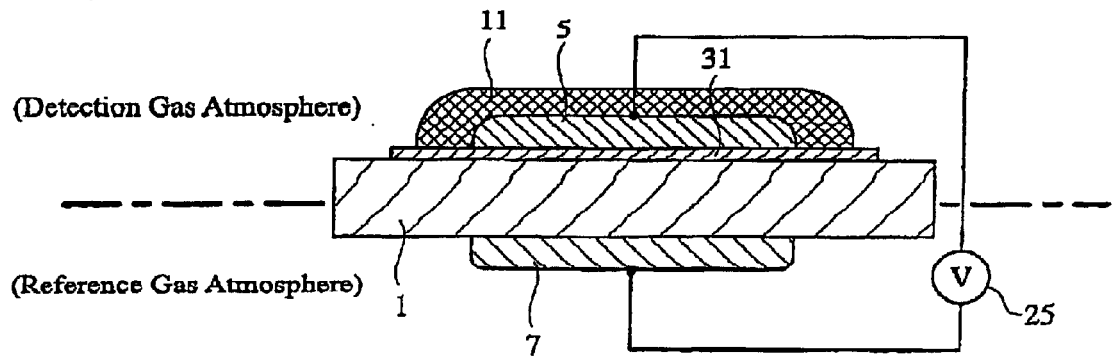
FIG. 3 is a schematic cross-sectional view showing a gas-detecting element according to a further embodiment of the present invention.

FIG. 3 is a schematic cross-sectional view showing another example of the gas-detecting element. In FIG. 3, the same reference numerals are assigned to parts operating substantially in the same manner as in FIG. 1. In this embodiment, an electrode underlayer 31 made of an oxygen-ion-conductive solid electrolyte is formed between the sensing electrode 5 and the solid electrolyte substrate 1. The electrode underlayer 31 is preferably made of the same oxygen-ion-conductive solid electrolyte as that of the electrode-coating layer 11, and porous like the electrode-coating layer 11 from the aspect of gas response.

As shown in FIG. 3, the electrode underlayer 31 may be formed between the electrode-coating layer 11 and the solid electrolyte substrate 1. In this case, though the electrode-coating layer 11 is not directly bonded to the solid electrolyte substrate 1, it is bonded to the solid electrolyte substrate 1 via the solid electrolyte electrode underlayer 31 electrically connected thereto. Accordingly, substantially the same effect can be obtained as in a case where it is directly bonded to the solid electrolyte substrate 1. In such a structure, even if the sensing electrode 5 is made of a material that is likely to generate strain when the sensing electrode 5 is directly bonded to the solid electrolyte substrate 1, stable electrode interface can be formed. In addition, a synergistic effect with the strain-suppressing function of the electrode-coating layer 11 provides the electrode interface with further excellent stability. The electrode underlayer 31 is a dense or porous layer having a thickness of about 3 to 10 μm.

Figure 4:
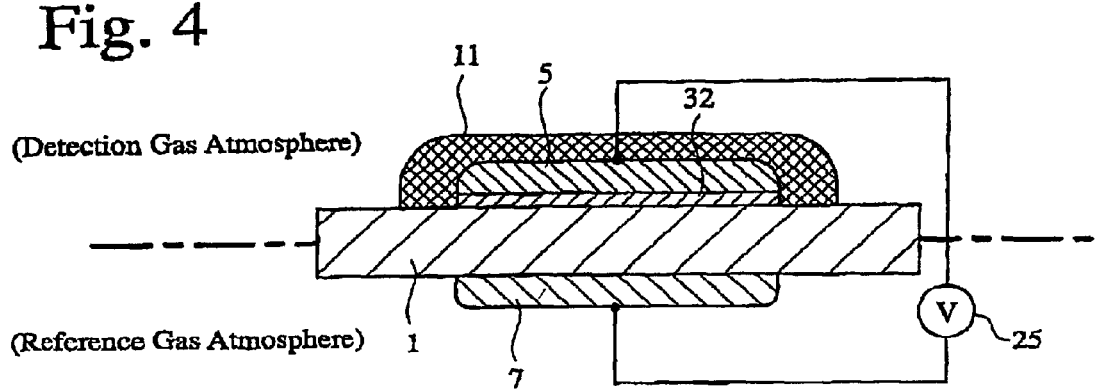
FIG. 4 is a schematic cross-sectional view showing a gas-detecting element according to a still further embodiment of the present invention.

FIG. 4 is a schematic cross-sectional view showing a still further example of the gas-detecting element. In FIG. 4, the same reference numerals are assigned to parts operating substantially in the same manner as in FIG. 1. An electric insulating layer 32 is formed between the sensing electrode 5 and the solid electrolyte substrate 1. The electrode-coating layer 11 laminated on a surface of the sensing electrode 5 has a portion bonded directly to the solid electrolyte substrate 1. With the electric insulating layer 32, an electrode reaction at the sensing electrode 5 predominantly takes place in bonding interface with the electrode-coating layer 11. Accordingly, a detection object gas can be detected immediately after it reaches a surface of the sensing electrode 5, resulting in excellent gas response.

Figure 5:
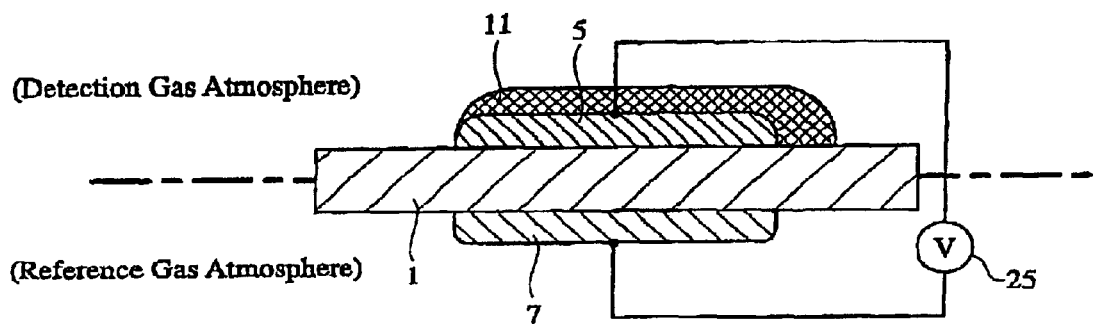
FIG. 5 is a schematic cross-sectional view showing a gas-detecting element according to a still further embodiment of the present invention.

FIG. 5 shows a gas-detecting element having basically the same structure as in FIG. 1, though it is not that an entire surface of a sensing electrode 5 is covered by an electrode-coating layer 11 as shown in FIG. 1, but that it has a portion not covered by the electrode-coating layer 11 in part of its side surface. In this structure, because a detection gas can be diffused from a side surface of the electrode to a detection part thereof, the electrode-coating layer 11 need not be porous but be a dense layer. The term "dense layer" used herein a layer having porosity of 0.5% or less. By covering a surface of a sensing electrode 5 with a dense electrode-coating layer 11, the effect of isolating the sensing electrode 5 from foreign contamination components is remarkably improved. To exhibit the above effect sufficiently, the dense electrode-coating layer 11 preferably has an average thickness of 1–10 μm.

Figure 6:
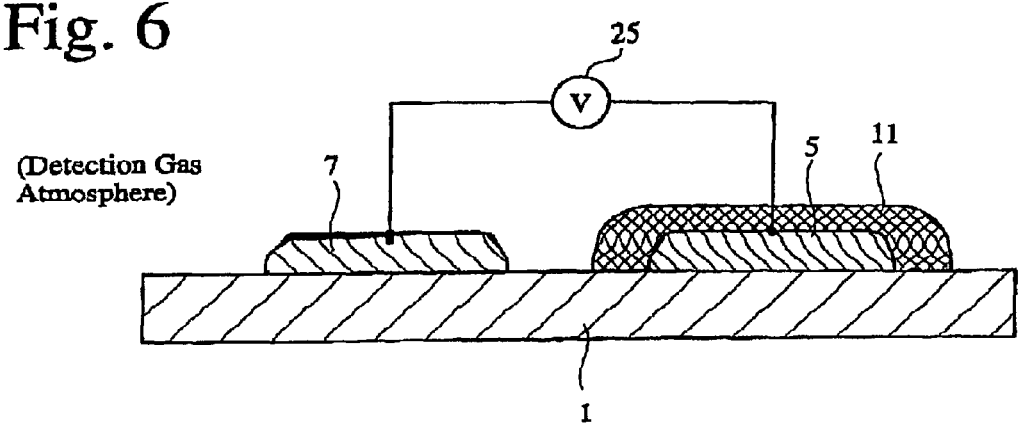
FIG. 6 is a schematic cross-sectional view showing a gas-detecting element according to a still further embodiment of the present invention.
Figure 7:
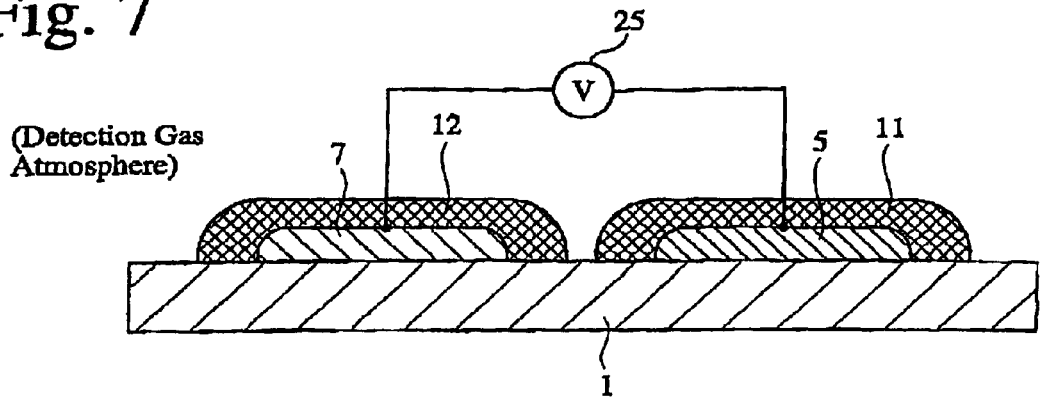
FIG. 7 is a schematic cross-sectional view showing a gas-detecting element according to a still further embodiment of the present invention.
Figure 8:
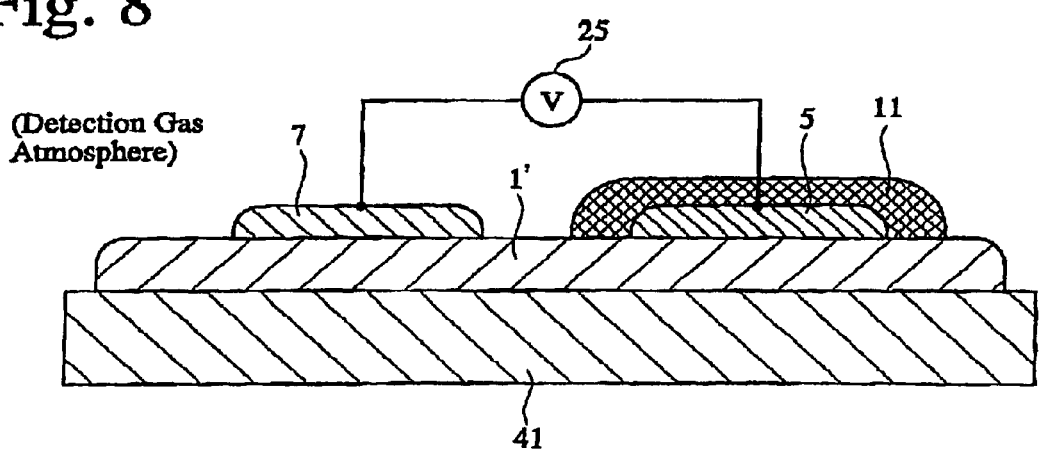
FIG. 8 is a schematic cross-sectional view showing a gas-detecting element according to a still further embodiment of the present invention.

FIGS. 6–8 are schematic cross-sectional views showing still further examples of the gas-detecting elements. In FIGS. 6–8, the same reference numerals are assigned to parts operating substantially in the same manner as in FIG. 1. Each of the gas-detecting elements shown in FIGS. 6–8 has a structure in which the sensing electrode 5 and the reference electrode 7 are disposed on the same surface of the solid electrolyte substrate 1. In such structure, because the sensing electrode 5 and the reference electrode 7 are exposed to a detection gas atmosphere simultaneously, the reference electrode 7 should be inactive with at least a detection object gas. In the gas-detecting element shown in FIG. 7, electrode-coating layers 11, 12 are formed on the sensing electrode 5 and the reference electrode 7, respectively. The function of the electrode-coating layer 12 on the reference electrode 7 will be described later referring to FIG. 11.

When the sensing electrode 5 and the reference electrode 7 are disposed on the same surface of the solid electrolyte substrate 1, as shown in FIG. 8, an electric insulating substrate 41 is laminated with the solid electrolyte substrate film layer 1' and then with the sensing electrode 5 and the reference electrode 7.

Figure 9:
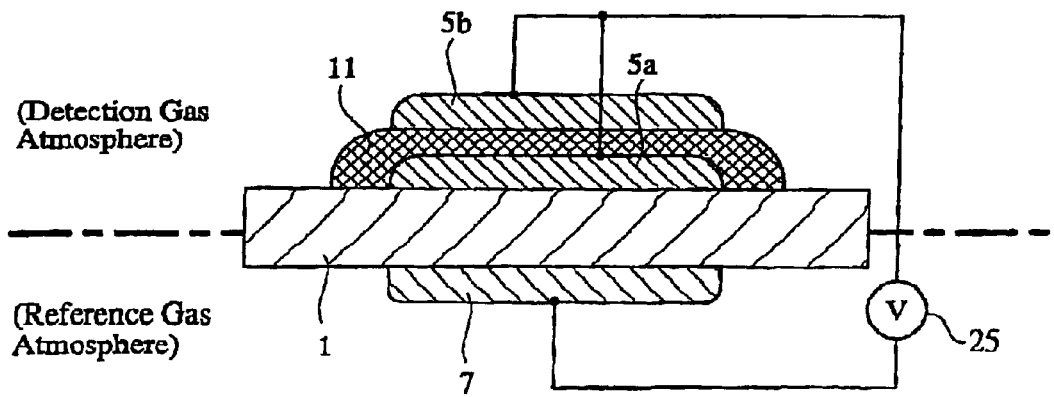
FIG. 9 is a schematic cross-sectional view showing a gas-detecting element according to a still further embodiment of the present invention.
Figure 10:
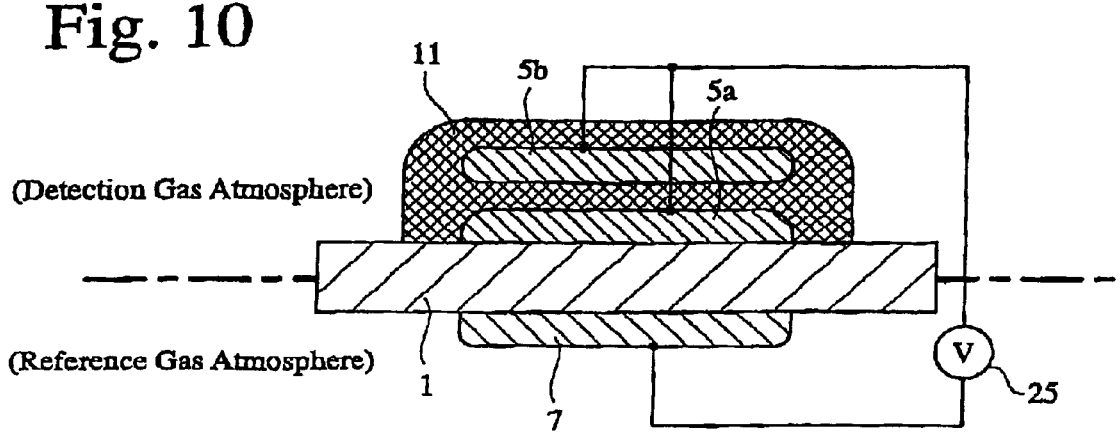
FIG. 10 is a schematic cross-sectional view showing a gas-detecting element according to a still further embodiment of the present invention.

FIGS. 9 and 10 are schematic cross-sectional views showing still further examples of the gas-detecting elements. In FIGS. 9 and 10, the same reference numerals are assigned to parts operating substantially in the same manner as in FIG. 1. FIGS. 9 and 10 show structures in which two sensing electrodes 5a, 5b (hereinafter referred to as "first sensing electrode" and "second sensing electrode," respectively) are disposed via an electrode-coating layer 11.

In the structure shown in FIG. 9, the first sensing electrode 5a is directly fixed onto the solid electrolyte substrate 1 and covered by the electrode-coating layer 11, and the second sensing electrode 5b is fixed onto the electrode-coating layer 11. In the structure shown in FIG. 10, the first sensing electrode 5a is directly fixed onto the solid electrolyte substrate 1 and covered by the electrode-coating layer 11, and the second sensing electrode 5b is embedded in the electrode-coating layer 11 at a position above the first sensing electrode 5a. Though the first sensing electrode 5a and the second sensing electrode 5b are separated from each other with a certain gap in the illustrated example, they may be in partial contact with each other. Thus, a sensing electrode composed of the sensing electrodes 5a and 5b has a wider electrode interface area, resulting in decreased electrode impedance.

The gas-detecting element having the structure shown in FIG. 10 exhibits excellent gas response, because an electrode reaction on the first and second sensing electrodes 5a, 5b takes place predominantly in a bonding interface with the electrode-coating layer 11. Of course, in addition to the structures shown in FIGS. 9 and 10, for instance, three or more sensing electrodes may be formed, and the arrangement of these electrodes is not particularly restrictive as long as it is inside or on the electrode-coating layer 11. Incidentally, any of the first sensing electrode 5a and the second sensing electrode 5b may be formed by the same material as that of the above sensing electrode 5. This is true when three or more sensing electrodes are formed.

(C) One Example of Gas-detecting Element with Coated Reference Electrode

Figure 11:
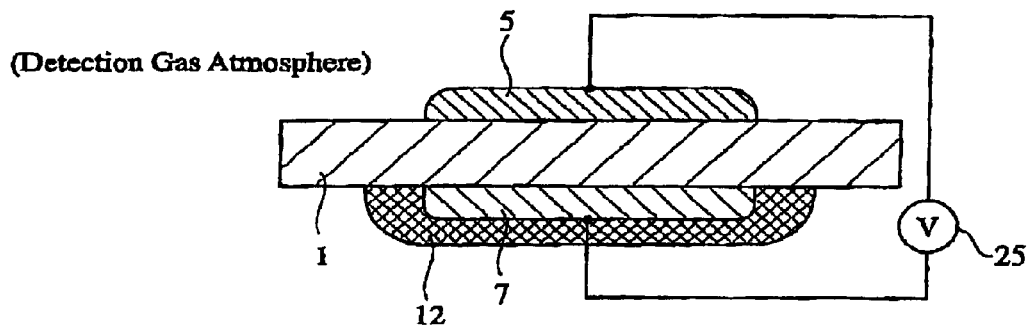
FIG. 11 is a schematic cross-sectional view showing a gas-detecting element according to a still further embodiment of the present invention.

The basic structure of the gas-detecting element of the present invention in which a reference electrode is covered by an electrode-coating layer will be explained. FIG. 11 is a schematic cross-sectional view showing one example of a gas-detecting element with a coated reference electrode. The structure of this gas-detecting element is basically the same as shown in FIG. 1, except that the reference electrode 7, in place of the sensing electrode 5, is covered by an electrode-coating layer 12, and that the reference electrode 7 is also exposed to a detection gas atmosphere. Formed on an oxygen-ion-conductive solid electrolyte substrate 1 are a sensing electrode 5 active with a detection object gas and oxygen on one surface and a reference electrode 7 on the other surface.

The porous, oxygen-ion-conductive, electrode-coating layer 12 is laminated on the reference electrode 7, such that the electrode-coating layer 12 is directly in contact with the solid electrolyte substrate 1. By direct contact with the solid electrolyte substrate 1, the electrode-coating layer 12 also functions as the solid electrolyte substrate 1 of the reference electrode 7, whereby the electrode interface impedance of the reference electrode 7 can be reduced. Accordingly, the electrode reaction speed increases, resulting in improvement in stability.

Though the electrode-coating layer 12 is directly bonded to the solid electrolyte substrate 1 in the example of FIG. 11, the same effect can also be obtained by bonding via the electrode underlayer 31 made of an oxygen-ion-conductive solid electrolyte as in the electrode-coating layer 11 shown in FIG. 3. Though the sensing electrode 5 is not covered by the electrode-coating layer 12 in the structure shown in FIG. 11, of course, both of the sensing electrode 5 and the reference electrode 7 may be covered by the electrode-coating layer 12. The sensing electrode 5 and the reference electrode 7 are connected via lead conductors provided with a potentiometer 25, thereby making it possible to measure potential difference between the sensing electrode 5 and the reference electrode 7.

(D) Modifications of Gas-detecting Element with Coated Reference Electrode

Figure 12:
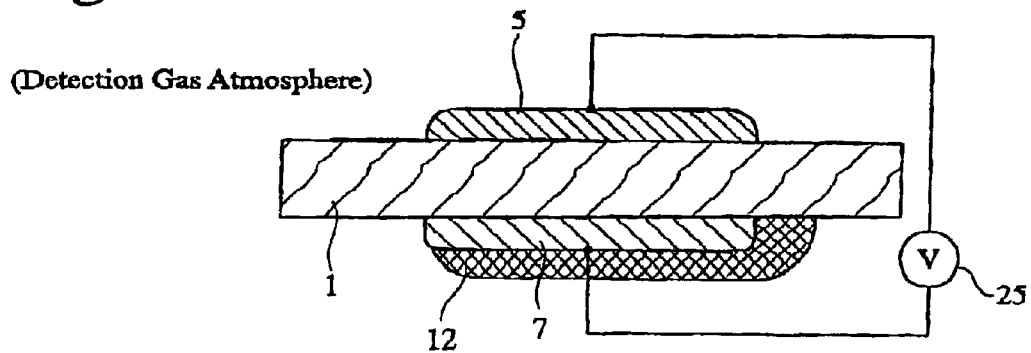
FIG. 12 is a schematic cross-sectional view showing a gas-detecting element according to a still further embodiment of the present invention.

FIG. 12 shows a gas-detecting element having basically the same structure as shown in FIG. 11, except that it is not that an entire surface of the reference electrode 7 is covered by an electrode-coating layer 12 like in FIG. 11, but that part of a side surface of the electrode has a portion not covered by the electrode-coating layer 12. With this structure, a detection gas can be diffused from a side surface of the electrode to its detection part. Thus, it is not necessary to make the electrode-coating layer 12 porous, but it may be a dense layer. Thus, by covering a surface of the reference electrode 7 with a dense electrode-coating layer 12, the effect of preventing foreign contamination components from coming into contact with the reference electrode 7 is remarkably improved. As a result, it becomes easier to constitute a reference electrode active only with oxygen without generating activity with a detection object gas.

Further, because the electrode-coating layer 12 has a portion with which it is brought into direct contact with the solid electrolyte substrate 1, impedance reduction effect can also be obtained as described above. Though the side surface of the electrode acts as a gas inlet in FIG. 12, the same effect can be obtained, for instance, by providing the electrode-coating layer 12 with a diffusion opening as small as a pinhole on an upper surface of the electrode like the coating layer 11' on the sensing electrode shown in FIG. 2. In this case, however, it is necessary that the cross section area, number, etc. of the pinhole should be designed taking contamination prevention effect and response performance into consideration.

As described above, the electrode-coating layer 12 covering the reference electrode 7 exposed to a detection gas should be in a form in which a detection gas can reach a three-phase interface with the reference electrode 7 and the solid electrolyte substrate 1. In this case, if the electrode-coating layer 12 is provided with diffusion pores 14, or part of a side surface of the reference electrode 7 is exposed, it is not necessary that the electrode-coating layer 12 is constituted by a porous material. Particularly to prevent contamination during sintering or operation, it is preferable to cover an upper surface of the reference electrode 7 with a dense layer, such that part of a side surface of the electrode is exposed. To reduce interface impedance between the reference electrode 7 and the solid electrolyte substrate 1, at least part of the electrode-coating layer 12 should be bonded to the solid electrolyte substrate 1 directly or via the electrode underlayer 31 made of an oxygen-ion-conductive solid electrolyte.

The porosity of the electrode-coating layer 12 is preferably 0–50%, though it is changeable depending on its structure. When the electrode-coating layer 12 is porous, the electrode-coating layer 12 preferably has an average thickness of 1–20 $\mu$m to provide the gas-detecting element with good performance. On the other hand, when the electrode-coating layer 12 is a dense layer, its average thickness is preferably 1–10 $\mu$m to obtain sufficient effect.

The electrode-coating layer 12 covering the reference electrode 7 is preferably made of the same oxygen-ion-conductive zirconia solid electrolyte as that of the electrode-coating layer 11 covering the sensing electrode 5. The electrode-coating layer 12 may contain the second precious metal inactive with a detection object gas and active with oxygen. For instance, when the detection object is NOx, the second precious metal is preferably at least one selected from the group consisting of Pt, Pd and Ru to provide stable electrode performance. The amount of the second precious metal added is preferably 0.05–4% by mass, more preferably 0.1–2% by mass, based on the total amount of the electrode-coating layer 12. When the amount of the second precious metal added is less than 0.05% by mass, there is no sufficient effect of adding the second precious metal. On the other hand, when the amount of the second precious metal added exceeds 4% by mass, there is substantially no further improvement in the effect, resulting only in increase in the product cost.

The reference electrode 7 need only be made of an electrode material active with oxygen. Particularly in a structure in which the reference electrode 7 is also disposed in a detection gas atmosphere, it is preferably made of an electrode material inactive with a detection object gas and active only with oxygen. When the detection object gas is NOx, a material comprising at least one selected from the group consisting of platinum, iridium and gold is preferable because of its relatively low electrode potential to NOx. Particularly the reference electrode made of platinum and iridium has low electrode potential to NOx, thereby making it possible to reduce the impedance of the electrode per se.

The reference electrode also preferably contains an oxygen-ion-conductive solid electrolyte. The solid electrolyte added to the reference electrode is preferably a zirconia solid electrolyte. In this case, it is more possible to add as a stabilizer at least one selected from the group consisting of magnesia, ceria, scandia and yttria. When the stabilizer added to a solid electrolyte for the electrode-coating layer 12 is the same as added to a solid electrolyte for the reference electrode 7, better effect can be obtained.

Though the structure in which the reference electrode 7 and the sensing electrode 5 are exposed to the same detection gas has been explained above, the reference electrode 7 can also be covered by the electrode-coating layer 12 in the structure in which it is exposed to a reference gas such as air, etc. In this case, the prevention of contamination need not be considered, but improvement in the bonding stability of interface between the solid electrolyte substrate 1 and the reference electrode 7 and gas response need only be considered in the construction of the electrode-coating layer 12.

(E) Gas-detecting Element with Coated Oxygen-sensing Electrode

Figure 13:
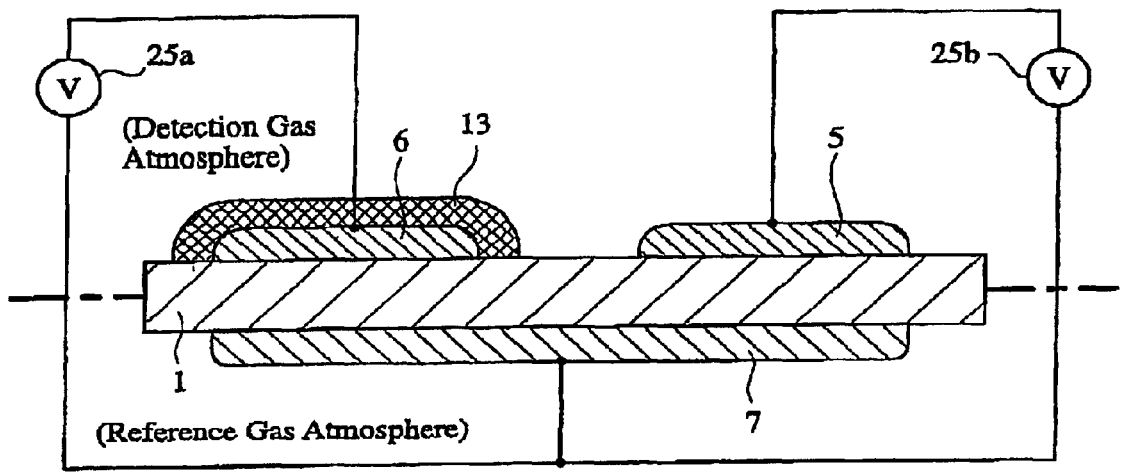
FIG. 13 is a schematic cross-sectional view showing a gas-detecting element according to a still further embodiment of the present invention.

FIG. 13 shows the structure of the gas-detecting element of the present invention, in which an oxygen-sensing electrode is covered by an electrode-coating layer. In this gas-detecting element, a sensing electrode 5 and an oxygen-sensing electrode 6 are disposed on the same surface of the solid electrolyte substrate 1, and a reference electrode 7 is disposed on the opposite surface of the solid electrolyte substrate 1 such that it is opposing the sensing electrode 5 and the oxygen-sensing electrode 6 via the solid electrolyte substrate 1. The reference electrode 7 is in a reference gas atmosphere separated from the detection object gas. The oxygen-sensing electrode 6 is covered by an electrode-coating layer 13 made of an oxygen-ion-conductive solid electrolyte. Such structure is effective when the oxygen-sensing electrode 6 has activity with a trace amount of the detection object gas. In this case, by isolating the reference electrode 7 from a detection gas atmosphere, the concentration of a detection object gas can be detected with high precision.

The solid electrolyte substrate 1 should be resistant to gas diffusion. The oxygen-sensing electrode 6 is preferably active at least with oxygen. The electrode-coating layer 13 covering the oxygen-sensing electrode 6 is preferably the same as the electrode-coating layer 12 covering the reference electrode 7 in shape, size, material, etc.

The oxygen-sensing electrode 6 need only be made of an electrode material active with oxygen, but it is preferably made of an electrode material inactive with a detection object gas and active only with oxygen. When the detection object gas is NOx, a material comprising at least one selected from the group consisting of platinum, iridium and gold is preferable because of its relatively low electrode potential to NOx. Particularly in the case of the oxygen-sensing electrode made of a platinum-iridium alloy having low electrode potential to NOx, the impedance of the electrode per se can be lowered.

[2] Production Method of Gas-detecting Element

Though there is no limitation in the production method of the gas-detecting element, it will be explained taking as an example where a zirconia green sheet is used. The use of a zirconia green sheet provides high productivity to the gas-detecting element. Zirconia powder as a starting material is preferably zirconia powder containing a predetermined amount of $Y_2O_3$, though zirconia powder and yttria powder may be mixed at a predetermined ratio. The starting material power is mixed with predetermined amounts of a binder and a solvent, blended by a ball mill, etc., and formed into a sheet by a doctor blade method, an injection method, etc.

When the gas-detecting elements shown in FIGS. 1–13 are produced, an electrode paste is applied onto a zirconia green sheet or a sintered solid electrolyte substrate by a screen-printing method, etc., to form a sensing electrode 5 and a reference electrode 7, and further an oxygen-sensing electrode 6 if necessary. If necessary, after repeating drying and printing, lead conductors and electrode-coating layers are similarly screen-printed. After the completion of screen-printing, the green sheet is degreased at about 500° C., and then sintered usually at 1400° C. or higher. Finally, lead wires are welded to collector terminals made of Pt, etc.

[3] Gas-detecting Device

The gas-detecting elements (detection cells) having the basic structures shown in FIGS. 1–13 can detect nitrogen oxides, hydrocarbon, carbon monoxide, ammonia, etc., exhibiting excellent effect particularly in the measurement of nitrogen oxides. Thus, detailed explanation will be given below with respect to a case where the gas-detecting device, into which the gas-detecting element of the present invention is assembled, is used for the detection of nitrogen oxides. Of course, the gas-detecting device of the present invention is effective to other detection object gases than nitrogen oxides, too.

(A) First Gas-detecting Device

Figure 14:
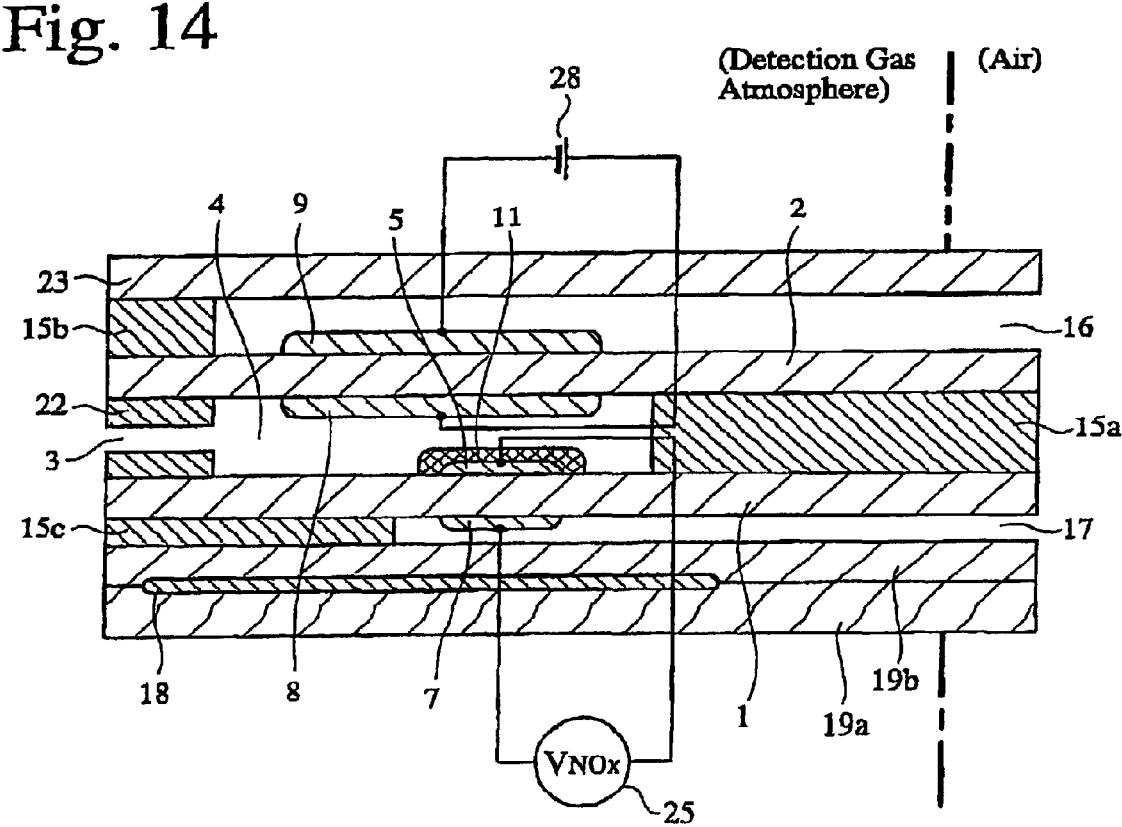
FIG. 14 is a schematic cross-sectional view showing a gas-detecting device according to one embodiment of the present invention.

FIG. 14 is a schematic cross-sectional view showing one example of the first gas-detecting device for measuring nitrogen oxides. This gas-detecting device is a laminate-type NOx sensor, which comprises (a) a gas-measuring chamber 4 defined by first and second oxygen-ion-conductive solid electrolyte substrates 1 and 2 disposed with a predetermined gap; (b) a gas inlet 3 provided so that a detection gas flows into the gas-measuring chamber 4 with a predetermined gas diffusion resistance; (c) a NOx-detecting cell comprising a sensing electrode 5 (hereinafter referred to as "NOx-sensing electrode") fixed onto the first solid electrolyte substrate 1 such that it is exposed to an atmosphere in the gas-measuring chamber 4, and active with NOx and oxygen, and a reference electrode 7 fixed onto the first solid electrolyte substrate 1 and active with oxygen; (d) a NOx-converting pump element comprising (i) a NOx-converting electrode 8 fixed onto the second solid electrolyte substrate 2 such that it is exposed to an atmosphere in the gas-measuring chamber 4, and active with NOx and oxygen, and (ii) a NOx-converting counter electrode 9 fixed onto the second solid electrolyte substrate 2 such that it is exposed to an atmosphere in a duct 16 containing oxygen and/or an oxide gas, and active with oxygen, which can convert NO to $NO_2$, or $NO_2$ to NO in the detection gas.

This gas-detecting device further comprises (e) a means 25 for measuring the potential difference between the NOx-sensing electrode 5 and the reference electrode 7, and (f) a voltage-applying means 28 for driving the NOx-converting pump element, whereby the concentration of NOx in the detection gas can be determined by detecting the potential difference between the NOx-sensing electrode 5 and the reference electrode 7 while applying predetermined voltage to the NOx-converting pump element. At least the NOx-sensing electrode 5 in the NOx-detecting cell is covered by the electrode-coating layer 11 made of an oxygen-ion-conductive solid electrolyte in such a form as to make it possible for a detection gas to reach an interface between the NOx-sensing electrode 5 and the first solid electrolyte substrate 1, the electrode underlayer or the electrode-coating layer. The electrode-coating layer 11 has a portion bonded to the first solid electrolyte substrate 1 directly or via an electrode underlayer (not shown) made of an oxygen-ion-conductive solid electrolyte.

The gas-detecting device is provided with a heater 18 (for instance, self-heating-type heater) for heating the NOx-detecting cell comprising the NOx-sensing electrode 5, the reference electrode 7 and the electrode-coating layer 11 to a predetermined temperature, and the heater 18 is integrally sandwiched by heater substrates 19a and 19b.

15a and 22 respectively indicate spacers for holding the first solid electrolyte substrate 1 and the second solid electrolyte substrate 2 at a predetermined gap, and the spacer 22 has a gas inlet 3. Also, 15b indicates a spacer for providing an air duct 16 communicating with the NOx-converting counter electrode 9, 15c indicates a spacer for providing an air duct 17 communicating with the reference electrode 7. Further, 23 indicates a substrate for defining the air duct 16.

In the gas-detecting device shown in FIG. 14, the electrode-coating layer 11' provided with gas-diffusing pores as shown in FIG. 2 may be used in place of the porous electrode-coating layer 11. The solid electrolyte substrates 1 and 2 are preferably made of the same zirconia solid electrolyte as above, and the spacer 15a is also preferably made of the same zirconia solid electrolyte. The heater substrates 19a and 19b sandwiching the heater 18 is preferably made of a zirconia solid electrolyte. In this case, an alumina layer, etc. having high electric insulation are preferably disposed in each interface between the heater substrates 19a and 19b and the heater 18.

Because the laminate-type NOx sensor shown in FIG. 14 has an electrochemical oxygen pump (NOx-converting pump element comprising NOx-converting electrode 8 and conversion counter electrode 9), it is possible to convert NO to $NO_2$ in a combustion exhaust gas to provide a detection gas, in which NOx is constituted by $NO_2$ only, or to convert $NO_2$ to NO in a combustion exhaust gas to provide a detection gas, in which NOx is constituted by NO only, depending on conditions, thereby detecting the total NOx concentration in the detection gas.

The conversion of a gas comprising a plurality of detection object gases to a gas comprising only one detection object gas by using such NOx-converting pump element can be carried out by introducing oxygen into the gas-measuring chamber 4 from outside to oxidize NO by the NOx-converting electrode 8, or by discharging oxygen from the gas-measuring chamber 4 to reduce $NO_2$ by the NOx-converting electrode 8. The structure shown in FIG. 14 is an example in which the conversion counter electrode 9 is disposed in the air duct 16 with oxygen pumped from air. However, the conversion counter electrode 9 can be disposed in the gas-measuring chamber 4, so that the conversion counter electrode 9 is exposed to a detection gas atmosphere, to electrochemically decompose an oxide in the detection gas for oxygen pumping. Oxides in the detection gas are usually $CO_2$, CO, $H_2O$, etc.

The material forming the conversion electrode 8 is preferably at least one precious metal selected from the group consisting of platinum, rhodium, iridium, gold and alloys containing these metals. The alloys may be a Pt—Rh alloy, an Ir—Rh alloy, a Pt—Ru alloy, etc. Particularly when the conversion electrode formed by a platinum-rhodium alloy such as Pt-5.5 mol % Rh, etc. is used, good NOx conversion can be carried out. In addition, when the conversion electrode 8 is formed by a mixture of at least one precious metal selected from the group consisting of platinum, rhodium, iridium, gold and alloys containing these metals and at least one metal oxide selected from the group consisting of $Cr_2O_3$, NiO, $NiCr_2O_4$, $MgCr_2O_4$ and $FeCr_2O_4$, the electrode 8 can be provided with excellent conversion stability. Incidentally, the material forming the conversion counter electrode 9 is not particularly restrictive as long as it is active with oxygen, though it is preferably Pt, Pd, Ir, etc., particularly preferably Pt.

With a structure having the electrode-coating layer 11 formed on the NOx-sensing electrode 5, it is possible to solve the problems of the instability of electrode interface, output drift, etc. due to thermal strain of the electrode, thereby stabilizing the electrochemical activity of electrode interface. In addition, because the interface impedance of the electrode can be reduced, it is possible to improve response performance at the time of detecting a gas. Because the reference electrode 7 active with oxygen is disposed in the air duct 17 in this sensor structure, it is completely isolated from a detection gas, so that it can function as a reference electrode. The material of the reference electrode 7 is usually Pt, it is possible to add an oxygen ion conductor such as a zirconia solid electrolyte to improve oxygen activity.

Though, in the example of FIG. 14, only the NOx-sensing electrode 5 is covered by the electrode-coating layer 11, the reference electrode 7 disposed in the air duct 17, of course, may also be covered by the electrode-coating layer 12. This improves the electrode interface stability of not only the NOx-sensing electrode 5 but also the reference electrode 7, resulting in decrease in interface impedance. As a result, the change ratio of drift further decreases in the gas-detecting device, resulting in improvement in gas detection stability.

Figure 15:
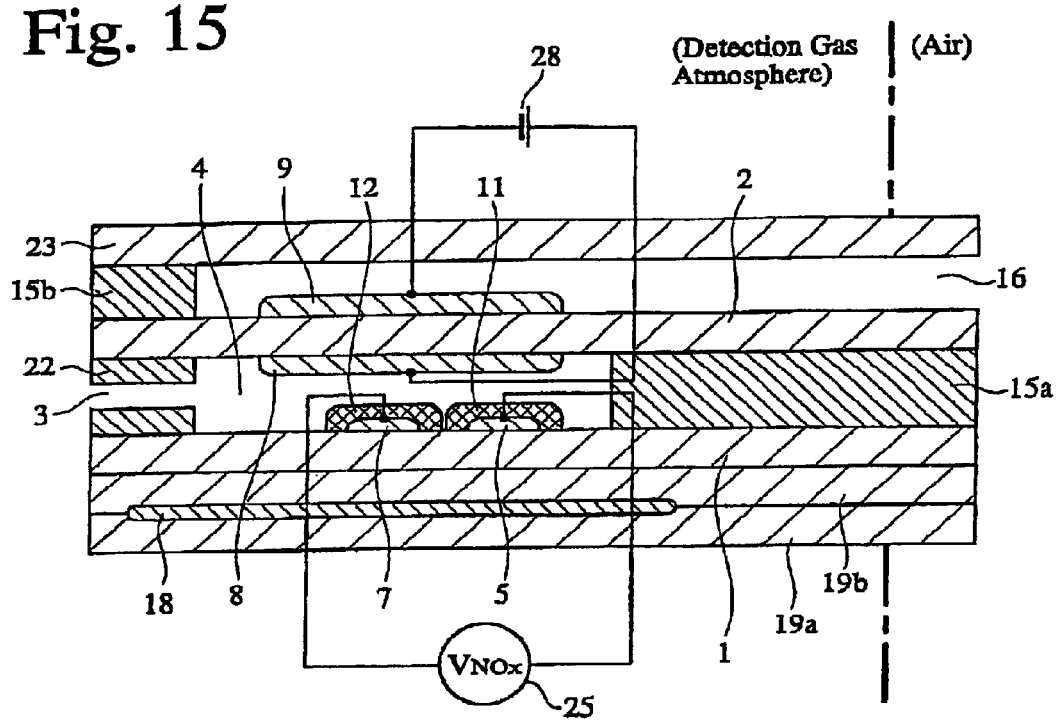
FIG. 15 is a schematic cross-sectional view showing a gas-detecting device according to another embodiment of the present invention.
Figure 16:
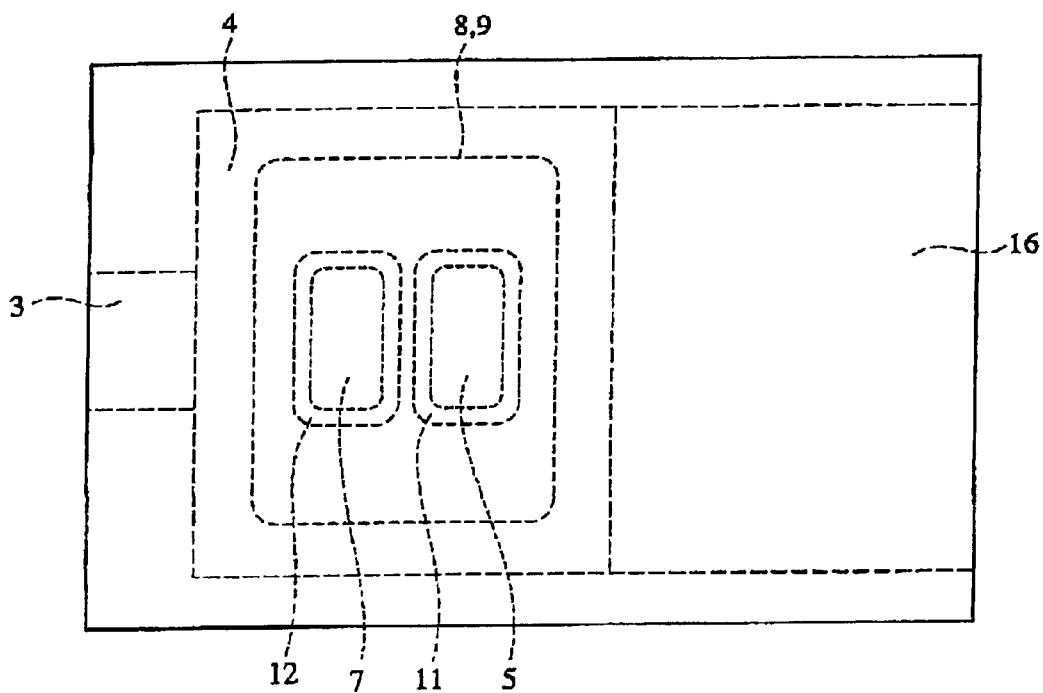
FIG. 16 is a plan view showing the gas-detecting device of FIG. 15.

FIG. 15 is a schematic cross-sectional view showing another example of the gas-detecting device, and FIG. 16 is its plan view. FIG. 16 shows the in-plane arrangement of each part of the gas-detecting device. Incidentally, in other examples of the gas-detecting devices, too, the in-plane arrangement of each element is substantially the same as in FIG. 16. In FIG. 15, the same reference numerals are assigned to parts operating substantially in the same manner as in FIG. 14. In the gas-detecting device shown in FIG. 15, the reference electrode 7 is disposed on the same surface as the sensing electrode 5, thereby being exposed to a detection gas atmosphere. The reference electrode 7 should be active with oxygen but inactive with NOx. The material forming such reference electrode 7 is preferably Pt.

When the reference electrode 7 active with oxygen but inactive with NOx is used in such a mixed-potential-type sensor, the reference electrode 7 can be disposed in the same detection gas atmosphere as the NOx-sensing electrode 5. The reference electrode 7 is preferably disposed in the vicinity of the NOx-sensing electrode 5. Though both of the NOx-sensing electrode 5 and the reference electrode 7 are covered by the electrode-coating layers 11, 12 in FIG. 15, the covering of either one of them, of course, provides a considerable effect. The electrode-coating layers 11, 12 act to improve the interface bonding stability of the solid electrolyte substrate/the electrode and gas response.

In such a structure that the reference electrode 7 is opposing the NOx-converting electrode 8, the covering of the reference electrode 7 with the electrode-coating layer 12 provides remarkable effect of preventing contamination. Namely, the electrode-coating layer 12 can efficiently prevent the phenomenon that contamination components generated from the NOx-converting electrode 8 at the time of sintering or using the gas-detecting device provide the reference electrode with activity with NOx.

Figure 17:
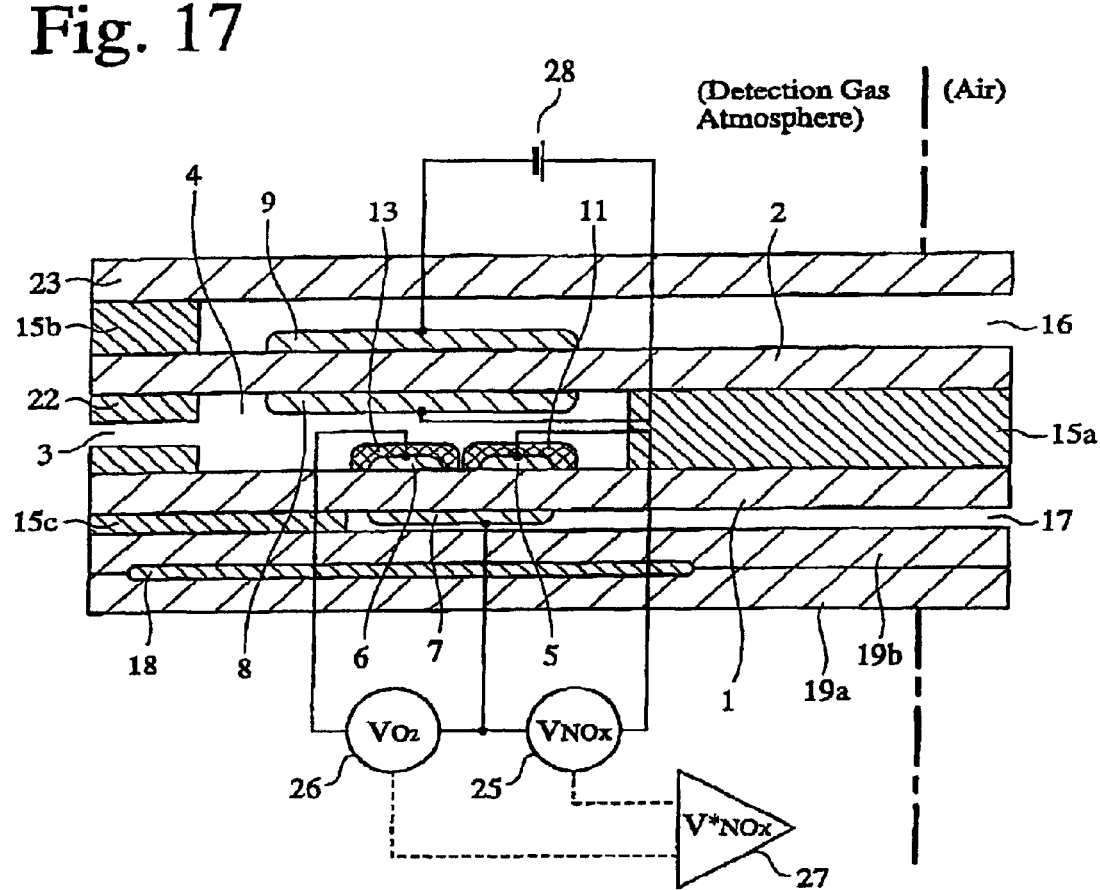
FIG. 17 is a schematic cross-sectional view showing a gas-detecting device according to a further embodiment of the present invention.

FIG. 17 is a schematic cross-sectional view showing a further example of the gas-detecting device. In FIG. 17, the same reference numerals are assigned to parts operating substantially in the same manner as in FIGS. 14 and 15. FIG. 17 shows a structure in which an oxygen sensing electrode 6 active with oxygen but inactive with NOx is disposed in a gas-measuring chamber 4, and a reference electrode 7 for both of the NOx-sensing electrode 5 and the oxygen sensing electrode 6 is disposed in an air duct 17. The material forming the oxygen-sensing electrode 6 is preferably Pt, Pd, Ir, a Pt—Ir alloy, etc. Of course, two reference electrodes may be arranged separately for the NOx-sensing electrode 5 and the oxygen-sensing electrode 6.

With an arithmetic treatment means 27 using potential difference $E_2$ between the reference electrode 7 and the oxygen-sensing electrode 6 and potential difference $E_1$ between the reference electrode 7 and the NOx-sensing electrode 5, corrections are made to the variation of oxygen concentration. The arithmetic treatment means 27 may be hardware using an electronic circuit, or software using a microcomputer, etc. This makes it possible to detect NOx with high precision even when the variation of oxygen concentration in a detection gas atmosphere influences the oxygen concentration in the gas-measuring chamber 4.

Though in the example shown in FIG. 17, both of the NOx-sensing electrode 5 and the oxygen-sensing electrode 6 are covered by the electrode-coating layers 11, 13, the reference electrode 7, of course, may be covered by the electrode-coating layer 12. In the structure in which the oxygen-sensing electrode 6 is opposing the NOx-converting electrode 8, the electrode-coating layer 13 is effective to prevent contamination from the NOx-converting electrode 8, whereby the electrode-coating layer 13 efficiently prevents the phenomenon that oxygen-sensing electrode 6 is given activity with NOx, like the reference electrode 7 shown in FIG. 15. The preferred example of the electrode-coating layer 13 is the same as the above electrode-coating layer 12 covering the reference electrode 7 opposing the NOx-converting electrode 8.

Figure 18:
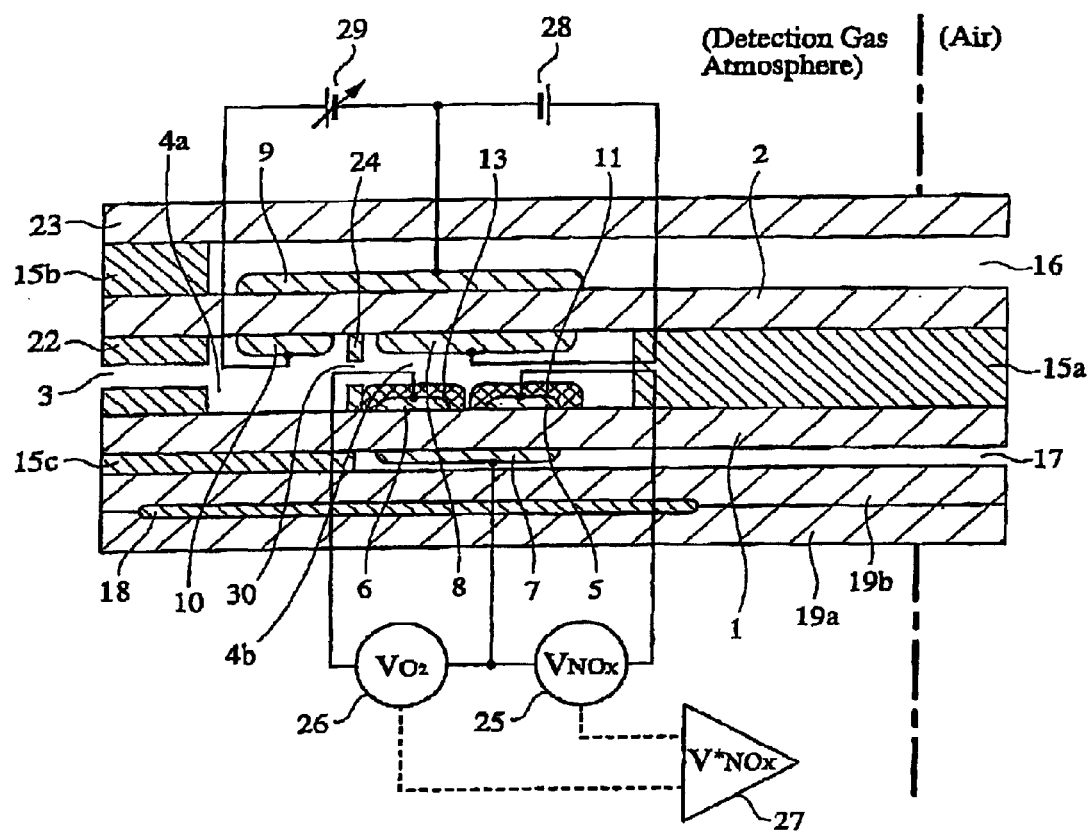
FIG. 18 is a schematic cross-sectional view showing a gas-detecting device according to a still further embodiment of the present invention.

FIG. 18 is a schematic cross-sectional view showing a still further example of the gas-detecting device. In FIG. 18, the same reference numerals are assigned to parts operating substantially in the same manner as in FIGS. 14–17. The laminate-type NOx sensor shown in FIG. 18 is constituted by adding, to the structure shown in FIG. 17, a gas-treating electrode 10 for oxidizing a reducing gas in a detection gas atmosphere (for instance, CO, HC, etc. in a combustion exhaust gas) in a front part of the gas-measuring chamber 4. The gas-treating electrode 10 is active with HC, CO, etc. Though FIG. 18 shows an example in which the conversion counter electrode 9 serves as a counter electrode for both of the gas-treating electrode 10 and the NOx-converting electrode 8, two conversion counter electrodes 9 may be arranged separately for the gas-treating electrode 10 and the NOx-converting electrode 8.

The gas-detecting device shown in FIG. 18 comprises a gas-treating pump element constituted by the gas-treating electrode 10 and its counter electrode 9, and an external power supply 29 as a means for applying voltage to the gas-treating pump element. With a gas-flow-resisting member 24 having a gas-passing aperture 30 disposed between the gas-treating electrode 10 and the NOx-converting electrode 8, the gas-measuring chamber 4 may be turned into a two-chamber structure having a gas-converting chamber 4a (first chamber) and a gas-measuring chamber 4b (second chamber). By increasing oxide concentration in the gas-converting chamber 4a, the variation of oxygen concentration in the gas-measuring chamber 4b is suppressed, resulting in increase in sensor performance, thereby achieving high-precision NOx detection. The material forming the gas-treating electrode 10 is preferably Pt, Pd, Ir, Au, Rh, etc.

Figure 19:
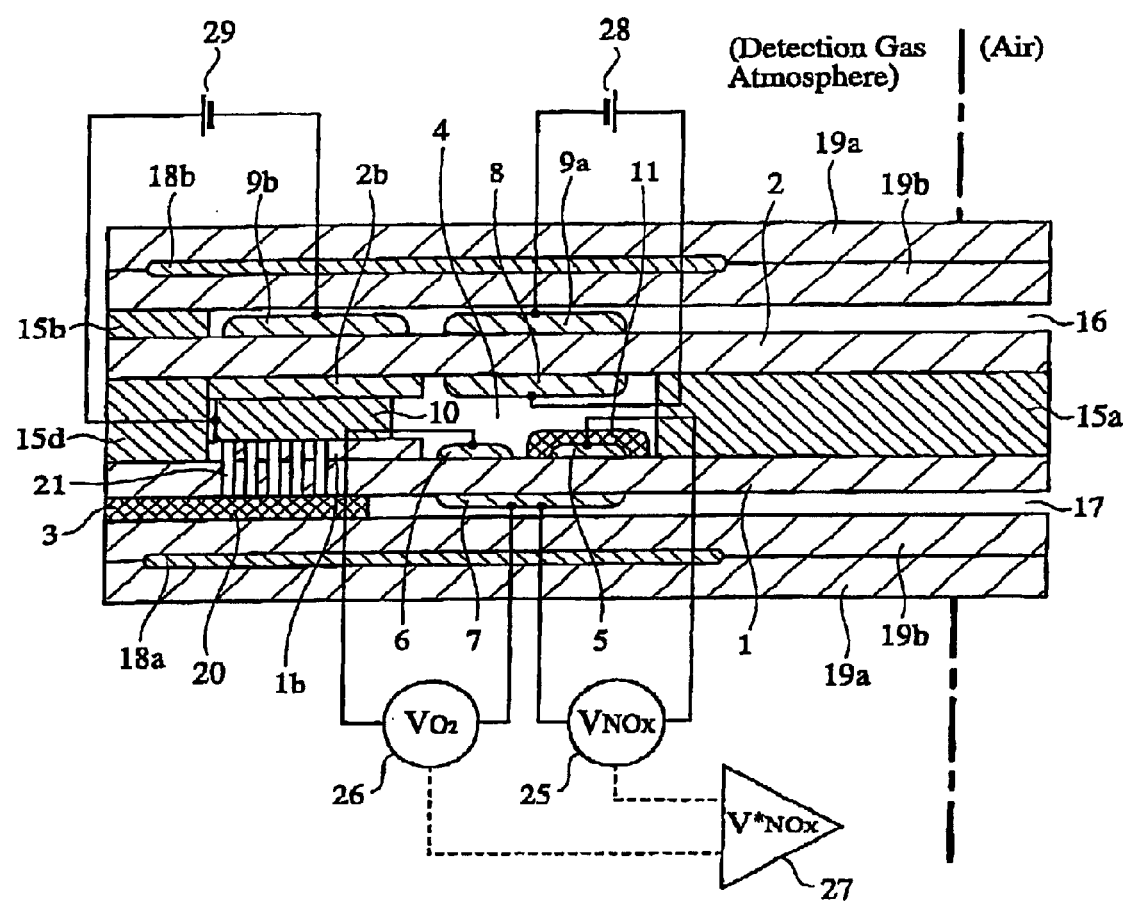
FIG. 19 is a schematic cross-sectional view showing a gas-detecting device according to a still further embodiment of the present invention.

FIG. 19 is a schematic cross-sectional view showing a still further example of the gas-detecting device. In FIG. 19, the same reference numerals are assigned to parts operating substantially in the same manner as in FIGS. 14–18. In the laminate-type NOx sensor shown in FIG. 19, a plurality of gas-passing apertures 21 are provided such that they penetrate a solid electrolyte substrate 1 on which a NOx-sensing electrode 5 and a solid electrolyte substrate 1b are formed. A region of the solid electrolyte substrate 1, in which the gas-passing apertures 21 open, is covered by a porous body 20 functioning as a spacer for an air duct 17. The porous body 20 has pores constituting gas inlets 3, in which an oxidation catalyst is carried.

The detection gas enters into the pores of the porous body 20, in which HC (hydrocarbons) and CO are oxidized by an oxidation catalyst to increase oxide concentration. After the detection gas passes through the gas-passing apertures 21, it is diffused into a gas-treating electrode 10 constituted by a porous layer sandwiched by the solid electrolyte substrates 1b and 2b, to further increase oxide concentration. With such structure, a gas treatment effect is increased. The porosity of the porous body 20 carrying the oxidation catalyst and the gas-treating electrode 10 are designed preferably so that the gas-flowing resistance is not a parameter determining a gas diffusion rate. The conversion counter electrode 9b for the gas-treating electrode 10 is disposed separately from the conversion counter electrode 9a for the NOx-converting electrode 8. To increase the uniformity of heating temperature of a sensor element, a pair of heaters 18a and 18b are arranged in the substrate on both sides of the gas-detecting element.

(B) Second Gas-detecting Device

Figure 21:
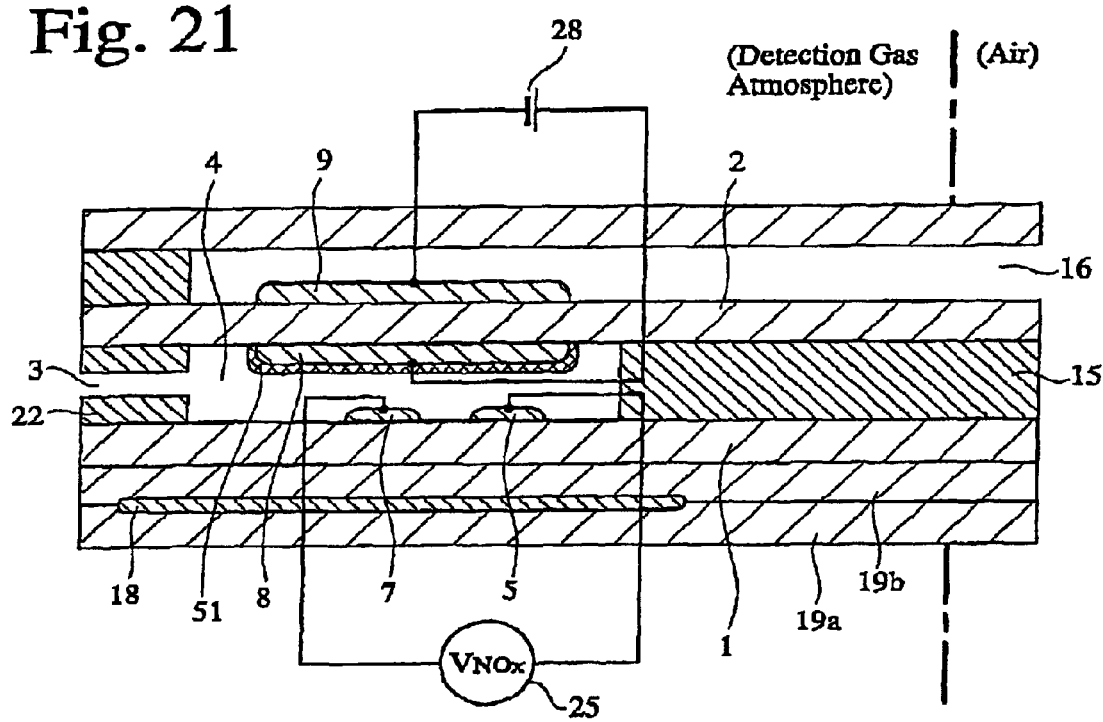
FIG. 21 is a schematic cross-sectional view showing a gas-detecting device according to a still further embodiment of the present invention.

FIG. 21 is a schematic cross-sectional view showing an example of the second gas-detecting device (laminate-type NOx sensor). In FIG. 21, the same reference numerals are assigned to parts operating substantially in the same manner as in FIG. 14. This gas-detecting device is different from the first gas-detecting device shown in FIG. 14 in the structure of a NOx-converting pump element. Accordingly, detailed explanation will be made below with respect to the NOx-converting pump element.

Figure 22:
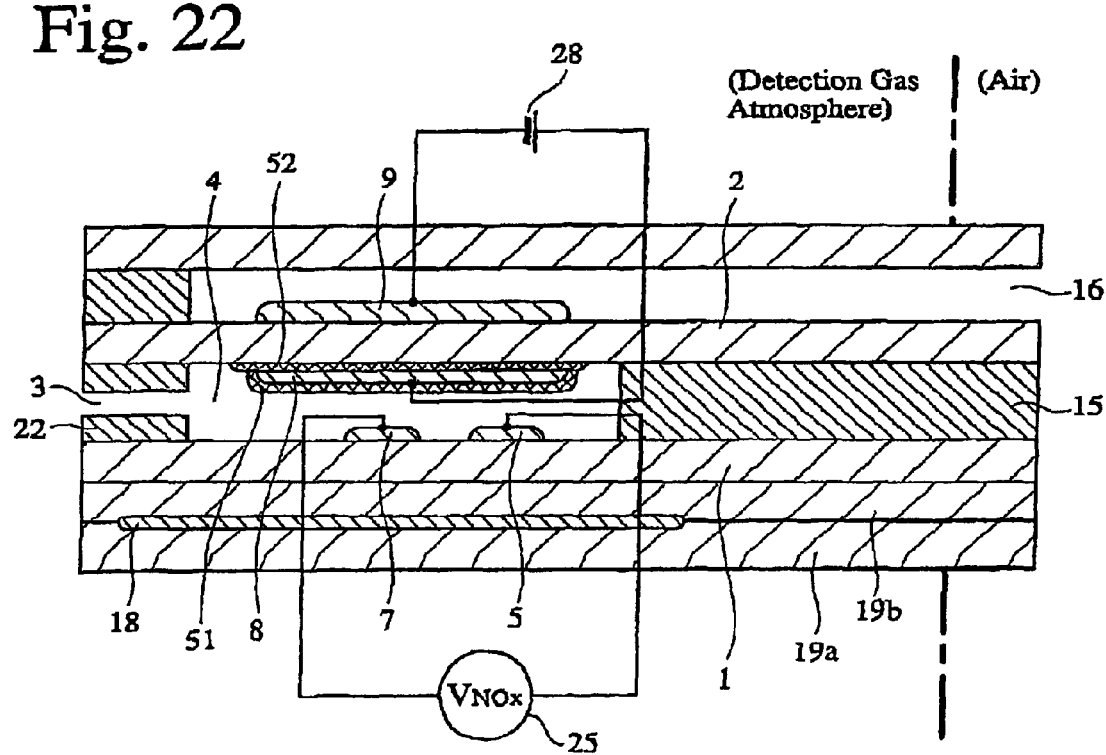
FIG. 22 is a schematic cross-sectional view showing a gas-detecting device according to a still further embodiment of the present invention.

In the NOx-converting pump element of the second gas-detecting device, at least a NOx-converting electrode 8 is covered by an electrode-coating layer 51 made of an oxygen-ion-conductive solid electrolyte. The electrode-coating layer 51 is in such a form that a detection gas can reach a three-phase interface of a solid electrolyte substrate, an electrode underlayer or an electrode-coating layer and each electrode. The electrode-coating layer 51 has a portion bonded to the second solid electrolyte substrate 2 directly (FIG. 21) or via an electrode underlayer 52 made of an oxygen-ion-conductive solid electrolyte (FIG. 22). Accordingly, the fixing of the NOx-converting electrode 8 covered by the electrode-coating layer 51 to the second solid electrolyte substrate 2 is reinforced. The electrode-coating layer 51 eliminates the bonding instability of interface between the second solid electrolyte substrate 2 and the NOx-converting electrode 8 due to thermal stress caused by the difference in a thermal expansion coefficient therebetween. In addition, the NOx-converting electrode 8 covered by the electrode-coating layer 51 is prevented from direct contact with a remaining reducing gas, whereby electrochemical activity contributing to the function of NOx conversion is stabilized.

The electrode-coating layer 51 is preferably a porous solid electrolyte layer, through which a detection gas (detection object gas) is diffusible, and the porosity of the porous solid electrolyte film layer is preferably 10–50%. When the porosity is less than 10%, it takes too much time for the detection object gas to diffuse to the conversion electrode, resulting in elongated gas response time and thus insufficient NOx conversion. On the other hand, when the porosity is more than 50%, the electrode-coating layer 51 has poor strength, failing to mechanically suppress strain generated between the NOx-converting electrode 8 and the solid electrolyte substrate 2. As a result, the electrode interface is likely to become unstable by thermal stress due to the difference between them in a thermal expansion coefficient, failing to obtain stable detection output.

The thickness of the electrode-coating layer 51 is an important factor for obtaining good effects. The electrode-coating film layer 51 preferably has an average thickness of 3–20 $\mu$m. When the thickness of the electrode-coating layer 51 is less than 3 $\mu$m, the electrode-coating layer 51 per se has too low strength. On the other hand, when the thickness is more than 20 $\mu$m, it takes too much time for the detection object gas to diffuse to the conversion electrode 8, resulting in elongated gas response time and thus insufficient NOx conversion.

The electrode-coating layer 51 is made of an oxygen-ion-conductive zirconia solid electrolyte, which preferably contains at least one selected from the group consisting of yttria ($Y_2O_3$), ceria ($CeO_2$), magnesia ($MgO$) and scandia ($Sc_2O_3$) as a stabilizer from the aspect of sensor performance. The amount of the stabilizer added is preferably 3–20 mol % based on the total amount of the solid electrolyte. When the amount of the stabilizer added is less than 3 mol %, there is insufficient oxygen ion conductivity. On the other hand, when it is more than 20 mol %, the electrode-coating layer 51 has low strength, resulting in decrease in stability and increase in the variations of output. The stabilizer added is preferably uniformly dispersed in zirconia, and completely dissolved in a solid phase thereof. However, even if a trace amount of a stabilizer remains microscopically in grain boundaries, etc., the effects of the present invention would not be affected.

In the case of detecting NOx, the oxygen-ion-conductive zirconia solid electrolyte for the electrode-coating layer 51 preferably further contains (a) at least one precious metal selected from the group consisting of platinum, rhodium, iridium, gold and alloys containing these metals, and/or (b) at least one metal oxide selected from the group consisting of $Cr_2O_3$, NiO, $NiCr_2O_4$, $MgCr_2O_4$ and $FeCr_2O_4$. The amount of the precious metal and/or the metal oxide added is preferably in a range of 1–50% by volume (total amount, when both are contained), based on 100% by volume of the zirconia solid electrolyte.

FIG. 22 is a schematic cross-sectional view showing another example of the gas-detecting device. In FIG. 22, the same reference numerals are assigned to parts operating substantially in the same manner as in FIG. 21. The gas-detecting device shown in FIG. 22 has a structure in which a NOx-converting electrode 8 is formed on a solid electrolyte substrate 2 via an electrode underlayer 52 made of an oxygen-ion-conductive solid electrolyte. The electrode-coating layer 51 not only covers the NOx-converting electrode 8 but also is bonded to the electrode underlayer 52.

The electrode underlayer 52 is preferably made of a zirconia solid electrolyte containing as a stabilizer at least one selected from the group consisting of yttria, ceria, magnesia and scandia. The electrode underlayer 52 is preferably made of the same material as those of the NOx-converting electrode 8 and the electrode-coating layer 51, which more preferably contains at least one precious metal selected from the group consisting of platinum, rhodium, iridium, gold and alloys containing these metals, and/or at least one metal oxide selected from the group consisting of $Cr_2O_3$, NiO, $NiCr_2O_4$, $MgCr_2O_4$ and $FeCr_2O_4$, in a range of 0.1–20% by volume (total amount, when both are contained). The electrode underlayer 52 is a dense or porous layer preferably having a thickness of about 3 to 10 $\mu$m.

[4] Production Method of Gas-detecting Device

Figure 20:
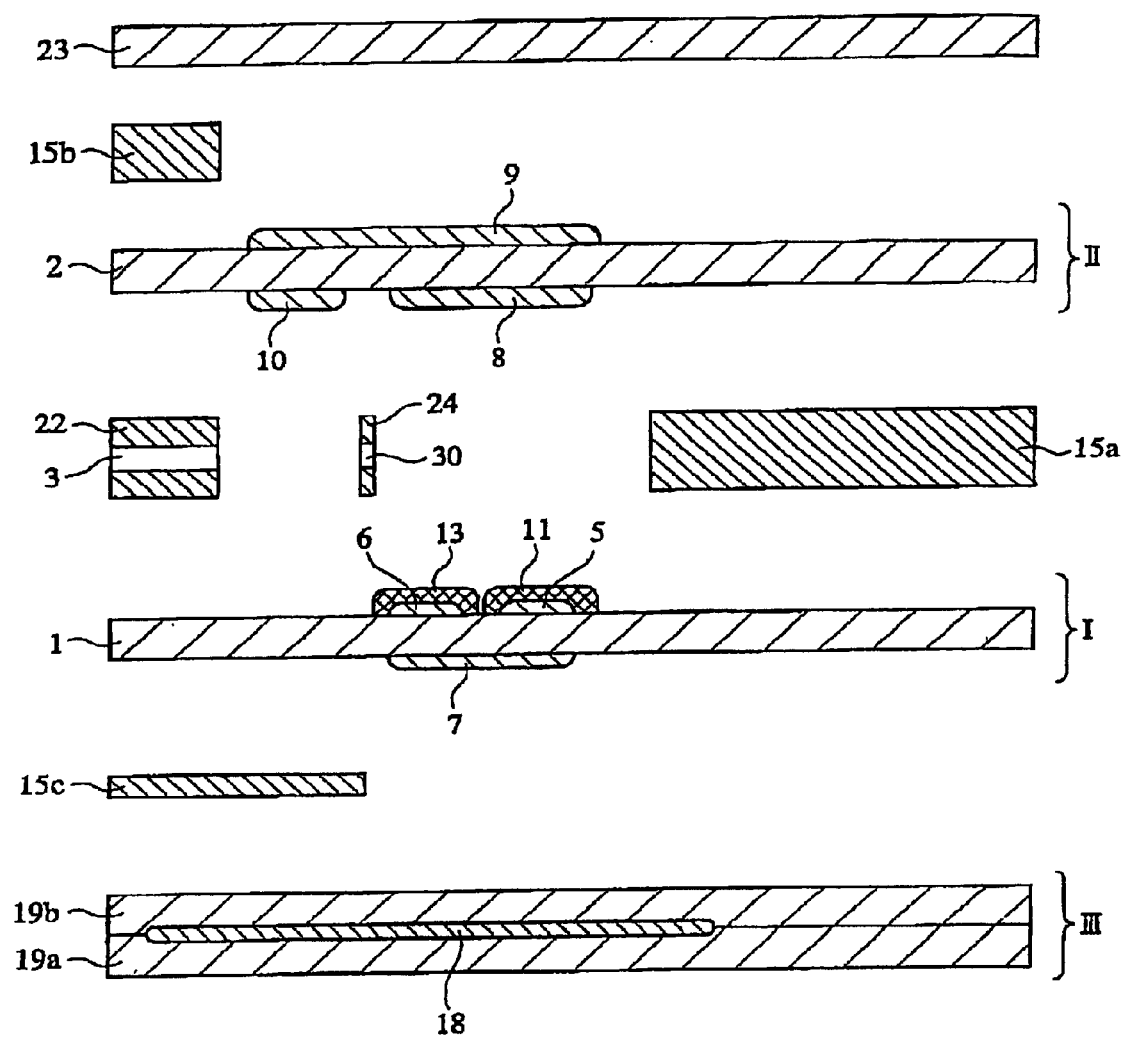
FIG. 20 is an exploded view of the gas-detecting device of FIG. 18.

In the production of the laminate-type NOx sensors shown in FIGS. 14–22, it is preferable to use green sheets as in the case of the gas-detecting element. For instance, in the case of the production of the laminate-type NOx sensor shown in FIG. 18, the NOx-sensing electrode 5, the oxygen-sensing electrode 6 and the electrode-coating layers 11, 13 are screen-printed on one surface of a green sheet I as shown in FIG. 20, and the reference electrode 7 is screen-printed on the other surface of the green sheet I, and further necessary lead conductors are screen-printed to form a detection cell. Also, the NOx-converting electrode 8 and the gas-treating electrode 10 are screen-printed on one surface of a green sheet II, and the NOx-converting counter electrode 9 is screen-printed on the other surface of the green sheet II, and further necessary lead conductors are screen-printed to form a conversion pump element. Further, by sandwiching the heater 18 and its lead conductors with two green sheets for the solid electrolyte substrates 19a, 19b, a sheet III for the heater portion is produced.

Green sheets for spacers 15a, 22 and a gas-flow-resisting member 24 are sandwiched by the green sheets I and II, and a green sheet for a spacer 15c is sandwiched by the green sheets I and III, and finally a green sheet for the substrate 23 for the air duct is laminated on the green sheet II via a green sheet for a spacer 15b. In this case, a portion of the element turning to an internal space is in advance filled or printed with a thermally removable material such as Theobromine, etc., which is sublimed at a degreasing temperature. The resultant laminate is pressed while heating, degreased at about 500° C., and then sintered, for instance, at 1400° C. or higher. Lead wires of Pt, etc. are finally welded to the collector terminals of the resultant sintered body.

Though the gas-detecting element and the gas-detecting device in each Example of the present invention have been explained above in detail with respect to their structures and compositions constituting their parts, etc., these explanations are applicable to the gas-detecting elements and the gas-detecting devices in any Examples unless otherwise mentioned.

The present invention will be explained in further detail by way of the following Examples, without intention of restricting the present invention thereto.

REFERENCE EXAMPLE 1

NOx gas-detecting elements (NOx sensor) without electrode-coating layers were produced. As shown in Table 1, NOx-sensing electrodes were produced by metal oxides active with NOx and oxygen, precious metals active with NOx and oxygen, and precious metals inactive with NOx and active with oxygen. To produce a zirconia solid electrolyte substrate, green sheets of zirconia powder containing 6 mol % of yttria were produced by a doctor blade method. Each green sheet had a size of 0.25 mm×5 mm×50 mm. Incidentally, when a sintered substrate is used, the substrate has a thickness of about 200 $\mu$m.

Each green sheet was cut to a rectangular shape, and a Pt lead conductor was screen-printed. Thereafter, each sensing electrode material shown in Table 1 was screen-printed thereon to form a NOx-sensing electrode. A Pt paste for a reference electrode was screen-printed onto a surface of the green sheet opposing the NOx-sensing electrode. Each of the resultant green sheets (sensor elements) for a gas-detecting element was degreased at about 500° C. in air and sintered at about 1400° C. in air. When a sintered substrate is used, a degreasing step is unnecessary, and sintering is carried out at 100–1300° C. Lead wires were connected to each sintered NOx sensor to provide a sensor sample.

Each sensor sample was set in a quartz pipe and held in an electric furnace, in which it was exposed to a detection gas, which contained 100 ppm of a NOx gas ($NO_2$ or NO) and 5% by volume of oxygen, the balance being nitrogen, for comparison of activity with NOx. The electric furnace was controlled at an atmosphere temperature of 600° C. The output of each sensor sample to NOx was measured by a voltmeter with high input impedance. The results are shown in Table 1.

In this Reference Example, it was confirmed in advance that a Pt electrode is not sensitive to any of NO and $NO_2$.

TABLE 1

| | Sensing electrode | Sensitivity to 100 ppm of $NO_2$ (mV) | Sensitivity to 100 ppm of NO (mV) |
|---|---|---|---|
| A | Pd | 5 | −2 |
| | Pt—Pd (10% by mass) | 2 | −1 |
| | Pd—Ru (5% by mass) | 0 | 0 |
| B | Ir | 42 | −12 |
| | Au | 51 | −13 |
| | Rh | 60 | −5 |
| | Ir—Au (10% by mass) | 60 | −15 |
| | Ir—Rh (5% by mass) | 73 | −16 |
| | Au—Rh (5% by mass) | 68 | −14 |
| B' | Pt—Rh (3% by mass) | 95 | −23 |

TABLE 1-continued

| | Sensing electrode | Sensitivity to 100 ppm of $NO_2$ (mV) | Sensitivity to 100 ppm of NO (mV) |
|---|---|---|---|
| C | NiO | 78 | −18 |
| | $WO_3$ | 56 | −11 |
| | $Cr_2O_3$ | 96 | −25 |
| | $NiCr_2O_4$ | 103 | −31 |
| | $FeCr_2O_4$ | 97 | −27 |
| | $MgCr_2O_4$ | 95 | −25 |
| | $CrMnO_3$ | 70 | −13 |
| | $CrWO_4$ | 68 | −12 |
| | $LaCrO_3$ | 58 | −12 |
| | $NiTiO_3$ | 47 | −11 |
| | $FeTiO_3$ | 51 | −13 |
| | $ZnFe_2O_4$ | 61 | −14 |

As shown in Table 1, the precious metal material in the group A did not show any sensitivity to NOx, proving that it was substantially inactive with NOx. On the other hand, the precious metal material in the group B showed high activity with NOx. Though the metal oxide material in the group C showed excellent sensitivity to NOx, it was found that oxides containing Cr as a constituent element among others had high sensitivity and sensitivity stability. It was found that particularly $NiCr_2O_4$, $FeCr_2O_4$, $MgCr_2O_4$ and $Cr_2O_3$ had high sensitivity and sensitivity stability. Accordingly, it is possible to use the precious metal materials in the group B as the first precious metal and the precious metal materials in the group A as the second precious metal in the present invention. It was also confirmed that Pt—Rh (3% by mass) in the group B', an alloy of Pt in the group A and Rh in the group B, had high sensitivity to NOx and high stability in sensitivity.

EXAMPLES 1–8

Samples of NOx gas-detecting elements (NOx sensors) having the structure shown in FIG. 1 were produced, in the same manner as in Reference Example 1 except for using an Ir—Rh (5% by mass) alloy, a Pt—Rh (3% by mass) alloy, $Cr_2O_3$ or $NiCr_2O_4$ to form a NOx-sensing electrode 5 on each solid electrolyte green sheet, and then screen-printing a material shown in Table 2 thereon to form an electrode-coating layer 11 having an average thickness of 15 μm and a porosity of 30%. The reference electrode 7 was not covered by the electrode-coating layer.

Each of the resultant sensor samples was set in a quartz pipe and held in an electric furnace, which was controlled at an atmosphere temperature of 600° C. By an accelerated deterioration test in which each sample was exposed to a detection gas containing 100 ppm of $NO_2$ gas and 5% by volume of oxygen, the balance being nitrogen, the detection performance of each sensor sample was examined. An output to $NO_2$ was measured by a voltmeter with high input impedance. The results are shown in Table 2.

Comparative Examples 1–4

Sensor samples were produced to examine their detection performance in the same manner as in Examples 1–8 except that no electrode-coating layer 11 was formed. The results are shown in Table 2.

TABLE 2

| No. | Sensing electrode* | Electrode-Coating Layer | Initial Sensitivity[1] (mV) | Gas Response[2] | Change Ratio of Drift[3] (%) |
|---|---|---|---|---|---|
| Example 1 | Ir—Rh (5%) | $Y_2O_3$ (8 mol %)-$ZrO_2$ | 71 | ◯ | −21 |
| Example 2 | Ir—Rh (5%) | $CeO_2$ (12 mol %)-$ZrO_2$ | 70 | ◯ | −12 |
| Com. Ex. 1 | Ir—Rh (5%) | No | 73 | Δ | −45 |
| Example 3 | Pt—Rh (3%) | $Y_2O_3$ (8 mol %)-$ZrO_2$ | 90 | ◯ | −26 |
| Example 4 | Pt—Rh (3%) | $CeO_2$ (12 mol %)-$ZrO_2$ | 92 | ◯ | −15 |
| Com. Ex. 2 | Pt—Rh (3%) | No | 95 | Δ | −54 |
| Example 5 | $Cr_2O_3$ | $Y_2O_3$ (8 mol %)-$ZrO_2$ | 93 | ⊙ | −23 |
| Example 6 | $Cr_2O_3$ | $CeO_2$ (12 mol %)-$ZrO_2$ | 91 | ⊙ | −14 |
| Com. Ex. 3 | $Cr_2O_3$ | No | 96 | ◯ | −68 |
| Example 7 | $NiCr_2O_4$ | $Y_2O_3$ (8 mol %)-$ZrO_2$ | 100 | ⊙ | −19 |
| Example 8 | $NiCr_2O_4$ | $CeO_2$ (12 mol %)-$ZrO_2$ | 98 | ⊙ | −16 |
| Com. Ex. 4 | $NiCr_2O_4$ | No | 103 | ◯ | −72 |

Note:
*Unit is % by mass.
[1]Expressed by the difference between a sensor output obtained in the case of an $N_2$ base gas containing 5% by volume of oxygen, and a sensor output obtained in the case of a gas formulated by adding 100 ppm of $NO_2$ to the base gas.
[2]Relative evaluation ⊙: Excellent. ◯: Fair. Δ: Poor.
[3]Expressed by the ratio of the difference (degree of change) between an initial sensitivity to $NO_2$ (100 ppm) and sensitivity to $NO_2$ (100 ppm) after the accelerated deterioration test to the initial sensitivity. "+" means the increase in sensitivity, and "−" means the decrease in sensitivity.

The comparison of Examples 1–8 with Comparative Examples 1–4 revealed that any of sensor samples of Examples 1–8 each having an electrode-coating layer 11 had a drastically decreased change ratio of drift and improved response. It was confirmed that particularly when a metal oxide was used for the NOx-sensing electrode 5, the effect of eliminating the drift was remarkable, resulting in improvement in durability.

EXAMPLES 9–16

As shown in FIG. 2, with a NOx-sensing electrode 5 fixed in a recess 1a of a solid electrolyte substrate 1, a NOx sensor having a structure in which an electrode-coating layer 11' made of a solid electrolyte having gas-diffusing pores 14 was formed on an upper surface of the NOx-sensing electrode 5 by the following procedures: First, the NOx-sensing electrode 5 was formed in the recess 1a formed in advance in the solid electrolyte substrate 1 by a screen-printing method. A plurality of gas-diffusing pores 14 were formed in a zirconia green sheet having a predetermined thickness to form a green sheet for the electrode-coating layer 11'. A green sheet for the electrode-coating layer 11' was placed on the solid electrolyte substrate 1 such that the gas-diffusing pores 14 were positioned above the NOx-sensing electrode 5, and the resultant assembly was pressed with lead wires inserted. The other procedures than these steps were the same as in Reference Example 1. The reference electrode 7 was not covered by the electrode-coating layer. A ratio (Sh/Se) of the total opening area (Sh) of the gas-diffusing pores 14 to the area (Se) of the sensing electrode was set at 0.15.

Each of the resultant laminates was degreased and sintered under the same conditions as in Reference Example 1. Any of the resultant sintered bodies had a thickness of about 30 μm. The detection performance of each sensor sample thus obtained was evaluated in the same manner as in Example 1. The results are shown in Table 3.

COMPARATIVE EXAMPLES 5–8

Each sensor samples was produced to examine its detection performance in the same manner as in Examples 9–16 except that no electrode-coating layer was formed. The results are shown in Table 3.

smaller in any of the sensor samples of Examples 9–16 than in the sensor samples of Examples 1–8 provided with porous electrode-coating layers 11. On the other hand, with respect to sensitivity to 100 ppm of $NO_2$, the sensor samples of Examples 9–16 were slightly lower than those of Examples 1–8, though there was no substantial decrease. With respect to response, it was confirmed that the sensor samples of Examples 9–16 were improved than those of Comparative Examples 5–8 as a whole.

EXAMPLES 17–28

Samples of NOx sensors having the structures shown in FIGS. 3, 4, 6, 8–10 were produced. $Cr_2O_3$ or $NiCr_2O_4$ was used for a sensing electrode, and a zirconia solid electrolyte containing 12 mol % of $CeO_2$ was used for an electrode-coating layer.

Sensor samples having the structure shown in FIG. 3 were produced, in the same manner as in Reference Example 1 except that a zirconia solid electrolyte containing 14 mol % of $CeO_2$ was screen-printed on a green sheet for a solid electrolyte substrate, to form an electrode underlayer 31 having a porosity of 10% and a thickness of 3 μm, and that after forming a NOx-sensing electrode 5, an electrode-coating layer 11 having a porosity of 30% and an average thickness of 15 μm was formed by a screen-printing method.

Sensor samples having the structure shown in FIG. 4 were produced, in the same manner as in Reference Example 1 except for forming an alumina print layer as an electric insulating layer 32 on a green sheet for the solid electrolyte substrate 1, forming a NOx-sensing electrode 5 and a reference electrode 7, and then screen-printing an electrode-coating layer 11 thereon.

Sensor samples having the structure shown in FIG. 6 were produced, in the same manner as in Reference Example 1 except that a NOx-sensing electrode 5 and a reference electrode 7 were formed on the same surface of the green sheet, and that an electrode-coating layer 11 was screen-printed only on the NOx-sensing electrode 5.

Sensor samples having the structure shown in FIG. 8 were produced, in the same manner as in Reference Example 1

TABLE 3

| No. | Sensing electrode | Electrode-Coating Layer | Initial Sensitivity[1] (mV) | Gas Response[2] | Change Ratio of Drift[3] (%) |
|---|---|---|---|---|---|
| Example 9 | Ir—Rh (5%) | $Y_2O_3$ (8 mol %)-$ZrO_2$ | 69 | ○ | −19 |
| Example 10 | Ir—Rh (5%) | $CeO_2$ (12 mol %)-$ZrO_2$ | 68 | ○ | −11 |
| Com. Ex. 5 | Ir—Rh (5%) | No | 73 | Δ | −45 |
| Example 11 | Pt—Rh (3%) | $Y_2O_3$ (8 mol %)-$ZrO_2$ | 88 | ○ | −24 |
| Example 12 | Pt—Rh (3%) | $CeO_2$ (12 mol %)-$ZrO_2$ | 91 | ○ | −13 |
| Com. Ex. 6 | Pt—Rh (3%) | No | 95 | Δ | −54 |
| Example 13 | $Cr_2O_3$ | $Y_2O_3$ (8 mol %)-$ZrO_2$ | 91 | ⊚ | −24 |
| Example 14 | $Cr_2O_3$ | $CeO_2$ (12 mol %)-$ZrO_2$ | 90 | ⊚ | −11 |
| Com. Ex. 7 | $Cr_2O_3$ | No | 96 | ○ | −68 |
| Example 15 | $NiCr_2O_4$ | $Y_2O_3$ (8 mol %)-$ZrO_2$ | 98 | ⊚ | −18 |
| Example 16 | $NiCr_2O_4$ | $CeO_2$ (12 mol %)-$ZrO_2$ | 96 | ⊚ | −14 |
| Com. Ex. 8 | $NiCr_2O_4$ | No | 103 | ○ | −72 |

Note:
* Unit is % by mass.
[1]–[3]The same as in Table 2.

The comparison of Examples 9–16 and Comparative Examples 5–8 revealed that any sensor sample of Examples 9–16 provided with an electrode-coating layer 11' having gas-diffusing pores 14 had a drastically decreased change ratio of the drift of sensitivity as compared with sensor samples of Comparative Examples 5–8 without electrode-coating layers. In addition, the change ratio of drift was except that a 300-μm-thick, high-purity alumina substrate was used as an electric insulating substrate 41, that a zirconia print layer (solid electrolyte substrate layer) 1' containing 6 mol % of yttria was formed thereon, that a NOx-sensing electrode 5 and a reference electrode 7 were then formed on the same surface of the green sheet, and that an electrode-coating layer 11 was screen-printed only on the NOx-sensing electrode 5.

Sensor samples having the structure shown in FIG. 9 were produced, in the same manner as in Reference Example 1 except that after a first NOx-sensing electrode 5a was formed on the zirconia solid electrolyte substrate 1, an electrode-coating layer 11 and a second NOx-sensing electrode 5b were successively screen-printed. The first NOx-sensing electrode 5a and the second NOx-sensing electrode 5b were formed by the same electrode material.

Sensor samples having the structure shown in FIG. 10 were produced, in the same manner as in Reference Example 1 except that after a first NOx-sensing electrode 5a was formed on the zirconia solid electrolyte substrate 1, an electrode-coating layer 11 and a second NOx-sensing electrode 5b were printed, and that a further electrode-coating layer 11 was screen-printed thereon. The first NOx-sensing electrode 5a and the second NOx-sensing electrode 5b were formed by the same electrode material.

With respect to each of the resultant sensor samples, sensitivity was evaluated in the same manner as in Example 1. The results are shown in Table 4. Incidentally, for the comparison of performance, the sensitivity of the sensor samples having the structure shown in FIG. 1 (Examples 6, 8) was also shown in Table 4.

TABLE 4

| No. | Structure | Sensing electrode | Initial Sensitivity[1] (mV) | Gas Response[2] | Change Ratio of Drift[3] (%) |
|---|---|---|---|---|---|
| Ex. 8 | FIG. 1 | $NiCr_2O_4$ | 98 | ◎ | −16 |
| Ex. 6 | FIG. 1 | $Cr_2O_3$ | 91 | ◎ | −14 |
| Ex. 17 | FIG. 3 | $NiCr_2O_4$ | 102 | ◎ | −12 |
| Ex. 18 | FIG. 3 | $Cr_2O_3$ | 96 | ◎ | −11 |
| Ex. 19 | FIG. 4 | $NiCr_2O_4$ | 91 | ◎◎ | −17 |
| Ex. 20 | FIG. 4 | $Cr_2O_3$ | 86 | ◎◎ | −18 |
| Ex. 21 | FIG. 6 | $NiCr_2O_4$ | 97 | ◎ | −16 |
| Ex. 22 | FIG. 6 | $Cr_2O_3$ | 92 | ◎ | −17 |
| Ex. 23 | FIG. 8 | $NiCr_2O_4$ | 96 | ◎ | −18 |
| Ex. 24 | FIG. 8 | $Cr_2O_3$ | 94 | ◎ | −16 |
| Ex. 25 | FIG. 9 | $NiCr_2O_4$ | 95 | ◎◎ | −20 |
| Ex. 26 | FIG. 9 | $Cr_2O_3$ | 87 | ◎◎ | −18 |
| Ex. 27 | FIG. 10 | $NiCr_2O_4$ | 99 | ◎◎ | −18 |
| Ex. 28 | FIG. 10 | $Cr_2O_3$ | 92 | ◎◎ | −16 |

Note:
[1]and[3]The same as in Table 2.
[2]Relative evaluation ◎◎: Extremely Excellent. ◎: Excellent. ○: Fair. Δ: Poor.

As compared with the sensor samples having the structure shown in FIG. 1, the sensor samples having the structure shown in FIG. 3 (Examples 17 and 18) had decreased change ratios of drift, confirming the effect of providing the electrode underlayer 31. Though the sensor samples having the structure shown in FIG. 4 (Examples 19 and 20) slightly decreased in sensitivity, they were excellent in gas response. It is presumed that this effect is obtained by the fact that because of the formation of the electric insulating layer 32, there is an electrode interface, in which a gas detection reaction occurs, on the upper surface of the sensing electrode 5.

The sensor samples having the structure shown in FIG. 6 (Examples 21 and 22) showed substantially the same performance as that of the sensor samples having the structure shown in FIG. 1. This confirmed that the same effect was obtained when the sensing electrode 5 and the reference electrode 7 were formed on one surface of the solid electrolyte substrate 1 and when they were formed on both surfaces thereof.

The sensor samples having the structure shown in FIG. 8 (Examples 23 and 24) showed substantially the same performance as that of the sensor samples having the structure shown in FIG. 6. This confirmed that the same performance was obtained when the thin solid electrolyte substrate layer 1' was formed on the electric insulating substrate 41 and when the solid electrolyte substrate 1 was used.

The sensor samples having the structure shown in FIGS. 9 and 10 (Examples 25–28) were superior to the sensor samples having the structure shown in FIG. 1 in gas response. This is presumed to be due to the fact that the formation of two sensing electrodes increased the electrode interface area. In addition, the sensor samples having the structure shown in FIGS. 9 and 10 were improved in response while substantially maintaining excellent sensitivity and stability, like the sensor samples having the structure shown in FIG. 4.

It is clear from the above results that the sensor samples having the structures of the present invention have small drift of sensitivity and are not only excellent in the stability of sensitivity but also improved in response.

EXAMPLES 29–35

Samples of NOx sensors having the structure shown in FIG. 1 were produced in the same manner as in Reference Example 1 except for using $NiCr_2O_4$ for NOx-sensing electrodes 5, and using zirconia solid electrolyte layers containing 10 mol % of various stabilizers shown in Table 5 for electrode-coating layers 11. The electrode-coating layers 11 of the resultant NOx sensors had a porosity of 30% and an average thickness of 15 μm. Each of the resultant sensor samples was evaluated with respect to performance in the same manner as in Example 1. The results are shown in Table 5. For comparison, the data of Comparative Example 4 are also shown.

TABLE 5

| No. | Electrode-Coating Layer | Initial Sensitivity[1] (mV) | Gas Response[2] | Change Ratio of Drift[3] (%) |
|---|---|---|---|---|
| Example 29 | $Y_2O_3$ (10 mol %)-$ZrO_2$ | 101 | ○ | −21 |
| Example 30 | CaO (10 mol %)-$ZrO_2$ | 91 | ◎ | −38 |
| Example 31 | MgO (10 mol %)-$ZrO_2$ | 95 | ◎ | −19 |
| Example 32 | $CeO_2$ (10 mol %)-$ZrO_2$ | 103 | ◎ | −16 |
| Example 33 | $Sc_2O_3$ (10 mol %)-$ZrO_2$ | 98 | ◎ | −17 |
| Example 34 | $ThO_2$ (10 mol %)-$ZrO_2$ | 86 | ○ | −34 |
| Example 35 | $Yb_2O_3$ (10 mol %)-$ZrO_2$ | 90 | ○ | −29 |
| Com. Ex. 4 | No | 103 | ○ | −72 |

Note:
[1]–[3]The same as in Table 2.

As shown in Table 5, remarkable reduction effect of the change ratio of drift was observed in Examples 29–35 than in Comparative Example 9, irrespective of the materials of the electrode-coating layers 11. Such effect was remarkable particularly when a zirconia solid electrolyte layer containing $Y_2O_3$, MgO, $CeO_2$ or $Sc_2O_3$ as a stabilizer was used.

EXAMPLES 36–42

Samples of the NOx sensors of the present invention having the structure shown in FIG. 3 were produced, in the same manner as in Reference Example 1 except for using $NiCr_2O_4$ for a NOx-sensing electrode 5 and a zirconia solid electrolyte containing 12 mol % of $CeO_2$ for electrode-coating layers 11, using zirconia solid electrolytes containing 10 mol % of various stabilizers shown in Table 6 for an electrode underlayer 31 having a porosity of 10% and a thickness of 3 μm, and screen-printing an electrode underlayer 31, a NOx-sensing electrode 5 and an electrode-coating layer 11 (porosity: 30%, average thickness: 15 μm), respectively, on the solid electrolyte substrate 1. The detection performance of each of the resultant sensor samples was evaluated in the same manner as in Example 1. The results are shown in Table 6.

As shown in Table 6, the sensor samples of Examples 36–42 were remarkably improved in gas response and the suppression of drift irrespective of the materials of the electrode underlayer 31. Particularly when the same $CeO_2$-added zirconia solid electrolyte as in the electrode-coating layer 11 was used for the electrode underlayer 31, the electrode underlayer 31 exhibited large effects.

EXAMPLES 43–54

Samples of NOx sensors having the structure shown in FIG. 1 were produced, in the same manner as in Reference Example 1 except for using metal oxides shown in Table 7 for the NOx-sensing electrode 5, and a zirconia solid electrolyte layer containing 12 mol % of $CeO_2$ (porosity: 30%, average thickness: 15 μm) for the electrode-coating layer 11. Each of the resultant sensor samples was evaluated with respect to performance in the same manner as in Example 1. The results are shown in Table 7.

TABLE 6

| No. | Electrode Underlayer | Initial Sensitivity[1] (mV) | Gas Response[2] | Change Ratio of Drift[3] (%) |
|---|---|---|---|---|
| Example 36 | $Y_2O_3$(10 mol %)-$ZrO_2$ | 102 | ⊙ | −10 |
| Example 37 | CaO(10 mol %)-$ZrO_2$ | 93 | ⊙ | −14 |
| Example 38 | MgO(10 mol %)-$ZrO_2$ | 94 | ⊙ | −10 |
| Example 39 | $CeO_2$(10 mol %)-$ZrO_2$ | 105 | ⊙ | −6 |
| Example 40 | $Sc_2O_3$(10 mol %)-$ZrO_2$ | 99 | ⊙ | −9 |
| Example 41 | $ThO_2$(10 mol %)-$ZrO_2$ | 84 | ⊙ | −13 |
| Example 42 | $Yb_2O_3$(10 mol %)-$ZrO_2$ | 91 | ⊙ | −12 |

Note:
[1]–[3]The same as in Table 2.

TABLE 7

| | | | | Change Ratio of Drift | | |
|---|---|---|---|---|---|---|
| No. | Sensing electrode | Initial Sensitivity[1] (mV) | Gas Response[2] | No Coating Layer $E_0^{(3)}$ (%) | With Coating Layer $E_1^{(3)}$ (%) | $E_1/E_0$ |
| Example 43 | NiO | 72 | Δ | −79 | −38 | 0.48 |
| Example 44 | $WO_3$ | 64 | ○ | −82 | −40 | 0.49 |
| Example 45 | $Cr_2O_3$ | 95 | ⊙ | −68 | −15 | 0.22 |
| Example 46 | $NiCr_2O_4$ | 102 | ⊙ | −72 | −15 | 0.21 |
| Example 47 | $FeCr_2O_4$ | 94 | ⊙ | −75 | −19 | 0.25 |
| Example 48 | $MgCr_2O_4$ | 93 | ○ | −73 | −17 | 0.23 |
| Example 49 | $CrMnO_3$ | 75 | ○ | −75 | −22 | 0.29 |
| Example 50 | $CrWO_4$ | 69 | ○ | −78 | −25 | 0.32 |
| Example 51 | $LaCrO_3$ | 62 | ○ | −81 | −27 | 0.33 |
| Example 52 | $NiTiO_3$ | 43 | Δ | −85 | −36 | 0.42 |
| Example 53 | $FeTiO_3$ | 50 | Δ | −83 | −34 | 0.41 |
| Example 54 | $ZnFe_2O_4$ | 65 | Δ | −85 | −33 | 0.39 |

Note:
[1]–[2]The same as in Table 2.
[3]The same as in Table 2.

As shown in Table 7, when metal oxides containing Cr as a constituent element were used among the sensing electrode materials, NOx sensors with small change ratios of drift were obtained. Particularly when the NOx-sensing electrode 5 was made of $Cr_2O_3$, $NiCr_2O_4$, $FeCr_2O_4$ or $MgCr_2O_4$, there was a large effect of reducing the change ratio of drift.

EXAMPLES 55–66

Samples of NOx sensors having the structure shown in FIG. 1 were produced, in the same manner as in Reference Example 1 except for using $NiCr_2O_4$ for the NOx-sensing electrode 5 and a zirconia solid electrolyte layer containing 12 mol % of $CeO_2$ (porosity: 30%, average thickness: 15 μm) for the electrode-coating layer 11. As shown in Table 8, the first precious metal (in the group B) active with NOx and oxygen, the second precious metal (in the group A) active with only oxygen, or Pt—Rh (3% by mass), an alloy of the first and second precious metals (in the group B'), was added to the electrode-coating layer 11 in an amount of 1.0% by mass. The detection performance of each of the resultant sensor samples was evaluated in the same manner as in Example 1. The results are shown in Table 8.

shown in FIG. 1 was produced, in the same manner as in Reference Example 1, except that after a NOx-sensing electrode 5 was formed on a green sheet for the solid electrolyte substrate 1, an electrode-coating layer 11 was formed by a screen-printing method. The sensor sample having the structure shown in FIG. 2 was produced in the same manner as in Reference Example 1, except that after a NOx-sensing electrode 5 was formed on a green sheet for the solid electrolyte substrate 1, a zirconia solid electrolyte sheet containing 6 mol % of $Y_2O_3$ was punched to form an electrode-coating layer 11' having gas-diffusing pores 14 having Sh/Se of about 0.2, laminating the electrode-coating layer 11' on the solid electrolyte substrate 1 such that it covered the sensing electrode 5, and pressing the resultant laminate to bond the substrate layers. The thickness of the electrode-coating layers 11, 11' was changed to various levels as shown in Table 9. The detection performance of each of the resultant sensor samples was evaluated in the same manner as in Example 1. The results are shown in Table 9.

TABLE 8

| No. | Precious Metal in Electrode-Coating Layer | | Initial Sensitivity[1] (mV) | Gas Response[2] | Change Ratio of Drift[3] (%) |
|---|---|---|---|---|---|
| Example 55 | No | | 102 | ○ | −15 |
| Example 56 | A | Pt | 90 | ◉ | −8 |
| Example 57 | | Pd | 86 | ◉ | −11 |
| Example 58 | | Pt—Pd (10% by mass) | 91 | ◉ | −12 |
| Example 59 | | Pd—Ru (5% by mass) | 97 | ◉ | −14 |
| Example 60 | B | Ir | 103 | ○ | −10 |
| Example 61 | | Au | 105 | ○ | −11 |
| Example 62 | | Rh | 109 | ○ | −9 |
| Example 63 | | Ir—Au (10% by mass) | 103 | ○ | −13 |
| Example 64 | | Ir—Rh (5% by mass) | 106 | ○ | −11 |
| Example 65 | | Au—Rh (5% by mass) | 108 | ○ | −15 |
| Example 66 | B' | Pt—Rh (3% by mass) | 112 | ○ | −16 |

Note:
[1]–[3]The same as in Table 2.

As shown in Table 8, as compared with the sample (Example 55) in which the electrode-coating layer 11 did not contain a precious metal, the samples containing the second precious metals in the group A had greatly improving gas response while suppressing the drift, though they exhibited slightly decreased sensitivity. The samples containing the first precious metals in the group B had the same or improved gas sensitivity while suppressing the drift, though there was no improvement in gas response. The sample containing Pt—Rh, an alloy of the first and second precious metals, was improved in sensitivity and its response while suppressing the drift.

EXAMPLES 67 AND 68

Samples of NOx sensors having the structures shown in FIGS. 1 and 2 were produced, in the same manner as in Example 1 except for using $NiCr_2O_4$ for the NOx-sensing electrode 5, and a zirconia solid electrolyte layer (average thickness: 20 μm) containing 12 mol % of $CeO_2$ for the electrode-coating layer 11, 11'. The electrode-coating layer 11 was a porous layer having a porosity of 40%, while the electrode-coating layer 11' was a dense layer having a porosity of 0.5%. The sensor sample having the structure

TABLE 9

| No. | | Thickness[4] of Electrode-Coating Layer[5] (μm) | Initial Sensitivity[1] (mV) | Gas Response[2] | Change Ratio of Drift[3] (%) |
|---|---|---|---|---|---|
| Com. Ex. 4 | | 0 | 103 | ○ | −72 |
| Example 67 | | 1.9 | 93 | ○ | −48 |
| | | 2.8 | 89 | ◉ | −24 |
| | | 5.6 | 88 | ◉ | −21 |
| | | 10.8 | 86 | ◉ | −19 |
| | | 20.5 | 88 | ◉ | −17 |
| | | 28.4 | 82 | ○ | −16 |
| | | 34.1 | 75 | Δ | −17 |
| Example 68 | | 3.5 | 94 | ○ | −46 |
| | | 5 | 93 | ◉ | −21 |
| | | 26 | 95 | ◉ | −17 |
| | | 51 | 92 | ◉ | −16 |
| | | 72 | 90 | ◉ | −15 |
| | | 105 | 88 | ◉ | −16 |
| | | 155 | 73 | Δ | −15 |

Note:
[1]–[3]The same as in Table 2.
[4]Values measured by decomposing the samples after the evaluation.
[5]The electrode-coating layers of Example 67 and Comparative Example 4 were porous (FIG. 1), while the electrode-coating layers of Example 68 were provided with diffusion pores (FIG. 2).

As is clear from the comparison of Example 67 with Comparative Example 10 and the comparison of Example 68 with Comparative Example 11, any of the porous electrode-coating layers 11 and the electrode-coating layers 11' with gas-diffusing pores was improved in any of initial sensitivity, gas response and the change ratio of drift, when they had a proper thickness. It is clear that in the case of the porous electrode-coating layer 11, its thickness is preferably 2.8–20.5 μm, and that in the case of the electrode-coating layer 11' with gas-diffusing pores, its thickness is preferably 5–105 μm.

EXAMPLES 69 AND 70

Samples of NOx sensors having the structure shown in FIG. 1 were produced, in the same manner as in Example 67 except that the thickness of the electrode-coating layer 11 was as constant as about 5 μm, and that its porosity was changed as shown in Table 10. Also, samples of NOx sensors having the structure shown in FIG. 2 were produced, in the same manner as in Example 68 except that the dense electrode-coating layer 11' (porosity: 0.5%) having 50 gas-diffusing pores 14 had a constant thickness of about 50 μm, and that a ratio of (Sh/Se) of the total opening area (Sh) of the gas-diffusing pores 14 to the area (Se) of the sensing electrode 5 was changed as shown in Table 10. By evaluating the detection performance of these sensor samples in the same manner as in Example 1, the influence of the porosity of the porous electrode-coating layer 11 on sensor characteristics (Example 69), and the influence of Sh/Se of the electrode-coating layer 11' with gas-diffusing pores on sensor characteristics (Example 70) were examined. The evaluation results of Example 69 are shown in Table 10, and the evaluation results of Example 70 are shown in Table 11.

COMPARATIVE EXAMPLES 9 and 10

Samples of NOx sensors (gas-detecting elements) were produced to evaluate detection performance in the same manner as in Example 69 except that the porosity of the porous electrode-coating layer 11 was 4% and 59%, respectively. The results are shown in Table 10.

COMPARATIVE EXAMPLES 11 and 12

Samples of NOx sensors were produced to evaluate detection performance in the same manner as in Example 70 except that the Sh/Se of the electrode-coating layer 11' having gas-diffusing pores 14 was 3% and 33%, respectively. The results are shown in 11.

TABLE 10

| No. | Porosity (%) | Initial Sensitivity[1] (mV) | Gas Response[2] | Change Ratio of Drift[3] (%) |
|---|---|---|---|---|
| Com. Ex. 9 | 4 | X[4] | X[4] | X[4] |
| Example 69 | 10 | 86 | ○ | −17 |
|  | 22 | 89 | ◎ | −19 |
|  | 31 | 91 | ◎ | −16 |
|  | 38 | 88 | ◎ | −19 |
|  | 51 | 85 | ◎ | −23 |
| Com. Ex. 10 | 59 | 82 | ○ | −49 |

Note:
[1]–[3]The same as in Table 2.
[4]Could not be measured.

TABLE 11

| No. | Sh/Se (%) | Initial Sensitivity[1] (mV) | Gas Response[2] | Change Ratio of Drift[3] (%) |
|---|---|---|---|---|
| Com. Ex. 11 | 3 | 74 | Δ | −19 |
| Example 70 | 5 | 92 | ○ | −16 |
|  | 12 | 90 | ◎ | −18 |
|  | 16 | 93 | ◎ | −16 |
|  | 23 | 92 | ◎ | −19 |
|  | 28 | 92 | ◎ | −22 |
| Com. Ex. 12 | 33 | 84 | ○ | −36 |

Note:
[1]–[3]The same as in Table 2.

As shown in Tables 10 and 11, there are optimum ranges, for sensor characteristics, in both of the porosity of the porous electrode-coating layer 11 and the Sh/Se of the electrode-coating layer 11' with gas-diffusing pores, respectively. In the case of the porous electrode-coating layer 11, good sensitivity and stability are obtained when the porosity is in a range of 10–51%, and response is improved when the porosity is restricted to 22–51%. On the other hand, in the case of the electrode-coating layer 11' with gas-diffusing pores, excellent sensitivity and stability are obtained when the Sh/Se is in a range of 5–28%, and response is improved when the Sh/Se is restricted to 12–28%.

EXAMPLES 71–83, COMPARATIVE EXAMPLES 13, 14

Samples of NOx gas-detecting elements (NOx sensors) shown in FIGS. 11 and 12 were produced. Zirconia solid electrolyte green sheets of 5 mm×5 mm×0.25 mm were produced using zirconia powder containing 6 mol % of yttria by a doctor blade method. Each of the resultant green sheets was screen-printed with a Pt lead conductor, a NOx-sensing electrode 5, a reference electrode 7 and an electrode-coating layer 12. The NOx-sensing electrode 5 was made of $NiCr_2O_4$, and its size was 2 mm×2 mm×0.003 mm. The reference electrode 7 was made of Pt or an alloy of Pt containing 1% by mass of Rh, and screen-printed on a surface of the zirconia solid electrolyte substrate 1 opposing the NOx-sensing electrode 5. The material, shape and porosity of the reference electrode 7 and the electrode-coating layer 12 covering the reference electrode 7 are as shown in Table 12.

It is known that though Pt per se has substantially no activity with NOx, alloys of Pt+1% by mass Rh are active with NOx. Accordingly, to examine whether or not the reference electrode 7 becomes inactive with NOx when the electrode-coating layer 12 is formed, a Pt—Rh alloy was used for the reference electrode 7.

Samples of gas-detecting elements each having a reference electrode 7 formed by Pt or Pt+1% by mass Rh with no electrode-coating layer were produced in Comparative Examples 16, 17. The reference electrode 7 had a size of 2 mm×2 mm×0.003 mm.

A green sheet laminate for each gas-detecting element was degreased at 500° C. for 2 hours in air, and sintered at 1400° C. for 3 hours in air. Lead wires were connected to each of the resultant sintered bodies to provide samples of NOx sensors.

Each sensor sample thus produced was set in a quartz pipe and held in an electric furnace, in which the NOx-sensing electrode 5 and the reference electrode 7 were exposed to a detection gas containing 100 ppm of $NO_2$ and 5% by volume of oxygen, the balance being nitrogen, to examine its activity with NOx. The electric furnace was controlled at an atmosphere temperature of 600° C. The output of each sample was measured by a voltmeter with high input impedance, and the sensitivity of each sample was evaluated by the difference in output between a base gas containing 5% by volume of oxygen, the balance being nitrogen, and a detection gas (obtained by adding 100 ppm of $NO_2$ to the base gas). Interface impedance between the reference electrode 7 and the solid electrolyte substrate 1 was measured by an impedance analyzer. The results are shown in Table 13.

sensitivity corresponding to potential difference between both electrodes becomes smaller accordingly.

Examined in Example 71 were the characteristics of the gas-detecting element sample having an electrode-coating layer 12 made of porous ceria-stabilized zirconia on a Pt reference electrode 7. The sample of Example 71 had interface impedance of 10 kΩ, which was about half of that of Comparative Example 1 free from an electrode-coating layer 12, and as large sensitivity as 110 mV. It is presumed that though pure Pt had substantially no sensitivity to NOx, the Pt electrode of the gas-detecting element of Comparative

TABLE 12

| No. | Reference Electrode | Electrode-Coating Layer | | |
|---|---|---|---|---|
| | | Material | Size (mm) | Porosity (vol. %) |
| Com. Ex. 13 | Pt | No | — | — |
| Com. Ex. 14 | Pt-1% by mass Rh | No | — | — |
| Ex. 71[1] | Pt | $CeO_2$ (12 mol %)-$ZrO_2$ | 3 × 3 × 0.01 | 30 |
| Ex. 72[1] | Pt-1% by mass Rh | $CeO_2$ (12 mol %)-$ZrO_2$ | 3 × 3 × 0.01 | 30 |
| Ex. 73[1] | Pt-1% by mass Rh | $Y_2O_3$ (8 mol %)-$ZrO_2$ | 3 × 3 × 0.01 | 30 |
| Ex. 74[1] | Pt-1% by mass Rh | MgO (15 mol %)-$ZrO_2$ | 3 × 3 × 0.01 | 30 |
| Ex. 75[1] | Pt-1% by mass Rh | $Sc_2O_3$ (12 mol %)-$ZrO_2$ | 3 × 3 × 0.01 | 30 |
| Ex. 76[1] | Pt-1% by mass Rh | $CeO_2$ (12 mol %)-$ZrO_2$ | 3 × 3 × 0.01 | 10 |
| Ex. 77[1] | Pt-1% by mass Rh | $CeO_2$ (12 mol %)-$ZrO_2$ | 3 × 3 × 0.01 | 20 |
| Ex. 78[1] | Pt-1% by mass Rh | $CeO_2$ (12 mol %)-$ZrO_2$ | 3 × 3 × 0.01 | 50 |
| Ex. 79[1] | Pt-1% by mass Rh | $CeO_2$ (12 mol %)-$ZrO_2$ | 3 × 3 × 0.003 | 30 |
| Ex. 80[1] | Pt-1% by mass Rh | $CeO_2$ (12 mol %)-$ZrO_2$ | 3 × 3 × 0.015 | 30 |
| Ex. 81[1] | Pt-1% by mass Rh | $CeO_2$ (12 mol %)-$ZrO_2$ | 3 × 3 × 0.02 | 30 |
| Ex. 82[2] | Pt-1% by mass Rh | $CeO_2$ (12 mol %)-$ZrO_2$ | 2.5 × 3 × 0.005 | 0 |
| Ex. 83[2] | Pt-1% by mass Rh | $Y_2O_3$ (3 mol %)-$ZrO_2$ | 2.5 × 3 × 0.005 | 0 |

Note:
[1]The gas-detecting element shown in FIG. 11, in which the reference electrode was completely covered by a porous electrode-coating layer.
[2]The gas-detecting element shown in FIG. 12, in which the reference electrode was covered by a dense electrode-coating layer excluding one side surface thereof.

TABLE 13

| No. | Sensitivity to 100 ppm of $NO_2$ (mV) | Interface Impedance (kΩ) |
|---|---|---|
| Com. Ex. 13 | 103 | 20 |
| Com. Ex. 14 | 75 | 50 |
| Example 71[1] | 110 | 10 |
| Example 72[1] | 97 | 25 |
| Example 73[1] | 98 | 24 |
| Example 74[1] | 95 | 26 |
| Example 75[1] | 94 | 27 |
| Example 76[1] | 100 | 23 |
| Example 77[1] | 98 | 24 |
| Example 78[1] | 95 | 27 |
| Example 79[1] | 95 | 25 |
| Example 80[1] | 98 | 26 |
| Example 81[1] | 99 | 24 |
| Example 82[2] | 101 | 21 |
| Example 83[2] | 102 | 20 |

Note:
[1],[2]The same as in Table 2.

The sample of Comparative Example 16 having a reference electrode 7 made of Pt had sensitivity of 103 mV to 100 ppm of $NO_2$, and interface impedance of 20 kΩ. The sample of Comparative Example 17 having a reference electrode 7 made of an alloy of Pt and 1% by mass of Rh active with NOx had as large interface impedance as 50 kΩ, and as small sensitivity as 75 mV. This is presumed to be due to the fact that because the potential of an electrode made of an alloy of Pt and 1% by mass of Rh is about 30 mV in the same direction as the potential of the NOx-sensing electrode 5, the Example 1 that did not have an electrode-coating layer 12 became active with NOx by contamination, etc. during its production processes, resulting in decrease in sensitivity. On the other hand, why the sensitivity is higher in Example 71 than in Comparative Example 1 is presumed to be due to the fact that the coating layer 12 formed on the Pt electrode suppressed contamination during the production processes, thereby keeping the activity with NOx substantially zero.

Examined in Examples 72–75 was the influence of a stabilizer added to an electrode-coating layer 12 made of a zirconia solid electrolyte. In any Examples, the reference electrode 7 was made of an alloy of Pt and 1% by mass of Rh, and the porous electrode-coating layer 12 having a size of 3 mm×3 mm×0.01 mm and a porosity of 30% by volume completely covered the reference electrode 7. Though there are some differences in interface impedance and sensitivity depending on the types of stabilizers, any of Examples 72–75 exhibited smaller interface impedance with larger sensitivity by about 20 mV than Comparative Example 2. This is presumed to be due to the fact that because the detection gas in this Example had a sufficiently high oxygen concentration as compared with the concentration of NOx, a detection object gas, decrease in the interface impedance results in increase only in the reaction sites of oxygen without substantially changing the reaction sites of NOx, the activity of the reference electrode to NOx decreased.

In Examples 72 and 76–78, the influence of the porosity of electrode-coating layer 12 was examined. In any Examples, the electrode-coating layer 12 having a size of 3 mm×3 mm×0.01 mm completely covered the reference electrode 7. When the electrode-coating layer 12 had porosity in a range of 10–50%, they exhibited substantially the same interface impedance as that of Comparative Example 2 and larger sensitivity than that of Comparative Example 2 by about 20 mV or more, confirming that the activity of the reference electrode 7 to NOx was decreased.

In Examples 72 and 79–81, the influence of the thickness of the porous electrode-coating layer 12 was examined. Within the thickness range of these Examples, they exhibited substantially the same interface impedance as that of Comparative Example 17 and larger sensitivity than that of Comparative Example 17 by 20 mV or more, confirming that the activity of the reference electrode 7 to NOx was decreased.

Examined in Examples 82 and 83 was the sensitivity of sensor elements having the structure shown in FIG. 12, when a dense electrode-coating layer 12 was laminated on a reference electrode 7. Used for the electrode-coating layer 12 was zirconia stabilized by 12 mol % of ceria in Example 82, and zirconia stabilized by 3 mol % of yttria in Example 83. In any Examples, the electrode-coating layer 12 had a size of 2.5 mm×3 mm×0.005 mm, and was not formed on one of the four side surfaces of the reference electrode 7. The interface impedance was 21 kΩ in Example 82 and 20 kΩ in Example 83, remarkably smaller than that of Comparative Example 17. The sensitivity to 100 ppm of $NO_2$ was 101 mV in Example 82, larger than that of Comparative Example 17 by 26 mV, and 102 mV in Example 83, larger than that of Comparative Example 17 by 27 mV. This proved that the activity of the reference electrode 7 to NOx was decreased by the dense electrode-coating layer 12. Substantially no deterioration in response was observed by the dense coating layer 12.

EXAMPLES 84, 85, COMPARATIVE EXAMPLES 15, 16

Samples of NOx sensors having the structure shown in FIG. 7 were produced, in the same manner as in Reference Example 1 except that $Cr_2O_3$ or $NiCr_2O_4$ was used for a NOx-sensing electrode 5, that Pt was used for a reference electrode 7, that a zirconia solid electrolyte containing 12 mol % of $CeO_2$ was used for electrode-coating layers 11, 12, and that electrode-coating layers 11, 12 (porosity: 30%, average thickness: 15 μm) were screen-printed on the NOx-sensing electrode 5 and the reference electrode 7. The performance of the resultant samples was measured in the same manner as in Examples 17–28. Also, with respect to the sensor samples of Comparative Examples 15, 16, which were the same as those of Examples 84, 85 except that no electrode-coating layer was formed on any of the NOx-sensing electrode and the reference electrode, performance was measured in the same manner as in Examples 17–28. The results are shown in Table 14.

For comparison, the measurement results of the sensor samples shown in FIG. 6 (Examples 21, 22), in which the electrode-coating layer 11 was formed only on the NOx-sensing electrode were also shown in Table 14.

TABLE 14

| No. | Structure | Sensing electrode | Initial Sensitivity[1] (mV) | gas Response[2] | Change Ratio of Drift[3] (%) |
|---|---|---|---|---|---|
| Example 84 | FIG. 7 | $NiCr_2O_4$ | 96 | ○ | −12 |
| Example 85 | FIG. 7 | $Cr_2O_3$ | 93 | ○ | −13 |
| Com. Ex. 15 | — | $NiCr_2O_4$ | 103 | — | −73 |
| Com. Ex. 16 | — | $Cr_2O_3$ | 96 | — | −68 |
| Example 21 | FIG. 6 | $NiCr_2O_4$ | 97 | ○ | −16 |
| Example 22 | FIG. 6 | $Cr_2O_3$ | 92 | ○ | −17 |

Note:
[1]–[3] The same as in Table 2.

It was found that the sensor samples having the structure shown in FIG. 7 (Examples 84 and 85) had a decreased change ratio of drift than that of the sample having the structure shown in FIG. 6. This is presumed to be due to the fact that the stabilization of the reference electrode 7 contributed to decrease in the drift of sensor output.

EXAMPLES 86–94

Samples of laminate-type NOx gas-detecting devices having the structures shown in FIGS. 14 and 15 were produced. $Cr_2O_3$ or $NiCr_2O_4$ was used for a NOx-sensing electrode 5, and a zirconia solid electrolyte layer containing 12 mol % of $CeO_2$ (porosity: 30%, average thickness 15 μm) or a zirconia solid electrolyte layer containing 8 mol % of $Y_2O_3$ (porosity: 30%, average thickness 15 μm) was used for electrode-coating layers 11, 12. Samples having electrode-coating layers 11, to which Rh (a first precious metal) and/or Pt (a second precious metal) was added in an amount of 0.5% by mass based on the electrode-coating layer, were also produced. A green sheet for the solid electrolyte substrate 1 was produced by a doctor blade method using zirconia powder containing 6 mol % of yttria.

Formed on the green sheet I for the solid electrolyte substrate 1 by a screen-printing method to form a NOx-detecting cell were a NOx-sensing electrode 5, a Pt reference electrode 7, electrode-coating layers 11, 12, and Pt lead conductors. Also, a green sheet II having the same composition was screen-printed with a NOx-converting electrode 8 made of Pt—Rh and a conversion counter electrode 9 made of Pt, to form a NOx-converting pump element. Further, a heater was sandwiched by two green sheets III having the same composition to form a heater portion. These green sheets I–III were laminated with green sheets for forming air ducts, and green sheets for forming the air ducts, spacers and a gas inlet.

With portions for forming internal spaces (a gas-measuring chamber, air ducts, etc.) filled with theobromine, which was sublimed at a degreasing step, each laminate was pressed while heating. After each laminate was degreased, it was at sintered 1400° C. Each of the resultant sintered laminates was provided with lead wires to constitute a laminate-type NOx sensor.

Each laminate-type NOx sensor sample was connected to a control unit, set in a quartz pipe and held in an electric furnace. A detection gas containing 50 ppm of NO, 50 ppm of $NO_2$ and 5% by volume oxygen, the balance being nitrogen was caused to flow through the quartz pipe. With the atmosphere temperature of the electric furnace controlled to 600° C., the NOx-detecting performance of each sensor sample was evaluated while applying a predetermined potential to the conversion pump element in the same manner as in Example 1. The compositions of the electrodes are shown in Table 15, and the measurement results are shown in Table 16.

COMPARATIVE EXAMPLES 17, 18

Laminate-type sensor samples were produced to evaluate their detection performance, in the same manner as in Examples 86–94 except that an electrode-coating layer was not formed. The compositions of the electrodes are shown in Table 15, and the measurement results are shown in Table 16.

TABLE 15

| | | | Electrode-Coating Layer | |
| --- | --- | --- | --- | --- |
| No. | Sensing electrode | Metal Oxide | First Precious Metal | Second Precious Metal |
| Example 86 | $Cr_2O_3$ | $CeO_2$(12 mol %)-$ZrO_2$ | Rh | No |
| Example 87 | $Cr_2O_3$ | $CeO_2$(12 mol %)-$ZrO_2$ | No | Pt |
| Example 88 | $Cr_2O_3$ | $CeO_2$(12 mol %)-$ZrO_2$ | Rh | Pt |
| Com. Ex. 17 | $Cr_2O_3$ | No | No | No |
| Example 89 | $NiCr_2O_4$ | $CeO_2$(12 mol %)-$ZrO_2$ | Rh | No |
| Example 90 | $NiCr_2O_4$ | $CeO_2$(12 mol %)-$ZrO_2$ | No | Pt |
| Example 91 | $NiCr_2O_4$ | $CeO_2$(12 mol %)-$ZrO_2$ | Rh | Pt |
| Com. Ex. 18 | $NiCr_2O_4$ | No | No | No |
| Example 92 | $Cr_2O_3$ | $Y_2O_3$(8 mol %)-$ZrO_2$ | Rh | No |
| Example 93 | $Cr_2O_3$ | $Y_2O_3$(8 mol %)-$ZrO_2$ | No | Pt |
| Example 94 | $Cr_2O_3$ | $Y_2O_3$(8 mol %)-$ZrO_2$ | Rh | Pt |

TABLE 16

| | Element of FIG. 14 | | Element of FIG. 15 | |
| --- | --- | --- | --- | --- |
| No. | Initial Sensitivity[1] (mV) | Change Ratio of Drift[2] (%) | Initial Sensitivity[1] (mV) | Change Ratio of Drift[2] (%) |
| Example 86 | 40 | −26 | 38 | −29 |
| Example 87 | 38 | −22 | 36 | −20 |
| Example 88 | 42 | −18 | 40 | −19 |
| Com. Ex. 17 | 37 | −49 | 35 | −54 |
| Example 89 | 41 | −28 | 41 | −29 |
| Example 90 | 43 | −20 | 42 | −23 |
| Example 91 | 40 | −22 | 38 | −20 |
| Com. Ex. 18 | 42 | −51 | 33 | −56 |
| Example 92 | 42 | −28 | 39 | −25 |
| Example 93 | 40 | −19 | 39 | −24 |
| Example 94 | 39 | −19 | 36 | −23 |

Note:
[1]Expressed by the difference between a sensor output obtained in the case of an $N_2$ base gas containing 5% by volume of oxygen, and a sensor output obtained in the case of a gas formulated by adding 50 ppm of NO and 50 ppm of $NO_2$ to the base gas.
[2]Expressed by the difference (degree of change) between an initial sensitivity to 50 ppm of NO and 50 ppm of $NO_2$ and sensitivity to 50 ppm of NO and 50 ppm of $NO_2$ after the accelerated deterioration test. "+" means the increase in sensitivity, and "−" means the decrease in sensitivity.

As shown in Table 16, any laminate-type sensor structures can be provided with drastically decreased change ratios of drift by forming electrode-coating layers, like the single layer sensor (element structure, etc. shown in FIG. 1) in Example 1, etc.

EXAMPLES 95–110, COMPARATIVE EXAMPLE 19

Gas-detecting devices (laminate-type NOx sensors) having the structure shown in FIGS. 15–18 were produced. Green sheets of 6 mm×70 mm for solid electrolyte substrates were produced from zirconia powder containing 6 mol % of yttria by a doctor blade method. The thickness of each green sheet was 0.1–0.3 mm, though it changed depending on portions. Each green sheet was screen-printed with Pt lead conductors, a NOx sensing electrode, a reference electrode, an oxygen-sensing electrode and its electrode-coating layer, a NOx-converting electrode, a NOx-converting counter electrode, a gas-treating electrode, and a heater. These green sheets were laminated, degreased at 500° C. for 2 hours, and sintered at 1400° C. for 3 hours in the air to provide samples.

The NOx-sensing electrode 5 was made of $NiCr_2O_4$, having a size of 0.7 mm×1.3 mm×0.003 mm. The reference electrode 7 shown in FIG. 15 and the oxygen-sensing electrode 6 shown in FIGS. 17 and 18, each having a size of 0.7 mm×1.8 mm×0.005 mm, were made of Pt, an alloy of Pt and 50% by mass of Ir, or an alloy of Pt and 1% by mass of Au, respectively. The reference electrodes 7 shown in FIGS. 17 and 18 were made of Pt, having a size of 0.7 mm×1.3 mm×0.003 mm.

The NOx-converting electrode 8 was made of an alloy of Pt and 3% by mass of Rh, the NOx-converting counter electrode 9 was made of Pt, and the gas-treating electrode 10 was made of Pt. Zirconia stabilized by 10% by mass of yttria (8 mol %) was added to each electrode to produce a gas electrode. The material, size, porosity and form of the electrode-coating layer 12 covering the reference electrode 7 in FIG. 15, and the material, size, porosity and form of the electrode-coating layer 13 covering the oxygen-sensing electrode 6 in FIGS. 17 and 18 are as shown in Table 17.

Each of the resultant sensor samples was charged into an alumina tube, which was set in a measurement jig, which was then assemble din a gas sensitivity evaluation apparatus. Each sensor sample was exposed to a detection gas containing 100 ppm of an NO gas and 5% by volume oxygen, the balance being nitrogen. Voltage of 0.8 V was applied to the NOx-converting pump in such a direction that oxygen is introduced into the gas-measuring chamber, to convert NO to $NO_2$. In the gas-detecting device shown in FIG. 18, a constant voltage of 0.8 V was applied to the gas-treating pump in such a direction that oxygen was introduced into the gas-measuring chamber. The self-heating-type heater was controlled by the signal of a thermocouple embedded in the gas-detecting device, such that the temperature of a detection region was 600° C.

The output of each sample was measured by a voltmeter with high input impedance, and the sensitivity of the device was evaluated by the difference between the output obtained in the case of a base gas containing 5% by volume of oxygen, the balance being nitrogen, and the output obtained in the case of a detection gas containing 100 ppm of NO in addition to the base gas composition. Also, the interface impedance between the reference electrode or the oxygen-sensing electrode each provided with the electrode-coating layer and the solid electrolyte substrate was measured by an impedance analyzer. The results are shown in Table 18.

TABLE 17

| No. | Laminate Sensor Structure | Electrode-Coating Layer Material | Size (mm) | Porosity (vol. %) |
|---|---|---|---|---|
| Com. Ex. 19 | FIG. 15 | No | — | — |
| Example 95[1] | FIG. 15 | $CeO_2$ (12 mol %)-$ZrO_2$ | 1 × 1.8 × 0.01 | 30 |
| Example 96[1] | FIG. 15 | $Y_2O_3$ (8 mol %)-$ZrO_2$ | 1 × 1.8 × 0.01 | 30 |
| Example 97[1] | FIG. 15 | MgO (15 mol %)-$ZrO_2$ | 1 × 1.8 × 0.01 | 30 |
| Example 98[1] | FIG. 15 | $Sc_2O_3$ (12 mol %)-$ZrO_2$ | 1 × 1.8 × 0.01 | 30 |
| Example 99[1] | FIG. 15 | $CeO_2$ (12 mol %)-$ZrO_2$ | 1 × 1.8 × 0.01 | 10 |
| Example 100[1] | FIG. 15 | $CeO_2$ (12 mol %)-$ZrO_2$ | 1 × 1.8 × 0.01 | 20 |
| Example 101[1] | FIG. 15 | $CeO_2$ (12 mol %)-$ZrO_2$ | 1 × 1.8 × 0.01 | 50 |
| Example 102[1] | FIG. 15 | $CeO_2$ (12 mol %)-$ZrO_2$ | 1 × 1.8 × 0.01 | 30 |
| Example 103[1] | FIG. 15 | $CeO_2$ (12 mol %)-$ZrO_2$ | 1 × 1.8 × 0.015 | 30 |
| Example 104[1] | FIG. 15 | $CeO_2$ (12 mol %)-$ZrO_2$ | 1 × 1.8 × 0.02 | 30 |
| Example 105[2] | FIG. 15 | $CeO_2$ (12 mol %)-$ZrO_2$ | 0.7 × 1.8 × 0.005 | 0 |
| Example 106[2] | FIG. 17 | $CeO_2$ (12 mol %)-$ZrO_2$ | 0.7 × 1.8 × 0.005 | 0 |
| Example 107[2] | FIG. 18 | $CeO_2$ (12 mol %)-$ZrO_2$ | 0.7 × 1.8 × 0.005 | 0 |
| Example 108[2] | FIG. 18 | $Y_2O_3$ (3 mol %)-$ZrO_2$ | 0.7 × 1.8 × 0.005 | 0 |
| Example 109[2] | FIG. 18 | $Y_2O_3$ (3 mol %)-$ZrO_2$ | 0.7 × 1.8 × 0.005 | 0 |
| Example 110[2] | FIG. 18 | $Y_2O_3$ (3 mol %)-$ZrO_2$ | 0.7 × 1.8 × 0.005 | 0 |

Note:
[1]Gas-detecting element shown in FIG. 11, in which the reference electrode was completely covered by a porous electrode-coating layer.
[2]Gas-detecting element shown in FIG. 12, in which the reference electrode was covered by a dense electrode-coating layer excluding one side surface thereof.

TABLE 18

| No. | Oxygen Electrode[3] | Sensitivity to 100 ppm of NO (mV) | Interface Impedance (kΩ) |
|---|---|---|---|
| Com. Ex. 19 | Pt | 30 | 40 |
| Example 95[1] | Pt | 42 | 20 |
| Example 96[1] | Pt | 41 | 22 |
| Example 97[1] | Pt | 39 | 24 |
| Example 98[1] | Pt | 40 | 23 |
| Example 99[1] | Pt | 43 | 19 |
| Example 100[1] | Pt | 43 | 19 |
| Example 101[1] | Pt | 38 | 22 |
| Example 102[1] | Pt | 39 | 24 |
| Example 103[1] | Pt | 42 | 22 |
| Example 104[1] | Pt | 42 | 22 |
| Example 105[2] | Pt | 46 | 18 |
| Example 106[2] | Pt | 47 | 18 |
| Example 107[2] | Pt | 45 | 20 |
| Example 108[2] | Pt | 45 | 19 |
| Example 109[2] | Pt-50% by mass Ir | 46 | 20 |
| Example 110[2] | Pt-1% by mass Au | 43 | 23 |

Note:
[1],[2]The same as in Table 17.
[3]Reference electrode or oxygen-sensing electrode.

In the sensor of Comparative Example 19 having a sensing electrode 5 and a reference electrode 7 both not provided with an electrode-coating layer as shown in FIG. 15, the sensitivity to 100 ppm of NO was 30 mV, and the interface impedance was 40 kΩ. On the other hand, in the sensors of Examples each having a reference electrode laminated with an electrode-coating layer, the interface impedance was reduced to about 20 kΩ, and its sensitivity was as large as about 40 mV or more.

The reasons therefor are as follows:
(1) By laminating the electrode-coating layer 12, the reference electrode 7 was provided with decreased interface impedance, resulting in decrease in activity with NOx.
(2) Because Theobromine embedded in a portion of the laminate corresponding to the gas-measuring chamber 4 in the lamination process is sublimed with rapid volume expansion at the degreasing step, Rh is not transferred as a contamination component from the NOx-converting electrode 8 disposed at an position opposing the reference electrode 7 because of the sensor structure to the reference electrode 7, so that no activity with NOx is generated in the reference electrode 7.
(3) The lamination of an electrode-coating layer 12 prevents such contamination component from reaching the three-phase interface of the reference electrode 7, so that activity with NOx was not generated in the reference electrode 7, resulting in increase in sensitivity.

Thus, by laminating the electrode-coating layer 12 made of an oxygen-ion-conductive solid electrolyte onto the reference electrode 7, the reference electrode 7 is not easily subjected to influence by the NOx concentration in the detection gas, thereby providing a sensor capable of detecting the NOx concentration with high precision.

In Examples 95–98, the influence of materials, particularly zirconia stabilizers, of the electrode-coating layers 12 of the sensors shown in FIG. 15 was examined. The layer 12 had a size of 1 mm×1.8 mm×0.01 mm and a porosity of 30% by volume, and the reference electrode 7 was completely covered by the electrode-coating layer 12. Whatever stabilizers were added, the interface impedance decreased and the sensitivity increased by about 10 mV as compared with Comparative Example 19. This confirmed that the activity of the reference electrode 7 to NOx was decreased.

In Examples 95 and 99–101, the influence of the porosity of the electrode-coating layers 12 in the sensors shown in FIG. 15 was examined. Each electrode-coating layer 12 had a size of 1 mm×1.8 mm×0.01 mm and completely covered each reference electrode 7. Within this range of porosity, they had smaller interface impedance than that of Comparative Example 1, and larger sensitivity by about 10 mV than that of Comparative Example 19. This confirmed that the activity of the reference electrode 7 to NOx was decreased.

In Examples 95 and 102–104, the influence of the thickness of the porous electrode-coating layer in the sensors shown in FIG. 15 was examined. Each electrode-coating layer 12 had an area of 1 mm×1.8 mm and completely covered the reference electrode 7. Within this range of thickness, they had smaller interface impedance than that of Comparative Example 19, and larger sensitivity by about 10 mV than that of Comparative Example 19. This confirmed that the activity of the reference electrode 7 to NOx was decreased.

In Example 105, the characteristics of the sensor shown in FIG. 15 were examined, when the reference electrode 7 was laminated with an electrode-coating layer 12 constituted by dense ceria-stabilized zirconia, and when only a vertical side surface of the reference electrode 7 was not covered by the electrode-coating layer 12. The sensors showed remarkably decreased interface impedance than that of Comparative Example 19, and sensitivity of 46 mV to 100 ppm of NO, 16 mV increase than Comparative Example 19. This confirmed that the activity of the reference electrode 7 to NOx was decreased. Though it was suspected that the sensors might show a decreased response speed because the coating layer 12 was dense, there was no substantial difference in response as compared with when the porous electrode-coating layer was used.

In Examples 106 and 107, the effect of the coating layers 13 on the oxygen-sensing electrode 6 in the sensors shown in FIGS. 17 and 18, respectively, was examined. Examples 106 and 107 showed the same sensitivity and interface impedance as those of Example 105. This confirmed that the activity of the reference electrode 7 to NOx was decreased.

In Example 108, the characteristics of the sensor shown in FIG. 18 were examined, when the oxygen-sensing electrode 6 was laminated with the electrode-coating layer 13 constituted by dense zirconia stabilized by 3 mol % of yttria, and when a vertical side surface of the oxygen-sensing electrode 6 was not covered by the electrode-coating layer 13. Other electrodes than the oxygen-sensing electrode 6 were not laminated with electrode-coating layers. Example 108 showed the same sensitivity and interface impedance as those of Example 105. This confirmed that the activity of the oxygen-sensing electrode 6 to NOx was decreased.

In Examples 109 and 110, the influence of materials of the oxygen-sensing electrode 6 of the sensor shown in FIG. 18 was examined, when the oxygen-sensing electrode 6 was laminated with the electrode-coating layer 13 constituted by dense zirconia stabilized by 3 mol % of yttria. The electrode-coating layer 13 did not cover a vertical side surface of the oxygen-sensing electrode 6. Other electrodes than the oxygen-sensing electrode 6 were not covered by an electrode-coating layer. The electrode made of an alloy of Pt and 50% by mass of Ir and the oxygen-sensing electrode 6 made of an alloy of Pt and 1% by mass of Au showed the same sensitivity and interface impedance as those of Example 105. This confirmed that these alloys were usable for the oxygen-sensing electrode 6.

It was found that though sensitivity gradually decreased as the using time elapsed in Comparative Example 19, the change of sensitivity with time was remarkably suppressed in any Examples, in which the reference electrode 7 or the oxygen-sensing electrode 6 was covered by an electrode-coating layer made of an oxygen-ion-conductive solid electrolyte. This is presumed to be due to the fact that the electrode-coating layer suppressed contamination during operation, keeping the reference electrode 7 or the oxygen-sensing electrode 6 low in activity with NOx.

EXAMPLES 111–116

Samples of sensor elements having the structure shown in FIG. 1 were produced in the same manner as in Reference Example 1, except for using materials shown in Table 19 (containing 10% by mass of a zirconia solid electrolyte) for the sensing electrodes 5, using zirconia containing 10 mol % of $CeO_2$ (porosity: 30%, average thickness: 15 μm) or zirconia containing 12 mol % of $SC_2O_3$ (porosity: 30%, average thickness: 15 μm) for the electrode-coating layers 11, and using Pt for the reference electrodes 7. With each of the resultant sensor samples set in an electric furnace, the detection performance to each detection gas containing $C_3H_6$ (30 ppm), CO (20 ppm) or $NH_3$ (50 ppm) was evaluated in the same manner as in Example 1. The results are shown in Table 19.

COMPARATIVE EXAMPLES 20–23

Sensor samples were produced to evaluate their detection performance in the same manner as in Examples 111–116 except that no electrode-coating layer was formed. The results are shown in Table 19.

TABLE 19

| No. | Sensing electrode[1] | Electrode-Coating Layer |
|---|---|---|
| Example 111 | $NiCr_2O_4$ | $CeO_2$ (10 mol %)-$ZrO_2$ |
| Example 112 | $NiCr_2O_4$ | $CeO_2$ (10 mol %)-$ZrO_2$ |
| Example 113 | Pt-Rh (5% by mass) | $CeO_2$ (10 mol %)-$ZrO_2$ |
| Example 114 | $Cr_2O_3$ | $CeO_2$ (10 mol %)-$ZrO_2$ |
| Example 115 | $NiCr_2O_4$ | $Sc_2O_3$ (12 mol %)-$ZrO_2$ |
| Example 116 | $NiCr_2O_4$ | $Sc_2O_3$ (12 mol %)-$ZrO_2$ |
| Com. Ex. 20 | $NiCr_2O_4$ | No |
| Com. Ex. 21 | $NiCr_2O_4$ | No |
| Com. Ex. 22 | Pt-Rh (5% by mass) | No |
| Com. Ex. 23 | $Cr_2O_3$ | No |

| | Initial Sensitivity (mV) | | | Change Ratio of |
|---|---|---|---|---|
| | $C_3H_6$[2] | CO[3] | $NH_3$[4] | Drift[5] (%) |
| Example 111 | −42 | — | — | +24 |
| Example 112 | −50 | — | — | +14 |
| Example 113 | — | −40 | — | +27 |
| Example 114 | — | — | −42 | −32 |
| Example 115 | −44 | — | — | +20 |
| Example 116 | −53 | — | — | +23 |
| Com. Ex. 22 | −46 | — | — | +63 |
| Com. Ex. 23 | −58 | — | — | +51 |
| Com. Ex. 24 | — | −41 | — | +72 |
| Com. Ex. 25 | — | — | −49 | −62 |

Note:
[1] Containing 10% by mass of zirconia solid electrolyte.
[2] Expressed by the difference between a sensor output obtained in the case of an $N_2$ base gas containing 5% by volume of oxygen, and a sensor output obtained in the case of a gas formulated by adding 30 ppm of $C_3H_6$ to the base gas.
[3] Expressed by the difference between a sensor output obtained in the case of an $N_2$ base gas containing 5% by volume of oxygen, and a sensor output obtained in the case of a gas formulated by adding 20 ppm of CO to the base gas.
[4] Expressed by the difference between a sensor output obtained in the case of an $N_2$ base gas containing 5% by volume of oxygen, and a sensor output obtained in the case of a gas formulated by adding 50 ppm of $NH_3$ to the base gas.
[5] Expressed by the difference (degree of change) between an initial sensitivity to 100 ppm of $NO_2$ and sensitivity to 100 ppm of $NO_2$ after the accelerated deterioration test. "+" means the increase in sensitivity, and "−" means the decrease in sensitivity.

As shown in Table 19, Examples 111–116 showed smaller drift than Comparative Examples 22–25. This proved that the use of the gas-detecting element of the present invention greatly suppressed drift in any gas of HC (hydrocarbons), CO (carbon monoxide) and $NH_3$ (ammonia).

EXAMPLES 117–120, COMPARATIVE EXAMPLE 24

Laminate-type NOx sensors having the structure shown in FIG. 21 were produced by the following procedures. Zirconia powder containing 6 mol % of yttria was used as starting material powder for zirconia solid electrolyte substrates to form green sheets. Each green sheet had a size of 0.25 mm×5 mm×50 mm. Incidentally, when a sintered substrate is used, the thickness of a substrate is about 200 μm. Each green sheet was cut to a rectangular shape, and screen-printed with each sensor structure portion. The green sheets were laminated and pressed to provide a laminate structure. Each of the resultant laminate structures was degreased at 500° C. for 2 hours in air and then sintered at 1400° C. for 3 hours in air.

$NiCr_2O_4$ was used for a NOx-sensing electrode 5 having a size of 0.7 mm×1.3 mm×0.003 mm. A reference electrode 7 made of Pt was formed on the zirconia solid electrolyte substrate 1 on the same surface as the NOx-sensing electrode 5 in the vicinity of the NOx-sensing electrode 5. The reference electrode 7 had a size of 0.7 mm×1.3 mm×0.003 mm, like the NOx-sensing electrode 5. Pt-3% by mass Rh was used for a NOx-converting electrode 8, and Pt was used for a conversion counter electrode 9. An electrode-coating film layer 51 of the NOx-converting electrode 8 was provided with a portion directly bonded to the solid electrolyte substrate 2.

The electrode-coating film layer 51 of the NOx-converting electrode 8 was formed by a zirconia solid electrolyte containing a stabilizer with various porosity and thickness. Produced in Comparative Example 26 was a laminate-type NOx sensor having the same structure as in Example 117 except for having no electrode-coating film layer 51.

Each laminate-type NOx sensor was assembled in an apparatus for evaluating gas response characteristics, to carry out the following evaluation on the effects of the electrode-coating layer 51. First, each laminate-type NOx sensor was stationarily operated at 600° C. in a nitrogen gas (base gas) atmosphere containing 5% by volume of oxygen in the evaluation apparatus, to measure the impedance of interface between the conversion electrode and the solid electrolyte substrate at the initial stage of operation and after predetermined time of operation, respectively. The stability of the conversion electrode 8 was evaluated by the change ratio of the interface impedance.

A detection gas formulated by adding 100 ppm of NO to the base gas was supplied to each laminate-type NOx sensor at a temperature of 600° C., to measure the sensor output (first output) to NO. Next, each laminate-type NOx sensor was stationarily operated at 600° C. for predetermined time in a nitrogen gas (reducing gas) atmosphere containing 10% of carbon monoxide (CO) and 5000 ppm of propane ($C_3H_8$), and then the detection gas was supplied to each laminate-type NOx sensor at a temperature of 600° C. to measure the sensor output (second output) to NO. The first output is called a sensor output (sensitivity) at the initial stage of operation, and the second output is called a sensor output (sensitivity) after operation. The stability of the conversion electrode 8 was evaluated by the change ratio from the sensor output at the initial stage of operation to the sensor output after operation.

The stabilizers added to the conversion electrode-coating layer 51, the thickness and porosity of the coating layer 51, the change ratio of interface impedance and the change ratio of sensor output (sensitivity) are shown in Table 20.

TABLE 20

| No. | Electrode-Coating Layer For Conversion Electrode | | | Change Ratio of Interface Impedance[1] | Change Ratio of Sensitivity[2] |
|---|---|---|---|---|---|
| | Material | Thickness (μm) | Porosity (vol. %) | | |
| Com. Ex. 24 | No | — | — | 30% | −19% |
| Ex. 117 | $CeO_2$ (12 mol %)-$ZrO_2$ | 10 | 30 | 3% | −3% |
| Ex. 118 | $Y_2O_3$ (8 mol %)-$ZrO_2$ | 10 | 30 | 2% | −3% |
| Ex. 119 | MgO (15 mol %)-$ZrO_2$ | 10 | 30 | 6% | −5% |
| Ex. 120 | $Sc_2O_3$ (12 mol %)-$ZrO_2$ | 10 | 30 | 5% | −6% |

Note:
[1]The change ratio of interface impedance before and after the operation.
[2]The change ratio of sensitivity to 100 ppm of NO before and after the exposure to the reducing gas for predetermined time.

While the interface impedance increased by 30% in the laminate-type NOx sensor of Comparative Example 26, in which the NOx-converting electrode-coating layer 51 was not formed, the change ratio of interface impedance was as small as 2–6% in the laminate-type NOx sensors in Examples 117–120. This proved that the formation of the electrode-coating layer 51 made of a zirconia solid electrolyte containing ceria ($CeO_2$), yttria ($Y_2O_3$), magnesia (MgO) or scandia ($Sc_2O_3$) as a stabilizer on the conversion electrode 8 contributed to the stabilization of interface between the conversion electrode 8 and the solid electrolyte substrate 2.

While the sensitivity to 100 ppm of NO decreased by 19% in the laminate-type NOx sensor of Comparative Example 26, in which the electrode-coating layer 51 was not formed on the NOx-converting electrode, the change ratio of sensitivity was as low as 3–6% in the laminate-type NOx sensors in Examples 117–120. This proved that the sensitivity of the laminate-type NOx sensor was stabilized by forming the electrode-coating layer 51 made of a zirconia solid electrolyte containing a stabilizer on the conversion electrode 8.

EXAMPLES 121–123

Each laminate-type NOx sensor was produced and evaluated in the same manner as in Example 117 except for changing the porosity of the conversion electrode-coating layer 51. The influence of the porosity of the conversion electrode-coating layer 51 on the change ratio of interface impedance and the change ratio of sensor output (sensitivity) was examined. The results are shown in Table 21.

TABLE 21

| No. | Electrode-Coating Layer for Conversion Electrode | | | Change Ratio of Interface Impedance[1] | Change Ratio of Sensitivity[2] |
|---|---|---|---|---|---|
| | Material | Thickness (μm) | Porosity (vol. %) | | |
| Ex. 117 | $CeO_2$ (12 mol %)-$ZrO_2$ | 10 | 30 | 3% | −3% |
| Ex. 121 | $CeO_2$ (12 mol %)-$ZrO_2$ | 10 | 10 | 2% | −2% |

TABLE 21-continued

| No. | Material | Electrode-Coating Layer for Conversion Electrode Thickness (μm) | Porosity (vol. %) | Change Ratio of Interface Impedance[1] | Change Ratio of Sensitivity[2] |
|---|---|---|---|---|---|
| Ex. 122 | CeO$_2$ (12 mol %)-ZrO$_2$ | 10 | 20 | 3% | −2% |
| Ex. 123 | CeO$_2$ (12 mol %)-ZrO$_2$ | 10 | 50 | 4% | −6% |

Note:
[1]The change ratio of interface impedance before and after the operation.
[2]The change ratio of sensitivity to 100 ppm of NO before and after the exposure to the reducing gas for predetermined time.

A zirconia solid electrolyte stabilized by 12 mol % CeO$_2$ was used for the NOx-converting electrode-coating layer 51. By changing the porosity of the conversion electrode-coating layer 51 to 10–50%, the change of interface impedance and sensor output (sensitivity) could be suppressed, thereby providing the laminate-type NOx sensors with excellent stability.

EXAMPLES 124–126

Each laminate-type NOx sensor produced and evaluated in the same manner as in Example 117 except for changing the thickness of the conversion electrode-coating layer 51. The influence of the thickness of the conversion electrode-coating layer 51 on the change ratio of interface impedance and the change ratio of sensor output (sensitivity) was examined. The results are shown in Table 22.

TABLE 22

| No. | Material | Electrode-Coating Layer for Conversion Electrode Thickness (μm) | Porosity (vol. %) | Change Ratio of Interface Impedance[1] | Change Ratio of Sensitivity[2] |
|---|---|---|---|---|---|
| Ex. 117 | CeO$_2$ (12 mol %)-ZrO$_2$ | 10 | 30 | 3% | −3% |
| Ex. 124 | CeO$_2$ (12 mol %)-ZrO$_2$ | 3 | 30 | 5% | −7% |
| Ex. 125 | CeO$_2$ (12 mol %)-ZrO$_2$ | 15 | 30 | 3% | −2% |
| Ex. 126 | CeO$_2$ (12 mol %)-ZrO$_2$ | 20 | 30 | 2% | −2% |

Note:
[1]The change ratio of interface impedance before and after the operation.
[2]The change ratio of sensitivity to 100 ppm of NO before and after the exposure to the reducing gas for predetermined time.

A zirconia solid electrolyte stabilized by 12 mol % of CeO$_2$ was used for the NOx-converting electrode-coating layer 51. By regulating the thickness of the conversion electrode-coating layer 51 to 3–20 μm, the change of interface impedance and sensor output (sensitivity) could be suppressed, thereby providing the laminate-type NOx sensors with excellent stability.

EXAMPLES 127–138

Each laminate-type NOx sensor produced and evaluated in the same manner as in Example 117 except for adding various precious metals and/or metal oxides to a zirconia solid electrolyte for the conversion electrode-coating layer 51. The influence of the additives to the conversion electrode-coating layer 51 on the change ratio of interface impedance and the change ratio of sensor output (sensitivity) was examined. The results are shown in Table 23.

TABLE 23

| No. | Material | Electrode-Coating Layer for Conversion Electrode Thickness (μm) | Porosity (vol. %) | Change Ratio of Interface Impedance[1] | Change Ratio of Sensitivity[2] |
|---|---|---|---|---|---|
| Ex. 117 | No | 10 | 30 | 3% | −3% |
| Ex. 127 | 20 vol. % Rh | 10 | 30 | 2% | −2% |
| Ex. 128 | 20 vol. % Ir | 10 | 30 | 4% | −2% |
| Ex. 129 | 5 vol. % Au | 10 | 30 | 5% | −3% |
| Ex. 130 | 20 vol. % (Pt-3 wt. % Rh) | 10 | 30 | 3% | −1% |
| Ex. 131 | 20 vol.% (Pt-10 wt. % Ir) | 10 | 30 | 3% | −2% |
| Ex. 132 | 20 vol. % (Pt-3 wt. % Au) | 10 | 30 | 4% | −3% |
| Ex. 133 | 10 vol. % Cr$_2$O$_3$ | 10 | 30 | 5% | −2% |
| Ex. 134 | 10 vol. % NiO | 10 | 30 | 6% | −2% |
| Ex. 135 | 10 vol. % NiCr$_2$O$_4$ | 10 | 30 | 4% | −2% |
| Ex. 136 | 10 vol. % MgCr$_2$O$_4$ | 10 | 30 | 3% | −2% |
| Ex. 137 | 10 vol. % FeCr$_2$O$_4$ | 10 | 30 | 3% | −2% |
| Ex. 138 | 10 vol. % (Pt-3 wt. % Rh) + 10 vol. % NiCr$_2$O$_4$ | 10 | 30 | 2% | −1% |

Note:
[1]The change ratio of interface impedance before and after the operation.
[2]The change ratio of sensitivity of 100 ppm of NO before and after the exposure to the reducing gas for predetermined time.

The change of interface impedance and sensor output (sensitivity) could be suppressed to provide the laminate-type NOx sensors with excellent stability in Examples 127–138, in which precious metals and/or metal oxides were added, like in Example 117, in which no additive was added to the conversion electrode-coating layer 51.

EXAMPLES 139

Laminate-type NOx sensors were produced in the same manner as in Example 117, except that electrode underlayers 52 (porosity: 10%, thickness: 3 μm) having various compositions were formed on the conversion electrodes 8 as shown in FIG. 22. In the structure shown in FIG. 22, the electrode-coating film layer 51 of the NOx-converting electrode 8 had a portion bonded to the solid electrolyte substrate 2 via the electrode underlayer 52. The electrode underlayer 52 was based on a zirconia solid electrolyte, which contained various stabilizers and/or additives as shown in Table 24. Incidentally, the amount of a stabilizer is expressed by "mol %" based on the total amount (100 mol %) of a stabilized zirconia solid electrolyte, and the amount of an additive is expressed by "% by volume" based on the total amount (100% by volume) of the electrode underlayer 52. Also, a zirconia solid electrolyte stabilized by 12 mol % $CeO_2$ was used for the conversion electrode-coating layer 51, and its porosity and thickness were 30% by volume and 10 μm, respectively.

Laminate-type NOx sensors provided with various conversion electrode underlayers 52 were measured with respect to interface impedance and sensor output (sensitivity) in the same manner as in Example 117. The influence of the composition of the electrode underlayer 52 on the change ratio of interface impedance and the change ratio of sensor output (sensitivity) was examined. The results are shown in Table 24.

TABLE 24

| No. | Electrode-Coating Layer for Conversion Electrode | | Change Ratio of Interface Impedance[1] | Change Ratio of Sensitivity[2] |
|---|---|---|---|---|
| | Structure | Material | | |
| Ex. 117 | FIG. 21 | No | 3% | −3% |
| Ex. 139 | FIG. 22 | $CeO_2$ (12 mol %)-$ZrO_2$ | 3% | −3% |

Note:
[1] The change ratio of interface Impedance before and after the operation.
[2] The change ratio of sensitivity to 100 ppm of NO before and after the exposure to the reducing gas for predetermined time.

The change of interface impedance and the change of sensor output (sensitivity) could be suppressed in the laminate-type NOx sensors each having a electrode underlayer 52 Example 150, regardless of the composition of the electrode underlayer 52, the presence of absence of a stabilizer and an additive and its type. As a result, the laminate-type NOx sensors were provided with excellent stability.

Though the gas-detecting element and the gas-detecting device of the present invention have been explained above referring to the drawings, it should be noted that the present invention is not restricted thereto, and that various modifications can be made thereto as long as they do not change the spirit of the present invention.

By covering the electrodes fixed onto the oxygen-ion-conductive solid electrolyte substrate with electrode-coating layers, the electrochemical activity of electrode interface can be stabilized, and the interface impedance of electrodes can be reduced. Accordingly, the gas-detecting element and gas-detecting device of the present invention are improved in response performance during gas detecting, exhibiting high precision stably in the detection of the concentration of a detection object gas.

Also, by laminating the oxygen-ion-conductive electrode-coating layer, through which a detection object gas is diffusible, on the conversion electrode fixed onto the solid electrolyte substrate made of a oxygen ion conductor, and adhering the electrode-coating layer to the solid electrolyte substrate directly or via the electrode underlayer made of an oxygen-ion-conductive solid electrolyte, it is possible to alleviate thermal strain due to the difference in thermal expansion and sintering shrinkage, etc. between the conversion electrode and the solid electrolyte, and it is possible to stabilize the electrochemical activity of the conversion electrode.

The gas-detecting element and the gas-detecting device of the present invention having the above features have high sensitivity and can perform stable gas detection, particularly suitable for the detection of NOx.

What is claimed is:

1. A gas-detecting element comprising an oxygen-ion-conductive solid electrolyte substrate, a sensing electrode fixed onto said solid electrolyte substrate and active with a detection object gas and oxygen, and a reference electrode fixed onto said solid electrolyte substrate and active with at least oxygen, to determine the concentration of said detection object gas from the potential difference between said sensing electrode and said reference electrode, wherein said sensing electrode and/or said reference electrode is covered by an electrode-coating layer made of an oxygen-ion-conductive solid electrolyte, wherein said electrode-coating layer has a portion bonded to said solid electrolyte substrate directly or via an electrode underlayer made of an oxygen-ion-conductive solid electrolyte, and wherein said sensing electrode and/or said reference electrode is fixed onto said solid electrolyte substrate or said electrode underlayer via an electric insulating layer.

2. A gas-detecting element comprising an oxygen-ion-conductive solid electrolyte substrate, a sensing electrode fixed onto said solid electrolyte substrate and active with a detection object gas and oxygen, an oxygen-sensing electrode fixed onto said solid electrolyte substrate and active with at least oxygen, a reference electrode fixed onto said solid electrolyte substrate and positioned in an atmosphere separated from a detection object atmosphere and active with oxygen, to determine the concentration of said detection object gas from the difference ($E_1-E_2$) between a potential difference $E_1$ between said sensing electrode and said reference electrode and a potential difference $E_2$ between said oxygen-sensing electrode and said reference electrode, wherein at least one of sensing electrode, said reference electrode and said oxygen-sensing electrode is covered by an electrode-coating layer made of an oxygen-ion-conductive solid electrolyte, and wherein said electrode-coating layer has a portion bonded to said solid electrolyte substrate directly or via an electrode underlayer made of an oxygen-ion-conductive solid electrolyte.

3. A gas-detecting element comprising
an oxygen-ion-conductive solid electrolyte substrate,
a sensing electrode fixed onto said solid electrolyte substrate and active with a detection object gas and oxygen, and
a reference electrode fixed onto said solid electrolyte substrate and active with at least oxygen,
to determine the concentration of said detection object gas from the potential difference between said sensing electrode and said reference electrode,
wherein at least said sensing electrode is covered by an electrode-coating layer made of an oxygen-ion-conductive solid electrolyte,
wherein said electrode-coating layer has a portion bonded to said solid electrolyte substrate directly or via an electrode underlayer made of an oxygen-ion-conductive solid electrolyte, and
wherein said electrode-coating layer covering said sensing electrode contains a precious metal active with said detection object gas and oxygen.

4. A gas-detecting element comprising
an oxygen-ion-conductive solid electrolyte substrate,
a sensing electrode fixed onto said solid electrolyte substrate and active with a detection object gas and oxygen, and
a reference electrode fixed onto said solid electrolyte substrate and active with at least oxygen,
to determine the concentration of said detection object gas from the potential difference between said sensing electrode and said reference electrode,
wherein said sensing electrode and/or said reference electrode is covered by an electrode-coating layer made of an oxygen-ion-conductive solid electrolyte,
wherein said electrode-coating layer has a portion bonded to said solid electrolyte substrate directly or via an electrode underlayer made of an oxygen-ion-conductive solid electrolyte, and
wherein said electrode-coating layer covering said sensing electrode and/or said reference electrode contains a precious metal inactive with said detection object gas but active with oxygen.

5. A gas-detecting device comprising
(a) a gas-measuring chamber defined by first and second oxygen-ion-conductive solid electrolyte substrates disposed with a predetermined gap;
(b) a gas inlet provided so that a detection gas flows into said gas-measuring chamber with a predetermined gas diffusion resistance;
(c) a gas-detecting element comprising a sensing electrode fixed onto said first solid electrolyte substrate such that it is exposed to an atmosphere in said gas-measuring chamber, and active with a detection object gas and oxygen, and a reference electrode fixed onto said first solid electrolyte substrate and active with at least oxygen; and
(d) a detection-object-gas-converting pump element comprising
(i) a detection-object-gas-converting electrode fixed onto said second solid electrolyte substrate such that it is exposed to atmosphere in said gas-measuring chamber, and active with a detection object gas and oxygen,
(ii) a detection-object-gas-converting counter electrode fixed onto said second solid electrolyte substrate such that it is exposed to an atmosphere containing oxygen and/or an oxide gas, and active with oxygen, which can select the oxidation or reduction of a detection object gas depending on conditions;
(e) a means for measuring the potential difference between said sensing electrode and said reference electrode; and
(f) a voltage-applying means for driving said conversion pump element, thereby detecting the potential difference between said sensing electrode and said reference electrode while applying a predetermined voltage to said conversion pump element, to determine the concentration of said detection object gas in said detection gas; and
wherein said detection-object-gas-converting electrode is covered by an electrode-coating layer made of an oxygen-ion-conductive solid electrolyte, through which said detection object gas can reach to said electrode; and said electrode-coating layer has a portion bonded to said second solid electrolyte substrate directly or via an electrode underlayer made of a solid electrolyte,
said electrode-coating layer covering said detection-object-gas-converting electrode containing at least one precious metal selected from the group consisting of platinum, rhodium, iridium, gold and alloys containing these metals, and/or at least one metal oxide selected from the group consisting of $Cr_2O_3$, NiO, $NiCr_2O_4$, $MgCr_2O_4$ and $FeCr_2O_4$.

6. A gas-detecting device comprising
(a) a gas-measuring chamber defined by first and second oxygen-ion-conductive solid electrolyte substrates disposed with a predetermined gap;
(b) a gas inlet provided so that a detection gas flows into said gas-measuring chamber with a predetermined gas diffusion resistance;
(c) a gas-detecting element comprising a sensing electrode fixed onto said first solid electrolyte substrate such that it is exposed to an atmosphere in said gas-measuring chamber, and active with a detection object gas and oxygen, and a reference electrode fixed onto said first solid electrolyte substrate and active with at least oxygen; and
(d) a detection-object-gas-converting pump element comprising
(i) a detection-object-gas-converting electrode fixed onto said second solid electrolyte substrate such that it is exposed to an atmosphere in said gas-measuring chamber, and active with a detection object gas and oxygen,
(ii) a detection-object-gas-converting counter electrode fixed onto said second solid electrolyte substrate such that it is exposed to an atmosphere containing oxygen and/or an oxide gas, and active with oxygen, which can select the oxidation or reduction of a detection object gas depending on conditions;
(e) a means for measuring the potential difference between said sensing electrode and said reference electrode; and
(f) a voltage-applying means for driving said conversion pump element, thereby detecting the potential difference between said sensing electrode and said reference electrode while applying predetermined voltage to said conversion pump element, to determine the concentration of said detection object gas in said detection gas;

wherein an electrode underlayer made of zirconia solid electrode is interposed between said detection-object-gas-converting electrode and said second solid electrode substrate; and said electrode underlayer contains at least one metal oxide selected from the group consisting of $Cr_2O_3$, $NiO$, $NiCr_2O_4$, $MgCr_2O_4$ and $FeCr_2O_4$.

* * * * *